(12) United States Patent
Chen et al.

(10) Patent No.: US 8,592,432 B2
(45) Date of Patent: Nov. 26, 2013

(54) COMPOUNDS AND COMPOSITIONS AS PROTEIN KINASE INHIBITORS

(76) Inventors: Bei Chen, San Diego, CA (US); Tao Jiang, San Diego, CA (US); Thomas H. Marsilje, San Diego, CA (US); Pierre-Yves Michellys, San Marcos, CA (US); Truc Ngoc Nguyen, San Diego, CA (US); Wei Pei, San Diego, CA (US); Baogen Wu, San Diego, CA (US); Zhaobo Gao, Jiangsu (CN); Yonghui Ge, Suzhou (CN); Chen Huang, Shanghai (CN); Yuncheng Li, Jiangsu (CN); Xuefeng Zhu, San Diego, CA (US)

( * ) Notice: Subject to any disclaimer, the term of this patent is extended or adjusted under 35 U.S.C. 154(b) by 290 days.

(21) Appl. No.: 12/936,199

(22) PCT Filed: Apr. 3, 2009

(86) PCT No.: PCT/US2009/039383
§ 371 (c)(1),
(2), (4) Date: Dec. 28, 2010

(87) PCT Pub. No.: WO2009/126515
PCT Pub. Date: Oct. 15, 2009

(65) Prior Publication Data
US 2011/0135668 A1    Jun. 9, 2011

Related U.S. Application Data

(60) Provisional application No. 61/043,111, filed on Apr. 7, 2008, provisional application No. 61/116,023, filed on Nov. 19, 2008.

(51) Int. Cl.
| | | |
|---|---|---|
| *A61K 31/506* | (2006.01) | |
| *A61K 31/5377* | (2006.01) | |
| *C07D 239/42* | (2006.01) | |
| *C07D 239/30* | (2006.01) | |
| *C07D 295/108* | (2006.01) | |
| *C07D 487/04* | (2006.01) | |
| *A61P 35/00* | (2006.01) | |
| *A61P 35/02* | (2006.01) | |
| *A61P 35/04* | (2006.01) | |

(52) U.S. Cl.
USPC ........ 514/262.1; 544/297; 544/262; 544/118; 544/280; 514/275; 514/234.2; 514/265.1

(58) Field of Classification Search
USPC .......................................... 544/297; 514/275
See application file for complete search history.

(56) References Cited

U.S. PATENT DOCUMENTS

| | | | |
|---|---|---|---|
| 8,039,479 B2 * | 10/2011 | Michellys et al. | 514/275 |
| 2005/0256111 A1 | 11/2005 | Kath et al. | |
| 2008/0176881 A1 | 7/2008 | Michellys et al. | |

FOREIGN PATENT DOCUMENTS

| | | |
|---|---|---|
| WO | WO2004056786 | 7/2004 |
| WO | WO2005013996 | 2/2005 |
| WO | WO2005016893 | 2/2005 |
| WO | WO2005016894 | 2/2005 |
| WO | WO2006021454 | 3/2006 |
| WO | WO20068056399 | 6/2006 |
| WO | WO2008051547 | 5/2008 |
| WO | WO2008073687 | 6/2008 |
| WO | WO2009032668 | 3/2009 |
| WO | WO2009032694 | 3/2009 |

* cited by examiner

*Primary Examiner* — Susanna Moore
(74) *Attorney, Agent, or Firm* — Emily Tongco Wu; Genomics Institute of The Novartis Research Foundation

(57) ABSTRACT

The invention provides novel pyrimidine derivatives and pharmaceutical compositions thereof, and methods for using such compounds. For example, the pyrimidine derivatives of the invention may be used to treat, ameliorate or prevent a condition which responds to inhibition of anaplastic lymphoma kinase (ALK) activity, c-ros oncogene (ROS), insulin-like growth factor (IGF-1R), and/or insulin receptor (InsR) or a combination thereof.

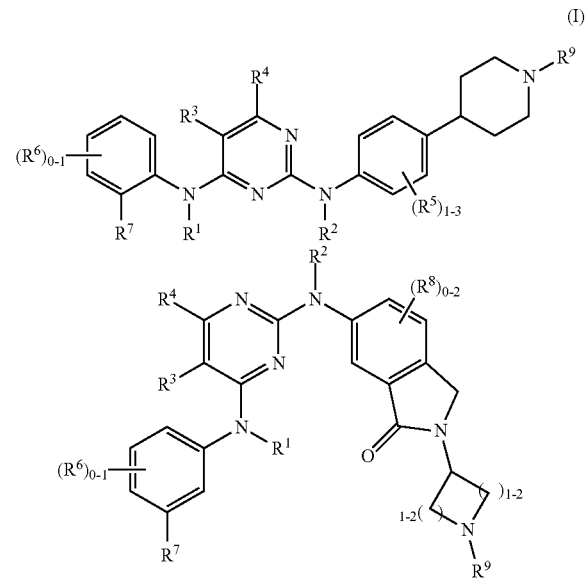

9 Claims, No Drawings

COMPOUNDS AND COMPOSITIONS AS PROTEIN KINASE INHIBITORS

CROSS-REFERENCE TO RELATED APPLICATIONS

This application is a 371 U.S. national phase application of international application number PCT/US2009/039383 filed 3 Apr. 2009, which application claims priority to U.S. provisional patent application Ser. No. 61/116,023 filed 19 Nov. 2008 and U.S. provisional patent application Ser. No. 61/043,111 filed 7 Apr. 2008, each of which is incorporated herein by reference in its entirety and for all purposes.

TECHNICAL FIELD

The invention relates to protein kinase inhibitors, more particularly novel pyrimidine derivatives and pharmaceutical compositions thereof, and their use as pharmaceuticals.

BACKGROUND ART

Cancer is a disease resulting from an abnormal growth of tissue. Certain cancers have the potential to invade into local tissues and also metastasize to distant organs. This disease can develop in a wide variety of different organs, tissues and cell types. Therefore, the term "cancer" refers to a collection of over a thousand different diseases.

Anaplastic lymphoma kinase (ALK), a member of the insulin receptor superfamily of receptor tyrosine kinases, has been implicated in oncogenesis in hematopoietic and non-hematopoietic tumors. The aberrant expression of full-length ALK receptor proteins has been reported in neuroblastomas and glioblastomas; and ALK fusion proteins have occurred in anaplastic large cell lymphoma. The study of ALK fusion proteins has also raised the possibility of new therapeutic treatments for patients with ALK-positive malignancies. (Pulford et al., Cell. Mol. Life Sci. 61:2939-2953 (2004)).

Insulin-like growth factor (IGF-1) signaling is highly implicated in cancer, with the IGF-1 receptor (IGF-1R) as the predominating factor. IGR-1R is important for tumor transformation and survival of malignant cells, but is only partially involved in normal cell growth. Targeting of IGF-1R has been suggested to be a promising option for cancer therapy. (Larsson et al., Br. J. Cancer 92:2097-2101 (2005)).

ROS1, V-ros Avian UR2 Sarcoma Virus Oncogene Homolog 1 (also known as ROS) is highly expressed in a variety of tumor cell lines. ROS1 is currently an orphan receptor tyrosine kinase whose kinase domain is mostly related to ALK. ROS1 is highly expressed in a variety of tumor cell lines. ROS1 fusion proteins resulting from genetic aberrations have been found in lung cancer and in certain glioblastoma cell lines (Rikova K. et al Cell 131:1190 (2007); Sharma S. Et al Oncogene Res. 5: 91 (1989)). Aberrant expression of ROS1 has been reported in glioma (Watkins D. et al Cancer Genet Cytogenet. 1994 72:130 (1994)). ROS1 kinase inhibitors may be able to block growth of the tumors driven by ROS1 fusions or aberrant expression or activation.

Despite advancements in the art, there remains a need for cancer treatments and anti-cancer compounds.

DISCLOSURE OF THE INVENTION

The invention relates to novel pyrimidine derivatives and pharmaceutical compositions thereof, and their use as pharmaceuticals.

In one aspect, the invention provides a compound of Formula (1) or (2):

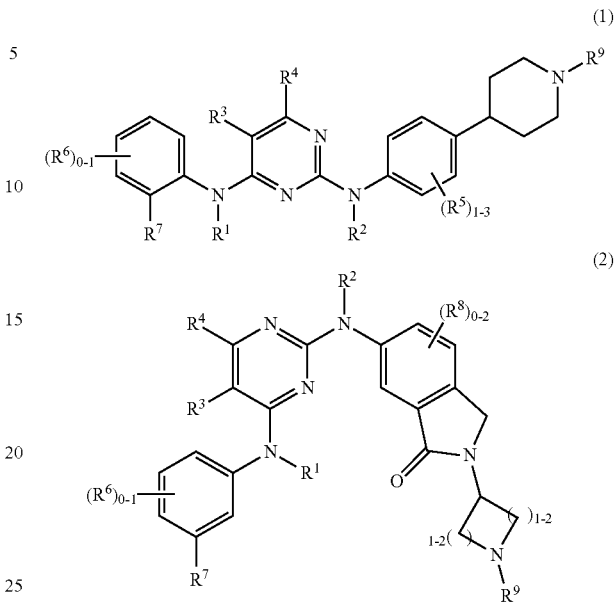

or a physiologically acceptable salt thereof;

$R^1$ and $R^2$ are independently H, $C_{1-6}$ alkyl or halo-substituted $C_{1-6}$ alkyl;

$R^3$ is halo, $C_{1-6}$ alkyl, or a halo-substituted $C_{1-6}$ alkyl;

$R^4$ is H;

alternatively, $R^3$ and $R^4$ together with the carbon atoms to which they are attached to may form a 5-6 membered ring containing 1-3 heteroatoms selected from N, O and S, and optionally substituted with 1-2 $R^{10}$ groups wherein $R^{10}$ is halo, $C_{1-6}$ alkyl, $C_{2-6}$ alkenyl, $C_{2-6}$ alkynyl, optionally substituted phenyl or $NR_2$;

$R^5$, $R^6$ and $R^8$ are independently $C_{1-6}$ alkyl, $C_{1-6}$ alkoxy, $C_{2-6}$ alkenyl or $C_{2-6}$ alkynyl, each of which may be optionally substituted with halo, amino or hydroxyl groups; halo, nitro, cyano, $CR(OR^{17})R^{17}$, $OR^{17}$, $NR(R^{17})$, $CR(R^{17})NRR^{17}$, $(CR_2)_qY$, $C(O)O_{0-1}R^{17}$, $C(O)NR(R^{17})$, $C(O)CRR^{17}-NR(R^{17})$, $C(O)NR(CR_2)_pNR(R^{17})$, $C(O)NR(CR_2)_pOR^{17}$, $C(O)NR(CR_2)_pSR^{17}$, $C(O)NR(CR_2)_pS(O)_{1-2}R^{18}$, $S(O)_{0-2}R^{18}$, $(CR_2)_{1-6}NR(CR_2)_pOR^{17}$, $(CR_2)_{1-6}NR(CR_2)_qC(O)R^{18}$, $S(O)_2NRR^{17}$, $S(O)_2NR(CR_2)_pNR(R^{17})$, or $S(O)_2NR(CR_2)_pOR^{17}$; wherein $R^8$ may be on any position of the fused ring;

$R^7$ is $S(O)_{0-2}R^{19}$, $S(O)_2NRR^{20}$ or $C(O)NR(R^{20})$; wherein $R^{19}$ and $R^{20}$ are independently $C_{1-6}$ alkyl, halo-substituted $C_{1-6}$ alkyl or $C_{3-7}$ cycloalkyl; or $R^{20}$ is H;

each $R^9$ is independently -L-$CR(OR^{17})$—$C_tF_{(2t+1)}$ wherein t is 1-3; -L-C(O)—$CR(R^{17})$—$NRR^{17}$, -L-C(O)—NR—$(CR_2)_p$—$NRR^{17}$, -L-C(O)NR$(CR_2)_p$OR$^{17}$, -L-C(O)—$(CR_2)_p$—NR—C(O)—$R^{18}$, -L-C(O)NR$(CR_2)_p$SR$^{17}$, -L-C(O)NR$(CR_2)_p$S(O)$_{1-2}$R$^{18}$, $(CR_2)_p$NR$(CR_2)_p$OR$^{17}$ or $(CR_2)_p$NR-L-C(O)R$^{18}$, -L-S(O)$_2$R$^{18}$, -L-S(O)$_2$NRR$^{17}$, -L-S(O)$_2$NR$(CR_2)_p$NR$(R^{17})$, -L-S(O)$_2$NR$(CR_2)_p$OR$^{17}$ or a radical selected from formula (a), (b), (c) or (d):

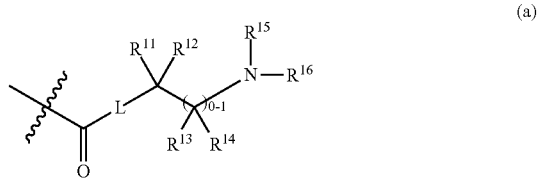

-continued

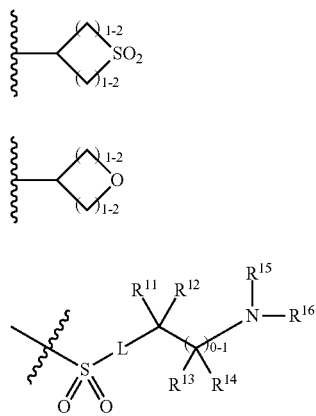

(b)

(c)

(d)

wherein $R^{11}$, $R^{12}$, $R^{13}$, $R^{14}$, $R^{15}$ and $R^{16}$ are independently selected from H, or $C_{1-6}$ alkyl, $C_{1-6}$ alkoxy, $C_{2-6}$ alkenyl or $C_{2-6}$ alkynyl, each of which may be optionally substituted with halo, amino or hydroxyl groups; or $R^{11}$ and $R^{12}$, $R^{12}$ and $R^{15}$, $R^{15}$ and $R^{16}$, $R^{13}$ and $R^{14}$, or $R^{13}$ and $R^{15}$ together with the carbon and/or nitrogen atoms to which they are attached may form a 3-7 membered saturated, unsaturated or partially unsaturated ring optionally containing up to 3 atoms or groups selected from C(O), N, O and $S(O)_{0-2}$;

L is $(CR_2)_{1-4}$ or a bond;

$R^{17}$ and $R^{18}$ are independently $C_{1-6}$ alkyl, halo-substituted $C_{1-6}$ alkyl, $C_{2-6}$ alkenyl or $C_{2-6}$ alkynyl; or $R^{17}$ is H;

Y is a $C_{3-12}$ carbocyclic ring, $C_{6-10}$ aryl; or a 5-10 membered heteroaryl or 4-10 membered heterocyclic ring; each of which is optionally substituted with 1-3 $R^6$ groups;

each R is H or $C_{1-6}$ alkyl;

p is 2-4; and q is 0-4.

In one embodiment, the invention provides a compound of Formula (2A):

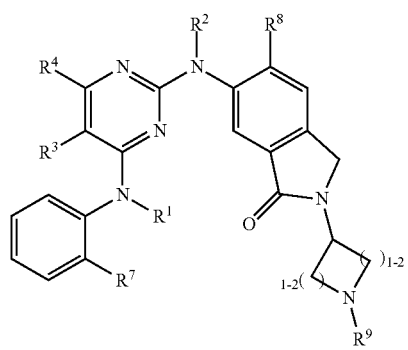

(2A)

wherein $R^3$ is halo;

$R^7$ is $S(O)_{0-2}R^{19}$;

$R^8$ is methoxy, ethoxy or isopropoxy;

$R^9$ is -L-CR(OR$^{17}$)—C$_t$F$_{(2t+1)}$ wherein t is 1-3; -L-S(O)$_2$R$^{18}$, -L-S(O)$_2$NRR$^{17}$, -L-S(O)$_2$NR(CR$_2$)$_p$NR(R$^{17}$), -L-S(O)$_2$NR(CR$_2$)$_p$OR$^{17}$ or a radical selected from formula (a), (b), (c) or (d):

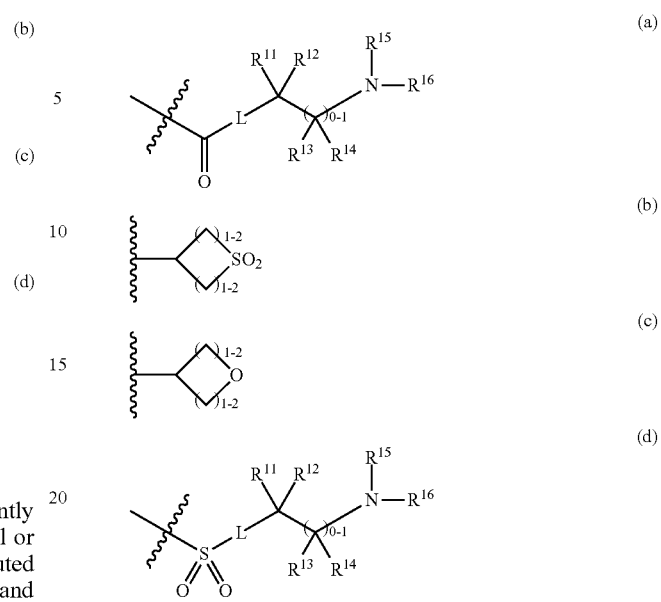

(a)

(b)

(c)

(d)

wherein $R^1$, $R^2$, $R^4$, $R^{11}$, $R^{12}$, $R^{13}$, $R^{14}$, $R^{15}$, $R^{16}$, $R^{17}$, $R^{18}$, $R^{19}$, L and p are as defined in Formula (1) or (2).

In some examples, the invention provides a compound of Formula (3):

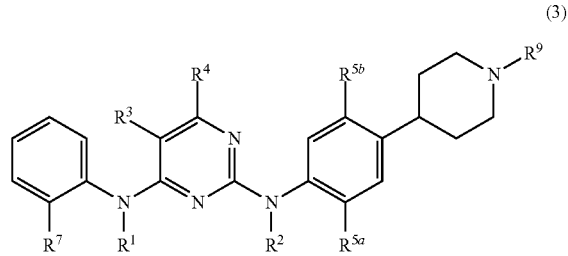

(3)

wherein $R^3$ is halo;

alternatively, $R^3$ and $R^4$ together with the carbon atoms to which they are attached to may form a 5-6 membered ring containing 1-3 N heteroatoms, and optionally substituted with 1-2 $R^{10}$ groups;

$R^{5a}$ and $R^{5b}$ are independently halo, hydroxyl, $C_{1-6}$ alkyl, $C_{1-6}$ alkoxy, halo-substituted $C_{1-6}$ alkyl or halo-substituted $C_{1-6}$ alkoxy;

$R^7$ is $S(O)_{0-2}R^{19}$;

$R^1$, $R^2$, $R^9$, $R^{10}$ and $R^{19}$ are as defined in Formula (1) or (2).

In particular embodiments in the above Formula (3), $R^{5a}$ is methoxy or isopropoxy;

$R^{5b}$ is or methyl;

$R^9$ is -L-CR(OR$^{17}$)—C$_t$F$_{(2t+1)}$ wherein t is 1-3; -L-S(O)$_2$R$^{18}$, -L-S(O)$_2$NRR$^{17}$, -L-S(O)$_2$NR(CR$_2$)$_p$NR(R$^{17}$), -L-S(O)$_2$NR(CR$_2$)$_p$OR$^{17}$ or a radical selected from formula (a), (b), (c) or (d):

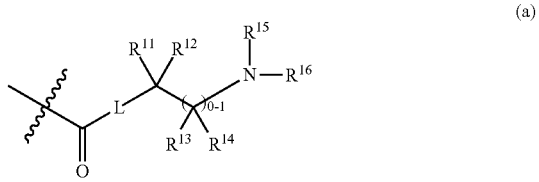

(a)

-continued (b)
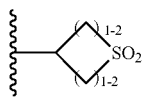

(c)
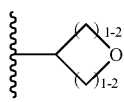

(d)
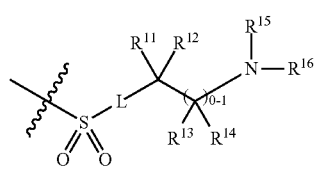

wherein $R^{11}$, $R^{12}$, $R^{13}$, $R^{14}$, $R^{15}$, $R^{16}$, $R^{17}$, $R^{18}$, L and p are as defined in Formula (1) or (2).

In other particular embodiments, the invention provides a compound of Formula (3A), (3B), (3C) or (3D):

(3A)
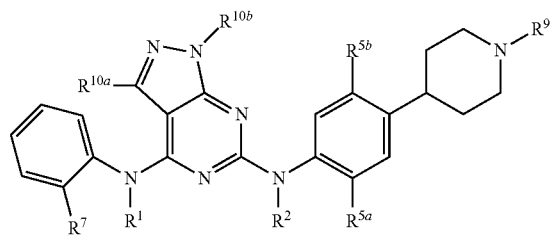

(3B)
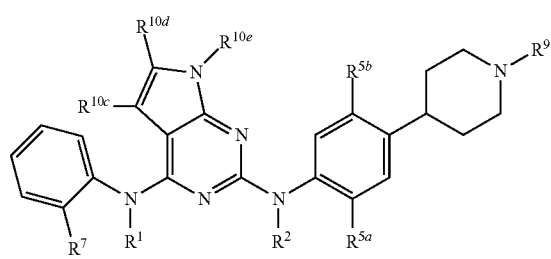

(3C)
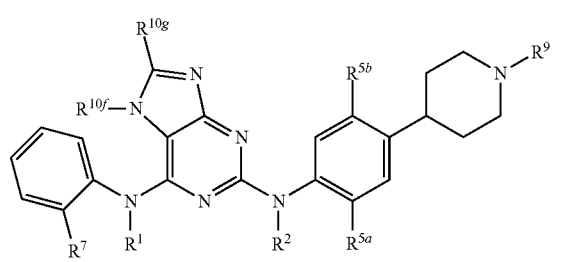

(3D)
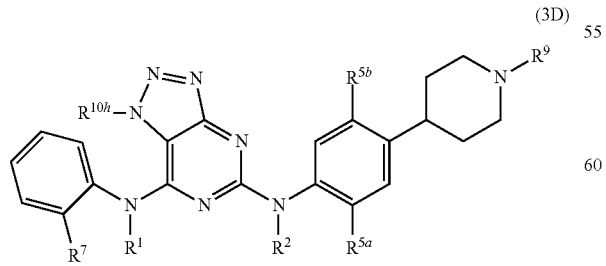

wherein $R^{5a}$ is methoxy or isopropoxy;
$R^{5b}$ is methyl;
$R^{10b}$, $R^{10e}$, $R^{10f}$ and $R^{10h}$ are independently H or $C_{1-6}$ alkyl;
$R^{10a}$, $R^{10c}$, $R^{10d}$ and $R^{7g}$ are independently H, halo, $C_{1-6}$ alkyl, $NR_2$, or an optionally substituted phenyl; and
$R^1$, $R^2$, $R^7$, $R^9$ and R are as defined in Formula (1) or (2).

In any of the above Formula (3A), (3B), (3C) or (3D), $R^9$ may be -L-CR($OR^{17}$)—$C_tF_{(2t+1)}$ wherein t is 1-3; -L-S(O)$_2R^{18}$, -L-S(O)$_2NRR^{17}$, -L-S(O)$_2NR(CR_2)_pNR(R^{17})$, -L-S(O)$_2NR(CR_2)_pOR^{17}$ or a radical selected from formula (a), (b), (c) or (d):

(a)
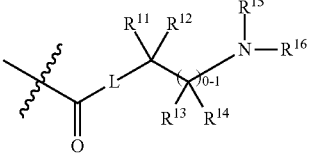

(b)
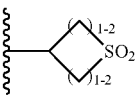

(c)
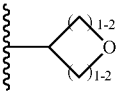

(d)
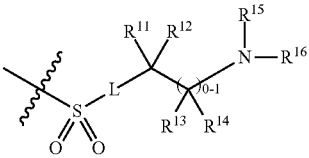

wherein $R^{11}$, $R^{12}$, $R^{13}$, $R^{14}$, $R^{15}$, $R^{16}$, L and p are as defined above; and
$R^{17}$ and $R^{18}$ are independently $C_{1-6}$ alkyl or halo-substituted $C_{1-6}$ alkyl; or $R^{17}$ is H.

In another aspect, the invention provides a compound of Formula (4) or (5):

(4)
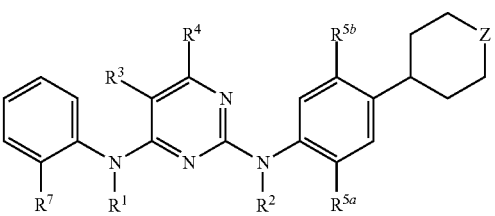

(5)
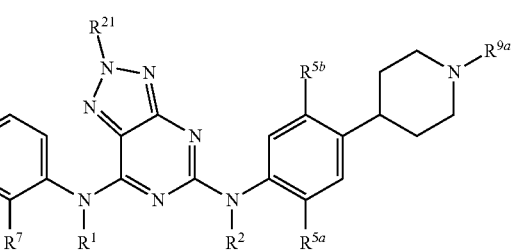

or a physiologically acceptable salt thereof;
Z is $NR^{9a}$ or O;
$R^1$ and $R^2$ are independently H, $C_{1-6}$ alkyl or halo-substituted $C_{1-6}$ alkyl;

$R^3$ and $R^4$ together with the carbon atoms to which they are attached to form a ring selected from the group $R^{5a}$ and $R^{5b}$ are independently halo, hydroxyl, $C_{1-6}$ alkyl, $C_{1-6}$ alkoxy, halo-substituted $C_{1-6}$ alkyl or halo-substituted $C_{1-6}$ alkoxy;

$R^7$ is $S(O)_{0-2}R^{19}$, $S(O)_2NRR^{20}$ or $C(O)NR(R^{20})$; wherein $R^{19}$ and $R^{20}$ are independently $C_{1-6}$ alkyl or halo-substituted $C_{1-6}$ alkyl; or $R^{20}$ is H;

each $R^{9a}$ is independently H, a $C_{1-6}$ alkyl, $C_{2-6}$ alkenyl or $C_{2-6}$ alkynyl; —$(CR_2)_p$—$OR^{17}$, -L-C(O)—$R^{17}$, —C(O)O—$R^{17}$ or -L-C(O)—$NRR^{17}$; wherein R and $R^{17}$ together with N in $NRR^{17}$ may form a 5-6 membered ring optionally containing O or S;

L is $(CR_2)_{1-4}$ or a bond;

$R^{17}$ and $R^{18}$ are independently benzyl, $C_{1-6}$ alkyl optionally substituted with halo, or $C_{3-7}$ cycloalkyl optionally substituted with $C_{1-6}$ alkyl or halo; or $R^{17}$ is H;

$R^{21}$, $R^{22}$, $R^{24}$, $R^{27}$ and $R^{29}$ are independently H or $C_{1-6}$ alkyl;

$R^{23}$, $R^{25}$, $R^{26}$ and $R^{28}$ are independently H, $C_{1-6}$ alkyl, $NR_2$ or halo;

each R is H or $C_{1-6}$ alkyl;

p is 2-4; and provided $R^{22}$ and $R^{23}$ are not both H; $R^{24}$, $R^{25}$ and $R^{26}$ are not all H; and $R^{27}$ and $R^{28}$ are not both H.

In some examples, the invention provides a compound of Formula (4) or (5), wherein $R^{9a}$ is H, a $C_{1-6}$ alkyl, $C_{2-6}$ alkenyl or $C_{2-6}$ alkynyl.

In any of the above Formula (1), (2), (2A), (3), (3A), (3B), (3C), (3D), (4) or (5), $R^1$ and $R^2$ may be H.

In yet another aspect, the invention provides a method of synthesizing a compound having Formula (6) or a pharmaceutically acceptable salt thereof, (6)

wherein W is a 5-6 membered ring containing 1-3 nitrogen atoms;

$R^5$ is $C_{1-6}$ alkyl, $C_{1-6}$ alkoxy, $C_{2-6}$ alkenyl or $C_{2-6}$ alkynyl, each of which may be optionally substituted with halo, amino or hydroxyl groups; halo, nitro, cyano, $CR(OR^{17})R^{17}$, $OR^{17}$, $NR(R^{17})$, $CR(R^{17})NRR^{17}$, $(CR_2)_qY$, $C(O)O_{0-1}R^{17}$, $C(O)NR(R^{17})$, $C(O)CRR^{17}$—$NR(R^{17})$, $C(O)NR(CR_2)_pNR(R^{17})$, $C(O)NR(CR_2)_pOR^{17}$, $C(O)NR(CR_2)_pSR^{17}$, $C(O)NR(CR_2)_pS(O)_{1-2}{}^{18}$, $S(O)_{0-2}R^{18}$, $(CR_2)_{1-6}NR(CR_2)_pOR^{17}$, $(CR_2)_{1-6}NR(CR_2)_qC(O)R^{18}$, $S(O)_2NRR^{17}$, $S(O)_2NR(CR_2)_pNR(R^{17})$, or $S(O)_2NR(CR_2)_pOR^{17}$;

$R^{17}$ and $R^{18}$ are independently $(CR_2)_q Y$ or $C_{1-6}$ alkyl, $C_{2-6}$ alkenyl or $C_{2-6}$ alkynyl, each of which may be optionally substituted with halo, amino, amido, hydroxyl, alkoxy, cyano, carboxyl or Y; or $R^{17}$ is H;

$R^{19}$ is $C_{1-6}$ alkyl;

Y is a $C_{3-12}$ carbocyclic ring, $C_{6-10}$ aryl; or a 5-10 membered heteroaryl or 4-10 membered heterocyclic ring; each of which is optionally substituted with 1-3 $R^5$ groups;

each R is H or $C_{1-6}$ alkyl;

p is 2-4;

q is 0-4;

comprising: a) contacting a reagent of Formula (6a) with a reagent of Formula (6b) or a pharmaceutically acceptable salt thereof, (6a)

(6b)

under conditions sufficient to form an intermediate of Formula (6c);

(6c)

b) contacting said intermediate of Formula (6c) with an oxidizing agent to form an intermediate of Formula (6d);

(6d)

wherein $X^1$ and $X^2$ are a leaving group; and c) contacting said intermediate of Formula (6d) with a reagent of Formula (6e) or a pharmaceutically acceptable salt thereof;

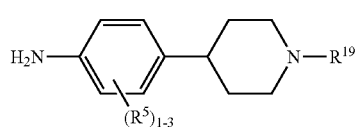
(6e)

under sufficient conditions to form a compound of Formula (6) or a pharmaceutically acceptable salt thereof.

In one embodiment, the invention provides a method of synthesizing a compound of Formula (6f), (6g), (6h) or (6i):

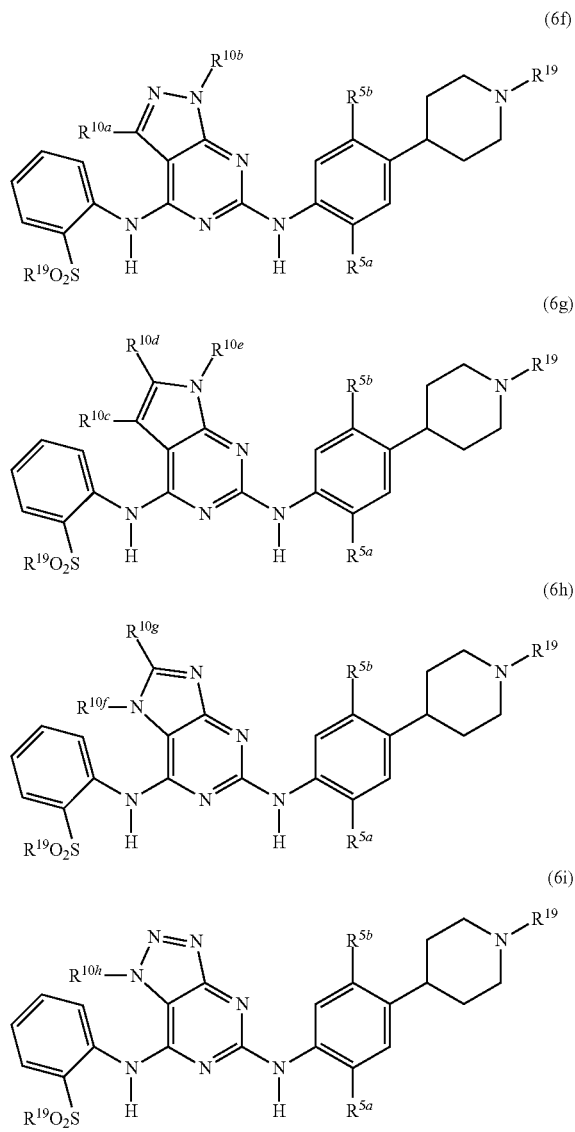

wherein $R^{5a}$ is methoxy or isopropoxy;
$R^{5b}$ is methyl;
$R^{10a}$, $R^{10b}$, $R^{10c}$, $R^{10d}$, $R^{10e}$, $R^{10f}$, $R^{10g}$ and $R^{10h}$ are independently H, halo, $C_{1-6}$ alkyl, $NH_2$, halo, or an optionally substituted phenyl; and
each $R^{19}$ is as defined in Formula (6) above.

In the methods of the invention, the said reagent of Formula (6e) may be synthesized by: i) contacting a reagent of Formula (7) with an alkylating agent to form an intermediate of Formula (8),

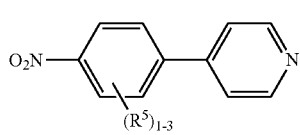
(7)

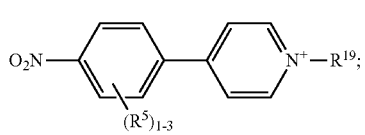
(8)

and ii) reducing said intermediate of Formula (8) to form a reagent of Formula (6e); wherein $R^5$ and $R^{19}$ are as defined in Formula (6) above.

In some examples, the alkylating agent is methyl p-toluenesulfonate. In other examples, the alkylated compound of Formula (6) is reduced by hydrogenation.

In yet another aspect, the present invention provides pharmaceutical compositions comprising a compound having Formula (1), (2), (2A), (3A), (3B), (3C), (3D), (4) or (5), and a physiologically acceptable carrier, and optionally in combination with a second therapeutic agent such as an anti-hyperproliferative agent.

In another aspect, the invention provides methods for inhibiting a kinase selected from Ros, IGF-1R, InsR and anaplastic lymphoma kinase in a cell, comprising contacting the cell with an effective amount of a compound of Formula (1), (2), (2A), (3), (3A), (3B), (3C), (3D), (4) or (5) or a pharmaceutical composition thereof.

The invention also provides methods to treat, ameliorate or prevent a condition, which responds to inhibition of Ros, IGF-1R, InsR or ALK, in a subject suffering therefrom, comprising administering to said subject an effective amount of a compound having Formula (1), (2), (2A), (3A), (3B), (3C), (3D), (4) or (5), or a pharmaceutically acceptable salt or pharmaceutical composition thereof, and optionally in combination with a second therapeutic agent, thereby treating said condition. Alternatively, the present invention provides the use of a compound having (1), (2), (2A), (3A), (3B), (3C), (3D), (4) or (5) in the manufacture of a medicament for treating a condition mediated by Ros, IGF-1R, InsR or ALK. In particular embodiments, the compounds of the invention may be used alone or in combination with a second therapeutic agent to treat a condition mediated by Ros, IGF-1R, InsR or ALK, wherein said condition is an autoimmune disease, a transplantation disease, an infectious disease or a cell proliferative disorder.

Furthermore, the invention provides methods for treating a cell proliferative disorder in a subject suffering therefrom, comprising administering to said subject an effective amount of a compound having (1), (2), (2A), (3A), (3B), (3C), (3D), (4) or (5), or a pharmaceutically acceptable salt or pharmaceutical composition thereof, and optionally in combination with a second therapeutic agent, thereby treating said condition. Alternatively, the present invention provides the use of a compound having (1), (2), (2A), (3A), (3B), (3C), (3D), (4) or (5) in the manufacture of a medicament for treating a cell-proliferative disorder. In particular examples, the compounds of the invention may be used alone or in combination with a chemotherapeutic agent to treat a cell proliferative disorder, including but not limited to, multiple myeloma, neuroblastoma, lymphoma, leukemia, melanoma, sarcoma, osteosarcoma, synovial sarcoma, Ewing's sarcoma, hepatoma, gastrointestinal stromal tumor or a solid tumor of breast, renal, prostate, colorectal, thyroid, ovarian, pancreas, lung, uterus, respiratory tract, brain, digestive tract, urinary tract, eye, liver, skin, head and neck, thyroid or parathyroid.

Definitions

"Alkyl" refers to a moiety and as a structural element of other groups, for example halo-substituted-alkyl and alkoxy, and may be straight-chained or branched. An optionally substituted alkyl, alkenyl or alkynyl as used herein may be optionally halogenated (e.g., $CF_3$), or may have one or more carbons that is substituted or replaced with a heteroatom, such as NR, O or S (e.g., —$OCH_2CH_2O$—, alkylthiols, thioalkoxy, alkylamines, etc).

"Aryl" refers to a monocyclic or fused bicyclic aromatic ring containing carbon atoms. "Arylene" means a divalent radical derived from an aryl group. For example, an aryl group may be phenyl, indenyl, indanyl, naphthyl, or 1,2,3,4-tetrahydronaphthalenyl, which may be optionally substituted in the ortho, meta or para position.

"Heteroaryl" as used herein is as defined for aryl above, where one or more of the ring members is a heteroatom. Examples of heteroaryls include but are not limited to pyridyl, pyrazinyl, indolyl, indazolyl, quinoxalinyl, quinolinyl, benzofuranyl, benzopyranyl, benzothiopyranyl, benzo[1,3]dioxole, imidazolyl, benzo-imidazolyl, pyrimidinyl, furanyl, oxazolyl, isoxazolyl, triazolyl, benzotriazolyl, tetrazolyl, pyrazolyl, thienyl, pyrrolyl, isoquinolinyl, purinyl, thiazolyl, tetrazinyl, benzothiazolyl, oxadiazolyl, benzoxadiazolyl, etc.

A "carbocyclic ring" as used herein refers to a saturated or partially unsaturated, monocyclic, fused bicyclic or bridged polycyclic ring containing carbon atoms, which may optionally be substituted, for example, with =O. Examples of carbocyclic rings include but are not limited to cyclopropyl, cyclobutyl, cyclopentyl, cyclohexyl, cyclopropylene, cyclohexanone, etc.

A "heterocyclic ring" as used herein is as defined for a carbocyclic ring above, wherein one or more ring carbons is a heteroatom. For example, a heterocyclic ring may contain N, O, S, —N=, —S—, —S(O), —$S(O)_2$—, or —NR— wherein R may be hydrogen, $C_{1-4}$alkyl or a protecting group. Examples of heterocyclic rings include but are not limited to morpholino, pyrrolidinyl, pyrrolidinyl-2-one, piperazinyl, piperidinyl, piperidinylone, 1,4-dioxa-8-aza-spiro[4.5]dec-8-yl, 1,2,3,4-tetrahydroquinolinyl, etc. Heterocyclic rings as used herein may encompass bicyclic amines and bicyclic diamines.

As used herein, an H atom in any substituent groups (e.g., $CH_2$) encompasses all suitable isotopic variations, e.g., H, $^2$H and $^3$H.

As used herein a leaving group is an atom (or a group of atoms) that is displaced as a stable species taking with it the bonding electrons. Typically, the leaving group is an anion (e.g. Cl—) or a neutral molecule (e.g. $H_2O$). Suitable leaving groups include, but are not limited to, a halogen, an alkoxy group, an alkylthio group, an aryloxy group, a tosyl group and an arylthio group. Those of skill in the art will know of other leaving groups suitable for use in the present invention.

As used herein, an oxidizing agent is a compound that transfers oxygen atoms. Common oxidizing agents include but are not limited to perchlorates, chlorate, chlorite, hypochlorite, iodine and other halogens, peroxides, sulfoxides, persulfuric acid, hexavalent chromium compounds such as chromic and dichromic acids and chromium trioxide, pyridinium chlorochromate (PCC), and chromate/dichromate compounds, perborates, etc. Those of skill in the art will know of other oxidizing agents suitable for use in the present invention.

As used herein, an alkylating agent is a compound that transfers an alkyl group, and encompasses nucleophilic alkylating agents, electrophilic alkylating agents, radical alkylating agents or carbine alkylating agents.

As used herein, hydrogenation refers to the chemical reaction that results in the addition of hydrogen. Hydrogenation is usually employed to reduce or saturate an unsaturated organic compound. The reaction is typically carried out in the presence of a catalyst, such as platinum group metals; non-catalytic hydrogenation takes place at high temperatures.

Unless otherwise indicated, when a substituent is deemed to be "optionally substituted," it is meant that the substituent is a group that may be substituted with one or more group(s) individually and independently selected from, for example, an optionally halogenated alkyl, alkenyl, alkynyl, alkoxy, alkylamine, alkylthio, alkynyl, amide, amino, including mono- and di-substituted amino groups, aryl, aryloxy, arylthio, carbonyl, carbocyclic, cyano, cycloalkyl, halogen, heteroalkyl, heteroalkenyl, heteroalkynyl, heteroaryl, heterocyclic, hydroxy, isocyanato, isothiocyanato, mercapto, nitro, O-carbamyl, N-carbamyl, O-thiocarbamyl, N-thiocarbamyl, C-amido, N-amido, S-sulfonamido, N-sulfonamido, C-carboxy, O-carboxy, perhaloalkyl, perfluoroalkyl, silyl, sulfonyl, thiocarbonyl, thiocyanato, trihalomethanesulfonyl, and the protected compounds thereof.

The terms "co-administration" or "combined administration" or the like as used herein are meant to encompass administration of the selected therapeutic agents to a single patient, and are intended to include treatment regimens in which the agents are not necessarily administered by the same route of administration or at the same time.

The term "pharmaceutical combination" as used herein refers to a product obtained from mixing or combining active ingredients, and includes both fixed and non-fixed combinations of the active ingredients. The term "fixed combination" means that the active ingredients, e.g. a compound of Formula (1) and a co-agent, are both administered to a patient simultaneously in the form of a single entity or dosage. The term "non-fixed combination" means that the active ingredients, e.g. a compound of Formula (1) and a co-agent, are both administered to a patient as separate entities either simultaneously, concurrently or sequentially with no specific time limits, wherein such administration provides therapeutically effective levels of the active ingredients in the body of the patient. The latter also applies to cocktail therapy, e.g. the administration of three or more active ingredients.

The term "therapeutically effective amount" means the amount of the subject compound that will elicit a biological or medical response in a cell, tissue, organ, system, animal or human that is being sought by the researcher, veterinarian, medical doctor or other clinician.

The term "administration" or "administering" of the subject compound means providing a compound of the invention and prodrugs thereof to a subject in need of treatment.

A "chemotherapeutic agent" is a chemical compound useful in the treatment of cancer. Examples of chemotherapeutic agents include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Agnew, Chem Intl. Ed. Engl., 33: 183-186 (1994)); dynemicin, including dynemicin A; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2''-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhône-Poulenc Rorer, Antony, France); chloranbucil; gemcitabine (GEMZAR®); 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluoromethylornithine (DMFO); retinoids such as retinoic acid; capecitabine (XELODA®); pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

Furthermore, a "chemotherapeutic agent" may include anti-hormonal agents that act to regulate, reduce, block, or inhibit the effects of hormones that can promote the growth of cancer, and are often in the form of systemic, or whole-body treatment. They may be hormones themselves. Examples include anti-estrogens and selective estrogen receptor modulators (SERMs), including, for example, tamoxifen (including NOLVADEX® tamoxifen), EVISTA® raloxifene, droloxifene, 4-hydroxytamoxifen, trioxifene, keoxifene, LY117018, onapristone, and FARESTON® toremifene; anti-progesterones; estrogen receptor down-regulators (ERDs); agents that function to suppress or shut down the ovaries, for example, leutinizing hormone-releasing hormone (LHRH) agonists such as LUPRON® and ELIGARD® leuprolide acetate, goserelin acetate, buserelin acetate and tripterelin; other anti-androgens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole. In addition, such definition of chemotherapeutic agents includes bisphosphonates such as clodronate (for example, BONEFOS® or OSTAC®), DIDROCAL® etidronate, NE-58095, ZOMETA® zoledronic acid/zoledronate, FOSAMAX® alendronate, AREDIA® pamidronate, SKELID® tiludronate, or ACTONEL® risedronate; as well as troxacitabine (a 1,3-dioxolane nucleoside cytosine analog); antisense oligonucleotides, particularly those that inhibit expression of genes in signaling pathways implicated in abherant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; LURTOTECAN® topoisomerase 1 inhibitor; ABARELIX® rmRH; lapatinib ditosylate (an ErbB-2 and EGFR dual tyrosine kinase small-molecule inhibitor also known as GW572016); and pharmaceutically acceptable salts, acids or derivatives of any of the above.

MODES OF CARRYING OUT THE INVENTION

The invention provides novel pyrimidine derivatives and pharmaceutical compositions thereof, and methods for using such compounds.

In one aspect, the invention provides a compound of Formula (1) or (2):

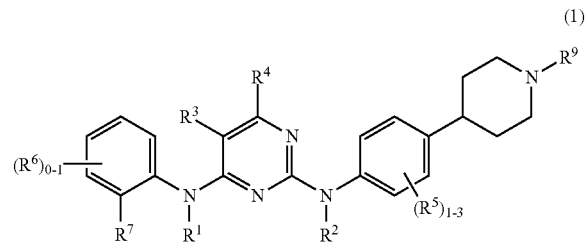
(1)

-continued (2)

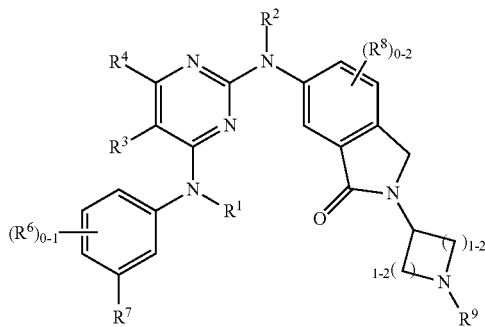

or a physiologically acceptable salt thereof;

$R^1$ and $R^2$ are independently H, $C_{1-6}$ alkyl or halo-substituted $C_{1-6}$ alkyl;

$R^3$ is halo, $C_{1-6}$ alkyl, or a halo-substituted $C_{1-6}$ alkyl; $R^4$ is H;

alternatively, $R^3$ and $R^4$ together with the carbon atoms to which they are attached to may form a 5-6 membered ring containing 1-3 heteroatoms selected from N, O and S, and optionally substituted with 1-2 $R^{10}$ groups wherein $R^{10}$ is halo, $C_{1-6}$ alkyl, $C_{2-6}$ alkenyl, $C_{2-6}$ alkynyl, optionally substituted phenyl or $NR_2$;

$R^5$, $R^6$ and $R^8$ are independently $C_{1-6}$ alkyl, $C_{1-6}$ alkoxy, $C_{2-6}$ alkenyl or $C_{2-6}$ alkynyl, each of which may be optionally substituted with halo, amino or hydroxyl groups; halo, nitro, cyano, $CR(OR^{17})R^{17}$, $OR^{17}$, $NR(R^{17})$, $CR(R^{17})NRR^{17}$, $(CR_2)_qY$, $C(O)O_{0-1}R^{17}$, $C(O)NR(R^{17})$, $C(O)CRR^{17}$—$NR(R^{17})$, $C(O)NR(CR_2)_pNR(R^{17})$, $C(O)NR(CR_2)_pOR^{17}$, $C(O)NR(CR_2)_pSR^{17}$, $C(O)NR(CR_2)_pS(O)_{1-2}R^{18}$, $S(O)_{0-2}R^{18}$, $(CR_2)_{1-6}NR(CR_2)_pOR^{17}$, $(CR_2)_{1-6}NR(CR_2)_qC(O)R^{18}$, $S(O)_2NRR^{17}$, $S(O)_2NR(CR_2)_pNR(R^{17})$, or $S(O)_2NR(CR_2)_pOR^{17}$; wherein $R^8$ may be on any position of the fused ring;

$R^7$ is $S(O)_{0-2}R^{19}$, $S(O)_2NRR^{20}$ or $C(O)NR(R^{20})$; wherein $R^{19}$ and $R^{20}$ are independently $C_{1-6}$ alkyl, halo-substituted $C_{1-6}$ alkyl or $C_{3-7}$ cycloalkyl; or $R^{20}$ is H;

each $R^9$ is independently -L-CR(OR$^{17}$)—$C_tF_{(2t+1)}$ wherein t is 1-3; -L-C(O)—CR(R$^{17}$)—NRR$^{17}$, -L-C(O)—NR—(CR$_2)_p$—NRR$^{17}$, -L-C(O)NR(CR$_2)_p$OR$^{17}$, -L-C(O)—(CR$_2)_q$—NR—C(O)—R$^{18}$, -L-C(O)NR(CR$_2)_p$SR$^{17}$, -L-C(O)NR(CR$_2)_p$S(O)$_{1-2}$R$^{18}$, (CR$_2)_p$NR(CR$_2)_p$OR$^{17}$ or (CR$_2)_p$NR-L-C(O)R$^{18}$, -L-S(O)$_2$R$^{18}$, -L-S(O)$_2$NRR$^{17}$, -L-S(O)$_2$NR(CR$_2)_p$NR(R$^{17}$), -L-S(O)$_2$NR(CR$_2)_p$OR$^{17}$ or a radical selected from formula (a), (b), (c) or (d):

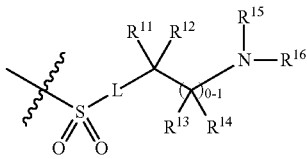

(a)

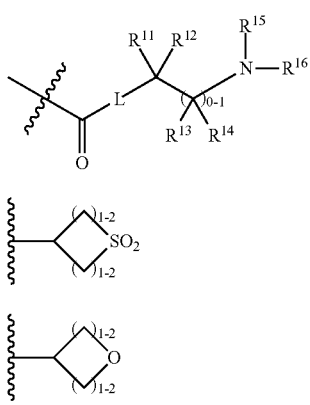

(b)

(c)

-continued (d)

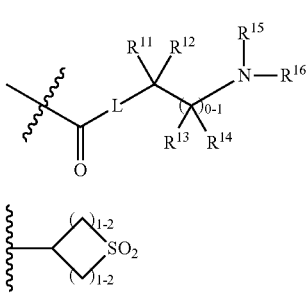

wherein $R^{11}$, $R^{12}$, $R^{13}$, $R^{14}$, $R^{15}$ and $R^{16}$ are independently selected from H, or $C_{1-6}$ alkyl, $C_{1-6}$ alkoxy, $C_{2-6}$ alkenyl or $C_{2-6}$ alkynyl, each of which may be optionally substituted with halo, amino or hydroxyl groups; or $R^{11}$ and $R^{12}$, $R^{12}$ and $R^{15}$, $R^{15}$ and $R^{16}$, $R^{13}$ and $R^{14}$, or $R^{13}$ and $R^{15}$ together with the carbon and/or nitrogen atoms to which they are attached may form a 3-7 membered saturated, unsaturated or partially unsaturated ring optionally containing up to 3 atoms or groups selected from C(O), N, O and $S(O)_{0-2}$;

L is $(CR_2)_{1-4}$ or a bond;

$R^{17}$ and $R^{18}$ are independently $C_{1-6}$ alkyl, halo-substituted $C_{1-6}$ alkyl, $C_{2-6}$ alkenyl or $C_{2-6}$ alkynyl; or $R^{17}$ is H;

Y is a $C_{3-12}$ carbocyclic ring, $C_{6-10}$ aryl; or a 5-10 membered heteroaryl or 4-10 membered heterocyclic ring; each of which is optionally substituted with 1-3 $R^6$ groups;

each R is H or $C_{1-6}$ alkyl;

p is 2-4; and q is 0-4.

In one embodiment, the invention provides a compound of Formula (2A):

(2A)

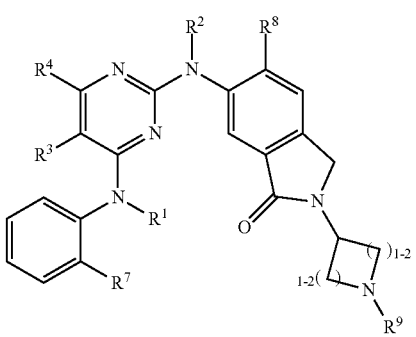

wherein $R^3$ is halo;

$R^7$ is $S(O)_{0-2}R^{19}$;

$R^8$ is methoxy, ethoxy or isopropoxy;

$R^9$ is -L-CR(OR$^{17}$)—$C_tF_{(2t+1)}$ wherein t is 1-3; -L-S(O)$_2$R$^{18}$, -L-S(O)$_2$NRR$^{17}$, -L-S(O)$_2$NR(CR$_2)_p$NR(R$^{17}$), -L-S(O)$_2$NR(CR$_2)_p$OR$^{17}$ or a radical selected from formula (a), (b), (c) or (d):

(a)

(b)

-continued

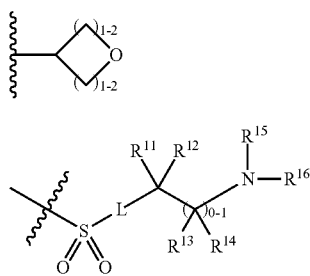
(c)

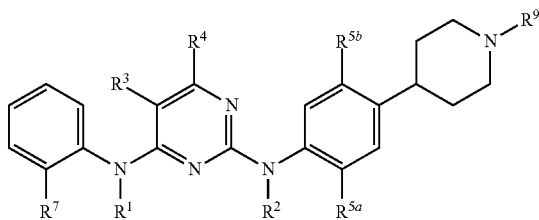
(d)

wherein $R^1$, $R^2$, $R^4$, $R^{11}$, $R^{12}$, $R^{13}$, $R^{14}$, $R^{15}$, $R^{16}$, $R^{17}$, $R^{18}$, $R^{19}$, L and p are as defined in Formula (1) or (2).

In some examples, the invention provides a compound of Formula (3):

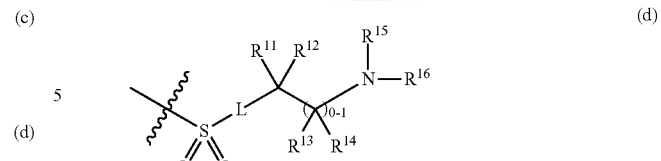
(3)

wherein $R^3$ is halo;
alternatively, $R^3$ and $R^4$ together with the carbon atoms to which they are attached to may form a 5-6 membered ring containing 1-3 N heteroatoms, and optionally substituted with 1-2 $R^{10}$ groups;
$R^{5a}$ and $R^{5b}$ are independently halo, hydroxyl, $C_{1-6}$ alkyl, $C_{1-6}$ alkoxy, halo-substituted $C_{1-6}$ alkyl or halo-substituted $C_{1-6}$ alkoxy;
$R^7$ is $S(O)_{0-2}R^{19}$;
$R^1$, $R^2$, $R^9$, $R^{10}$ and $R^{19}$ are as defined in Formula (1) or (2).

In particular embodiments in the above Formula (3), $R^{5a}$ is methoxy or isopropoxy;
$R^{5b}$ is or methyl;
$R^9$ is -L-CR(OR$^{17}$)—C$_t$F$_{(2t+1)}$ wherein t is 1-3; -L-S(O)$_2$R$^{18}$, -L-S(O)$_2$NRR$^{17}$, -L-S(O)$_2$NR(CR$_2$)$_p$NR(R$^{17}$), -L-S(O)$_2$NR(CR$_2$)$_p$OR$^{17}$ or a radical selected from formula (a), (b), (c) or (d):

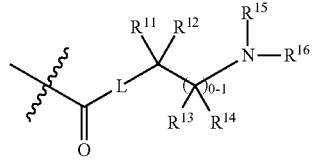
(a)

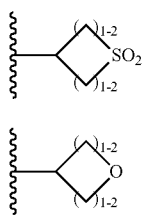
(b)

(c)

(d)

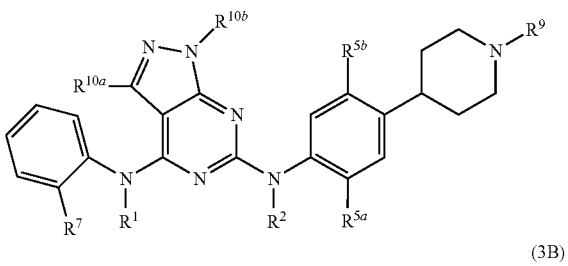
(d)

wherein $R^{11}$, $R^{12}$, $R^{13}$, $R^{14}$, $R^{15}$, $R^{16}$, $R^{17}$, $R^{18}$, L and p are as defined in Formula (1) or (2).

In other particular embodiments, the invention provides a compound of Formula (3A), (3B), (3C) or (3D):

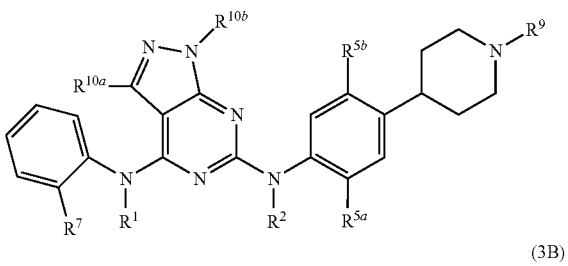
(3A)

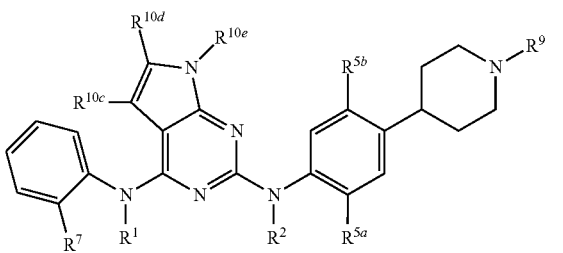
(3B)

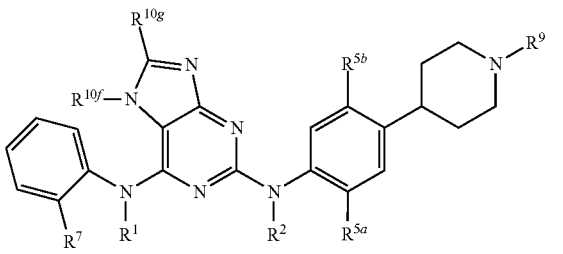
(3C)

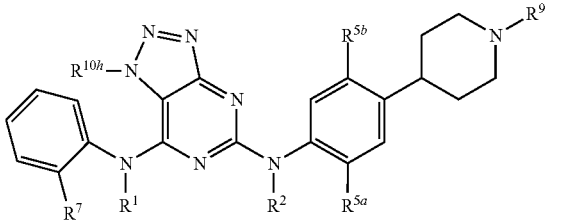
(3D)

wherein $R^{5a}$ is methoxy or isopropoxy;
$R^{5b}$ is methyl;
$R^{10b}$, $R^{10e}$, $R^{10f}$ and $R^{10h}$ are independently H or $C_{1-6}$ alkyl;
$R^{10a}$, $R^{10c}$, $R^{10d}$ and $R^{7g}$ are independently H, halo, $C_{1-6}$ alkyl, NR$_2$, or an optionally substituted phenyl; and
$R^1$, $R^2$, $R^7$, $R^9$ and R are as defined in Formula (1) or (2).

In any of the above Formula (3A), (3B), (3C) or (3D), $R^9$ may be -L-CR(OR$^{17}$)—C$_t$F$_{(2t+1)}$ wherein t is 1-3; -L-

S(O)$_2$R$^{18}$, -L-S(O)$_2$NRR$^{17}$, -L-S(O)$_2$NR(CR$_2$)$_p$NR(R$^{17}$), -L-S(O)$_2$NR(CR$_2$)$_p$OR$^{17}$ or a radical selected from formula (a), (b), (c) or (d):

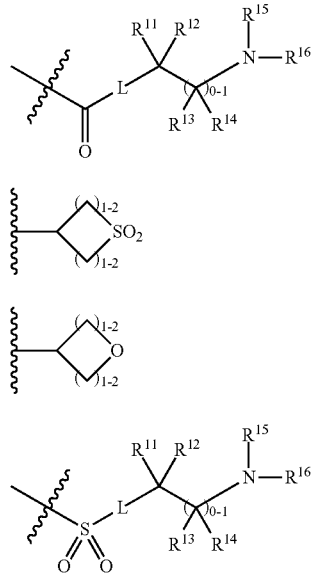

wherein R$^{11}$, R$^{12}$, R$^{13}$, R$^{14}$, R$^{15}$, R$^{16}$, L and p are as defined above; and R$^{17}$ and R$^{18}$ are independently C$_{1-6}$ alkyl or halo-substituted C$_{1-6}$ alkyl; or R$^{17}$ is H.

In another aspect, the invention provides a compound of Formula (4) or (5):

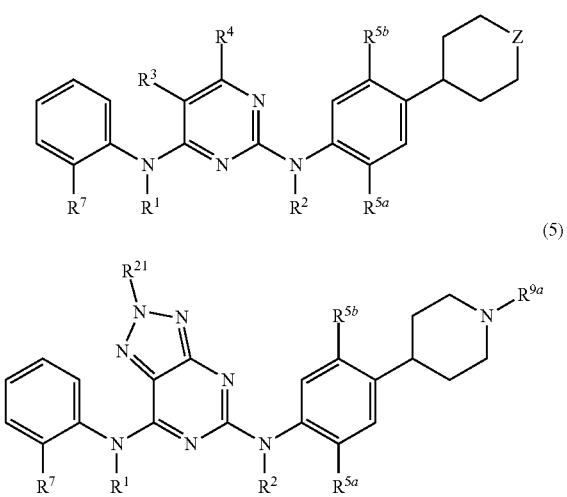

or a physiologically acceptable salt thereof;

Z is NR$^{9a}$ or O;

R$^1$ and R$^2$ are independently H, C$_{1-6}$ alkyl or halo-substituted C$_{1-6}$ alkyl;

R$^3$ and R$^4$ together with the carbon atoms to which they are attached to form a ring selected from the group R$^{5a}$ and R$^{5b}$ are independently halo, hydroxyl, C$_{1-6}$ alkyl, C$_{1-6}$ alkoxy, halo-substituted C$_{1-6}$ alkyl or halo-substituted C$_{1-6}$ alkoxy;

R$^7$ is S(O)$_{0-2}$R$^{19}$, S(O)$_2$NRR$^{20}$ or C(O)NR(R$^{20}$); wherein R$^{19}$ and R$^{20}$ are independently C$_{1-6}$ alkyl or halo-substituted C$_{1-6}$ alkyl; or R$^{20}$ is H;

each R$^{9a}$ is independently H, a C$_{1-6}$ alkyl, C$_{2-6}$ alkenyl or C$_{2-6}$ alkynyl; —(CR$_2$)$_p$—OR$^{17}$, -L-C(O)—R$^{17}$, —C(O)O—R$^{17}$ or -L-C(O)—NRR$^{17}$; wherein R and R$^{17}$ together with N in NRR$^{17}$ may form a 5-6 membered ring optionally containing O or S;

L is (CR$_2$)$_{1-4}$ or a bond;

R$^{17}$ and R$^{18}$ are independently benzyl, C$_{1-6}$ alkyl optionally substituted with halo, or C$_{3-7}$ cycloalkyl optionally substituted with C$_{1-6}$ alkyl or halo; or R$^{17}$ is H;

R$^{21}$, R$^{22}$, R$^{24}$, R$^{27}$ and R$^{29}$ are independently H or C$_{1-6}$ alkyl;

R$^{23}$, R$^{25}$, R$^{26}$ and R$^{28}$ are independently H, C$_{1-6}$ alkyl, NR$_2$ or halo;

each R is H or C$_{1-6}$ alkyl;

p is 2-4; and provided R$^{22}$ and R$^{23}$ are not both H; R$^{24}$, R$^{25}$ and R$^{26}$ are not all H; and R$^{27}$ and R$^{28}$ are not both H.

In yet another aspect, the invention provides a method of synthesizing a compound having Formula (6) or a pharmaceutically acceptable salt thereof,

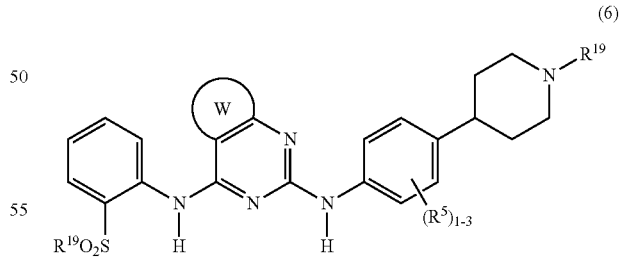

wherein W is a 5-6 membered ring containing 1-3 nitrogen atoms;

R$^5$ is C$_{1-6}$ alkyl, C$_{1-6}$ alkoxy, C$_{2-6}$ alkenyl or C$_{2-6}$ alkynyl, each of which may be optionally substituted with halo, amino or hydroxyl groups; halo, nitro, cyano, CR(OR$^{17}$)R$^{17}$, OR$^{17}$, NR(R$^{17}$), CR(R$^{17}$)NRR$^{17}$, (CR$_2$)$_q$Y, C(O)O$_{0-1}$R$^{17}$, C(O)NR (R$^{17}$), C(O)CRR$^{17}$—NR(R$^{17}$), C(O)NR(CR$_2$)$_p$NR(R$^{17}$), C(O)NR(CR$_2$)$_p$OR$^{17}$, C(O)NR(CR$_2$)$_p$SR$^{17}$, C(O)NR(CR$_2$)$_p$S(O)$_{1-2}$R$^{18}$, S(O)$_{0-2}$R$^{18}$, (CR$_2$)$_{1-6}$NR(CR$_2$)$_p$OR$^{17}$, (CR$_2$)$_{1-6}$ $NR(CR_2)_qC(O)R^{18}$, $S(O)_2NRR^{17}$, $S(O)_2NR(CR_2)_pNR(R^{17})$, or $S(O)_2NR(CR_2)_pOR^{17}$;

$R^{17}$ and $R^{18}$ are independently $(CR_2)_qY$ or $C_{1-6}$ alkyl, $C_{2-6}$ alkenyl or $C_{2-6}$ alkynyl, each of which may be optionally substituted with halo, amino, amido, hydroxyl, alkoxy, cyano, carboxyl or Y; or $R^{17}$ is H;

$R^{19}$ is $C_{1-6}$ alkyl;

Y is a $C_{3-12}$ carbocyclic ring, $C_{6-10}$ aryl; or a 5-10 membered heteroaryl or 4-10 membered heterocyclic ring; each of which is optionally substituted with 1-3 $R^5$ groups;

each R is H or $C_{1-6}$ alkyl;

p is 2-4;

q is 0-4;

comprising: a) contacting a reagent of Formula (6a) with a reagent of Formula (6b) or a pharmaceutically acceptable salt thereof,

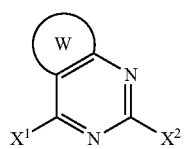

(6a)

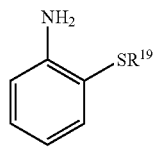

(6b)

under conditions sufficient to form an intermediate of Formula (6c);

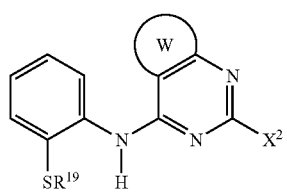

(6c)

b) contacting said intermediate of Formula (6c) with an oxidizing agent to form an intermediate of Formula (6d);

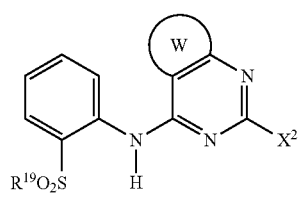

(6d)

wherein $X^1$ and $X^2$ are a leaving group; and c) contacting said intermediate of Formula (6d) with a reagent of Formula (6e) or a pharmaceutically acceptable salt thereof;

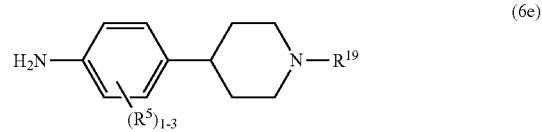

(6e)

under sufficient conditions to form a compound of Formula (6) or a pharmaceutically acceptable salt thereof.

In one embodiment, the invention provides a method of synthesizing a compound of Formula (6f), (6g), (6h) or (6i):

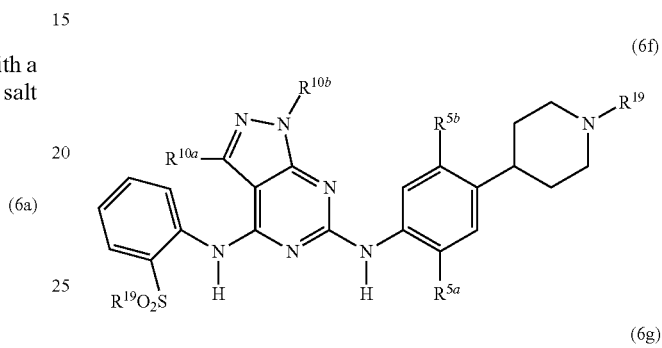

(6f)

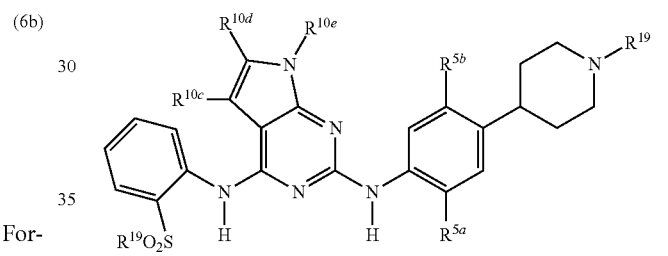

(6g)

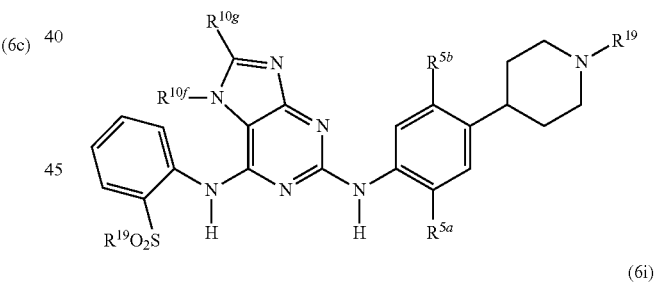

(6h)

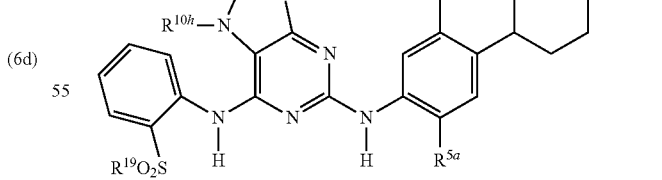

(6i)

wherein $R^{5a}$ is methoxy or isopropoxy;

$R^{5b}$ is methyl;

$R^{10a}$, $R^{10b}$, $R^{10c}$, $R^{10d}$, $R^{10e}$, $R^{10f}$, $R^{10g}$ and $R^{10h}$ are independently H, halo, $C_{1-6}$ alkyl, $NH_2$, halo, or an optionally substituted phenyl; and each $R^{19}$ is as defined in Formula (6) above.

In yet another aspect, the invention provides a compound of Formula (9) or (10):

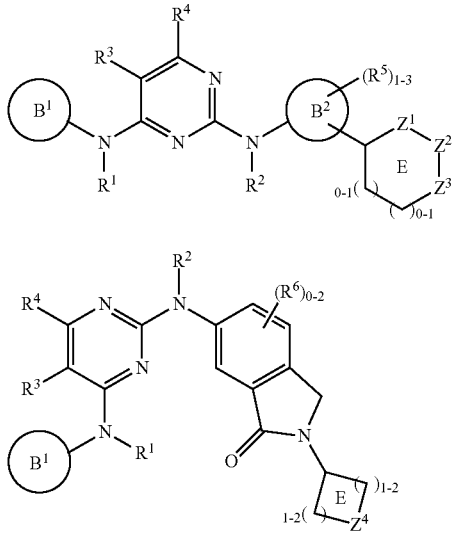

(9)

(10)

or a pharmaceutically acceptable salt thereof;

$B^1$ is an aryl substituted with 1-3 $R^7$ groups or a heteroaryl optionally substituted with 1-3 $R^7$ groups;

$B^2$ is an aryl or heteroaryl;

ring E may optionally contain a double bond;

one of $Z^1$, $Z^2$ and $Z^3$ is O, $SO_{0-2}$, $NR^8$ or $NR^9$ and the others are $CR_2$;

$Z^4$ is $NR^8$ or $NR^9$;

$R^1$ and $R^2$ are independently H, $C(O)R^{10}$, $C_{1-6}$ alkyl or halo-substituted $C_{1-6}$ alkyl;

$R^3$ and $R^4$ are independently halo, $OR^{17}$, $NR(R^{17})$, $SR^{17}$; $C_{1-6}$ alkyl, $C_{1-6}$ alkoxy, $C_{2-6}$ alkenyl or $C_{2-6}$ alkynyl, each of which may be optionally substituted with halo, amino or hydroxyl groups; $C(O)R^{17}$, $NC(O)R^{18}$, $C(O)NRR^{17}$, $S(O)_2NRR^{17}$, $NS(O)_2R^{18}$, $S(O)_{0-2}R^{18}$; or an optionally substituted $C_{3-12}$ carbocyclic ring, $C_{6-10}$ aryl; or a 5-10 membered heteroaryl or heterocyclic ring containing 1-4 heteroatoms selected from N, O and S;

alternatively, one of $R^3$ and $R^4$ is H, or $R^3$ and $R^4$ together with the carbon atoms to which they are attached to may form a 9-12 membered ring optionally substituted with 1-2 $R^7$ groups and optionally containing 1-3 N heteroatoms selected from N, O and S;

$R^5$, $R^6$ and $R^7$ are independently $C_{1-6}$ alkyl, $C_{1-6}$ alkoxy, $C_{2-6}$ alkenyl or $C_{2-6}$ alkynyl, each of which may be optionally substituted with halo, amino or hydroxyl groups; halo, nitro, cyano, $CR(OR^{17})R^{17}$, $OR^{17}$, $NR(R^{17})$, $CR(R^{17})NRR^{17}$, $(CR_2)_qY$, $C(O)O_{0-1}R^{17}$, $C(O)NR(R^{17})$, $C(O)CRR^{17}$—NR$(R^{17})$, $C(O)NR(CR_2)_pNR(R^{17})$, $C(O)NR(CR_2)_pOR^{17}$, $C(O)NR(CR_2)_pSR^{17}$, $C(O)NR(CR_2)_pS(O)_{1-2}R^{18}$, $S(O)_{0-2}R^{18}$, $(CR_2)_{1-6}NR(CR_2)_pOR^{17}$, $(CR_2)_{1-6}NR(CR_2)_qC(O)R^{18}$, $S(O)_2NRR^{17}$, $S(O)_2NR(CR_2)_pNR(R^{17})$, or $S(O)_2NR(CR_2)_pOR^{17}$; wherein $R^6$ may be on any position of the fused ring;

$R^8$ is H, a $C_{1-6}$ alkyl, $C_{2-6}$ alkenyl or $C_{2-6}$ alkynyl, each of which may be optionally substituted with halo, amino or hydroxyl groups; halo, nitro or cyano; —$CR(OR^{17})R^{17}$, —$(CR_2)_p$—$OR^{17}$, $(CR_2)_p$—$NR(R^{17})$, -L-$CR(R^{17})NRR^{17}$, -L-Y, -L-C(O)—$R^{17}$, —$(CR_2)_{1-4}$—$C(O)O$—$R^{17}$ or -L-C(O)—$NRR^{17}$;

$R^9$ is -L-$CR(OR^{17})$—$C_tF_{(2t+1)}$ wherein t is 1-3; -L-C(O)—$CR(R^{17})$—$NRR^{17}$, -L-C(O)—NR—$(CR_2)_p$—$NRR^{17}$, -L-C(O)$NR(CR_2)_pOR^{17}$, -L-C(O)—$(CR_2)_q$—NR—C(O)—$R^{18}$, -L-C(O)$NR(CR_2)_pSR^{17}$, -L-C(O)$NR(CR_2)_pS(O)_{1-2}R^{18}$, $(CR_2)_pNR(CR_2)_pOR^{17}$ or $(CR_2)_pNR$-L-$C(O)R^{18}$, -L-$S(O)_2R^{18}$, -L-$S(O)_2NRR^{17}$, -L-$S(O)_2NR(CR_2)_pNR(R^{17})$, -L-$S(O)_2NR(CR_2)_pOR^{17}$ or a radical selected from formula (a), (b), (c) or (d):

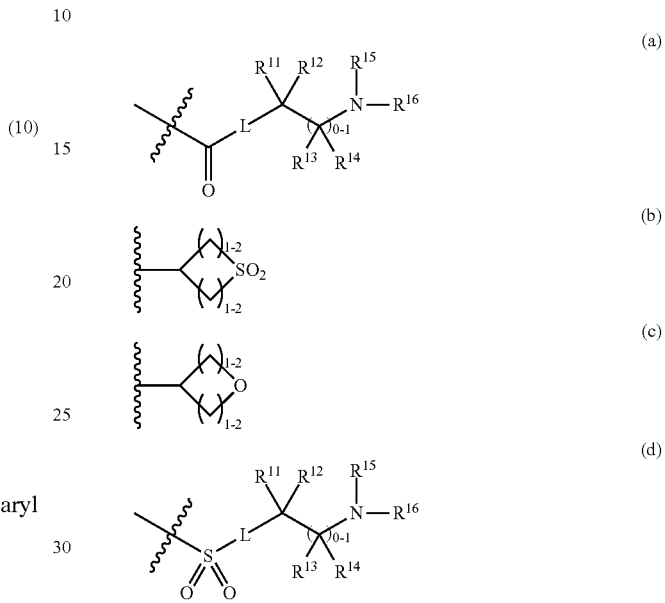

(a)

(b)

(c)

(d)

wherein $R^{11}$, $R^{12}$, $R^{13}$, $R^{14}$, $R^{15}$ and $R^{16}$ are independently selected from H, or $C_{1-6}$ alkyl, $C_{1-6}$ alkoxy, $C_{2-6}$ alkenyl or $C_{2-6}$ alkynyl, each of which may be optionally substituted with halo, amino or hydroxyl groups; or $R^{11}$ and $R^{12}$, $R^{12}$ and $R^{15}$, $R^{15}$ and $R^{16}$, $R^{13}$ and $R^{14}$, or $R^{13}$ and $R^{15}$ together with the carbon and/or nitrogen atoms to which they are attached may form a 3-7 membered saturated, unsaturated or partially unsaturated ring optionally containing up to 3 atoms or groups selected from C(O), N, O and $S(O)_{0-2}$;

L is $(CR_2)_{1-4}$ or a bond;

$R^{10}$, $R^{17}$ and $R^{18}$ are independently $(CR_2)_qY$ or $C_{1-6}$ alkyl, $C_{2-6}$ alkenyl or $C_{2-6}$ alkynyl, each of which may be optionally substituted with halo, amino, amido, hydroxyl, alkoxy, cyano, carboxyl or Y; or $R^{17}$ is H;

Y is a $C_{3-12}$ carbocyclic ring, $C_{6-10}$ aryl; or a 5-10 membered heteroaryl or 4-10 membered heterocyclic ring; each of which is optionally substituted with 1-3 $R^7$ groups;

each R is H or $C_{1-6}$ alkyl;

p is 2-4;

q is 0-4;

provided $Z^4$ and one of $Z^1$, $Z^2$ and $Z^3$ is $NR^9$ when one of $R^3$ and $R^4$ is halo, $OR^{17}$, $NR(R^{17})$, $SR^{17}$; $C_{1-6}$ alkyl, $C_{1-6}$ alkoxy, $C_{2-6}$ alkenyl or $C_{2-6}$ alkynyl, each of which may be optionally substituted with halo, amino or hydroxyl groups; or when $R^3$ and $R^4$ together form phenyl, pyridyl, piperidyl or

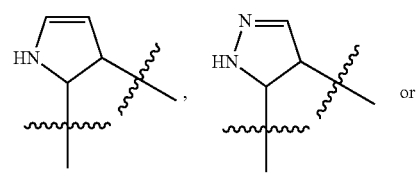

or

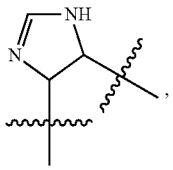

or tautomers thereof; and further provided that $R^3$ and $R^4$ together with the carbon atoms to which they are attached to form a ring when $B^1$ is a heteroaryl.

In each of the above formula, any asymmetric carbon atoms may be present in the (R)-, (S)-or (R,S)-configuration. The compounds may thus be present as mixtures of isomers or as pure isomers, for example, as pure enantiomers or diastereomers. The invention further encompasses possible tautomers of the inventive compounds.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2$H, $^3$H, $^{11}$C, $^{13}$C, $^{14}$C, $^{15}$N, $^{18}$F $^{31}$P, $^{32}$P, $^{35}$S, $^{36}$Cl, $^{125}$I respectively.

The invention includes various isotopically labeled compounds as defined herein, for example, those into which radioactive isotopes such as $^3$H, $^{13}$C, and $^{14}$C , are present. Such isotopically labelled compounds are useful in metabolic studies (with, for example, $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In other examples, an $^{18}$F or labeled compound may be used for PET or SPECT studies. Isotopic variations of the compounds have the potential to change a compound's metabolic fate and/or create small changes in physical properties such as hydrophobicity, and the like. Isotopic variations also have the potential to enhance efficacy and safety, enhance bioavailability and half-life, alter protein binding, change biodistribution, increase the proportion of active metabolites and/or decrease the formation of reactive or toxic metabolites. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

In each of the above formula, each optionally substituted moiety may be substituted with $C_{1-6}$ alkyl, $C_{2-6}$ alkenyl or $C_{3-6}$ alkynyl, each of which may be optionally halogenated or optionally having a carbon that may be replaced or substituted with N, S, O, or a combination thereof (for example, hydroxyl $C_{1-8}$alkyl, $C_{1-8}$alkoxyl $C_{1-8}$alkyl); halo, amino, amidino, $C_{1-6}$ alkoxy; hydroxyl, methylenedioxy, carboxy; $C_{1-8}$ alkylcarbonyl; $C_{1-8}$ alkoxycarbonyl, carbamoyl, $C_{1-8}$ alkylcarbamoyl, sulfamoyl, cyano, oxo, nitro, or an optionally substituted carbocyclic ring, heterocyclic ring, aryl or heteroaryl as previously described.

Pharmacology and Utility

The compounds of the invention and their pharmaceutically acceptable salts exhibit valuable pharmacological properties when tested in vitro in cell-free kinase assays and in cellular assays, and are therefore useful as pharmaceuticals.

In one aspect, compounds of (1), (2), (2A), (3A), (3B), (3C), (3D), (4) or (5) may inhibit the tyrosine kinase activity of anaplastic lymphoma kinase (ALK) and the fusion protein of NPM-ALK. This protein tyrosine kinase results from a gene fusion of nucleophosmin (NPM) and ALK, rendering the protein tyrosine kinase activity of ALK ligand independent. NPM-ALK plays a key role in signal transmission in a number of hematopoetic and other human cells leading to hematological and neoplastic diseases, for example in anaplastic large-cell lymphoma (ALCL) and non-Hodgkin's lymphomas (NHL), specifically in ALK+NHL or Alkomas, in inflammatory myofibroblastic tumors (IMT) and neuroblastomas. (Duyster et al. 2001 Oncogene 20, 5623-5637). In addition to NPM-ALK, other gene fusions have been identified in human hematological and neoplastic diseases; for example, TPM3-ALK (a fusion of nonmuscle tropomyosin with ALK).

The inhibition of ALK tyrosine kinase activity may be demonstrated using known methods, for example using the recombinant kinase domain of the ALK in analogy to the VEGF-R kinase assay described in J. Wood et al. Cancer Res. 60, 2178-2189 (2000). In general, in vitro enzyme assays using GST-ALK protein tyrosine kinase are performed in 96-well plates as a filter binding assay in 20 mM Tris HCl, pH=7.5, 3 mM MgCl$_2$, 10 mM MnCl$_2$, 1 mM DTT, 0.1 μCi/assay (=30 μl) [γ-$^{33}$P]-ATP, 2 μM ATP, 3 μg/mL poly (Glu, Tyr 4:1) Poly-EY (Sigma P-0275), 1% DMSO, 25 ng ALK enzyme. Assays are incubated for 10 min at ambient temperature. Reactions are terminated by adding 50 μl of 125 mM EDTA, and the reaction mixture is transferred onto a MAIP Multiscreen plate (Millipore, Bedford, Mass., USA), previously wet with methanol, and rehydrated for 5 min with H$_2$O. Following washing (0.5% H$_3$PO$_4$), plates are counted in a liquid scintillation counter. IC$_{50}$ values are calculated by linear regression analysis of the percentage inhibition.

Compounds of (1), (2), (2A), (3A), (3B), (3C), (3D), (4) or (5) may potently inhibit the growth of human NPM-ALK overexpressing murine BaF3 cells (DSMZ Deutsche Sammiung von Mikroorganismen and Zelikulturen GmbH, Germany). The expression of NPM-ALK may be achieved by transfecting the BaF3 cell line with an expression vector pClneo™ (Promega Corp., Madison Wis., USA) coding for NPM-ALK and subsequent selection of G418 resistant cells. Non-transfected BaF3 cells depend on IL-3 for cell survival. In contrast, NPM-ALK expressing BaF3 cells (named BaF3-NPM-ALK hereinafter) can proliferate in the absence of IL-3 because they obtain proliferative signal through NPM-ALK kinase. Putative inhibitors of the NPM-ALK kinase therefore abolish the growth signal and may result in antiproliferative activity. The antiproliferative activity of putative inhibitors of the NPM-ALK kinase can however be overcome by addition of IL-3, which provides growth signals through an NPM-ALK independent mechanism. An analogous cell system using FLT3 kinase has also been described (see, E Weisberg et al. Cancer Cell; 1, 433-443 (2002)).

The inhibitory activity of the compounds of the invention may be determined as follows. In general, BaF3-NPM-ALK cells (15,000/microtitre plate well) are transferred to 96-well microtitre plates. Test compounds dissolved in dimethyl sulfoxide (DMSO) are added in a series of concentrations (dilution series) in such a manner that the final concentration of DMSO is not greater than 1% (v/v). After the addition, the plates are incubated for two days during which the control cultures without test compound are able to undergo two cell-division cycles. The growth of the BaF3-NPM-ALK cells is measured by means of YOPRO™ staining [T Idziorek et al. J. Immunol. Methods; 185: 249-258 (1995)]: 25 μl of lysis buffer comprising 20 mM sodium citrate, pH 4.0, 26.8 mM sodium chloride, 0.4% NP40, 20 mM EDTA and 20 mM is added to each well. Cell lysis is completed within 60 min at room temperature and total amount of YOPRO™ bound to DNA is determined by measurement using the Cytofluor II 96-well reader (PerSeptive Biosystems) with the following settings: Excitation (nm) 485/20 and Emission (nm) 530/25.

IC$_{50}$ values may be determined by a computer-aided system using the formula:

IC$_{50}$=[(ABS$_{test}$−ABS$_{start}$)/(ABS$_{control}$−ABS$_{start}$)]× 100. (ABS=absorption)

The IC$_{50}$ value in those experiments is given as that concentration of the test compound in question that results in a cell count that is 50% lower than that obtained using the control without inhibitor. The compounds of the invention in free form or in pharmaceutically acceptable salt form, may exhibit valuable pharmacological properties, for example, as indicated by the in vitro tests described in this application. In general, compounds of the invention have IC$_{50}$ values from 1 nM to 10 µM. In some examples, compounds of the invention have IC$_{50}$ values from 1 nM to 5 µM, or more particularly from 1 nM to 1 µM. In yet other examples, compounds of the invention have IC$_{50}$ values of less than 1 nM or more than 10 µM. The compounds of the invention may exhibit a percentage inhibition of greater than 50%, or in other embodiments, may exhibit a percentage inhibition greater than about 70%, against ALK at 10 µM.

The antiproliferative action of the inventive compounds may also be determined in the human KARPAS-299 lymphoma cell line (DSMZ Deutsche Sammiung von Mikroorganismen and Zelikulturen GmbH, Braunschweig, Germany, described in WG Dirks et al. Int. J. Cancer 100, 49-56 (2002)) using the same methodology described above for the BaF3-NPM-ALK cell line. In some embodiments, compounds of the invention may exhibit inhibitory activity with an IC$_{50}$ in the range from approximately 0.01 to 1 µM. The action of the inventive compounds on autophosphorylation of the ALK may be determined in the human KARPAS-299 lymphoma cell line by means of an immunoblot as described in WG Dirks et al. Int. J. Cancer 100, 49-56 (2002).

In another aspect, the compounds of the invention may inhibit Focal Adhesion Kinase (FAK), and may be useful as pharmaceuticals to treat conditions caused by a malfunction of signal cascades connected with FAK, such as in the treatment of particular tumors. The inhibition of endogenous FAK signaling results in reduced motility, and in some cases induces cell death. On the other hand, enhancing FAK signaling by exogenous expression increases cell motility. In addition, FAK is overexpressed in invasive and metastatic epithelial, mesenchymal, thyroid and prostate cancers. Consequently, an inhibitor of FAK is likely to be a drug for anti-tumor growth and metastasis. The compounds of the invention may thus be useful to prevent and/or treat a vertebrate and more particularly a mammal, affected by a neoplastic disease, in particular breast tumor, cancer of the bowel (colon and rectum), stomach cancer and cancer of the ovary and prostate, non-small cell lung cancer, small cell lung cancer, cancer of liver, melanoma, bladder tumor and cancer of head and neck.

The relation between FAK inhibition and immuno-system is described e.g. in G. A. van Seventer et al., Eur. J. Immunol. 2001, 31, 1417-1427. Therefore, the compounds of the invention are, for example, useful to prevent and/or treat a vertebrate and more particularly a mammal, affected by immune system disorders, diseases or disorders mediated by T lymphocytes, B lymphocytes, mast cells and/or eosinophils e.g. acute or chronic rejection of organ or tissue allo-or xenografts, atherosclerosis, vascular occlusion due to vascular injury such as angioplasty, restenosis, hypertension, heart failure, chronic obstructive pulmonary disease, CNS disease such as Alzheimer disease or amyotrophic lateral sclerosis; cancer; infectious disease such as AIDS; septic shock or adult respiratory distress syndrome, ischemia/reperfusion injury e.g. myocardial infarction, stroke, gut ischemia, renal failure or hemorrhage shock, or traumatic shock.

In yet another aspect, the compounds of the invention may inhibit zeta chain-associate protein 70 (ZAP-70). ZAP-70 protein tyrosine kinase interaction of the agents of the invention may be demonstrated, for example, by their ability to prevent phosphorylation of LAT-11 (linker for activation of T cell) by human ZAP-70 protein tyrosine kinase in aqueous solution. Therefore, the compounds of the invention may be useful for the prevention or treatment of disorders or diseases where ZAP-70 inhibition plays a role.

The compounds of the invention may also inhibit insulin like growth-factor receptor 1 (IGF-1R), and may be useful in the treatment of IGF-1 R mediated diseases. Examples of IGF-1R mediated diseases include but are not limited to proliferative diseases, such as tumors, for example breast, renal, prostate, colorectal, thyroid, ovarian, pancreas, neuronal, lung, uterine and gastro intestinal tumors, as well as osteosarcomas and melanomas. The efficacy of the compounds of the invention as inhibitors of IGF-1R tyrosine kinase activity may be demonstrated using a cellular capture ELISA. In this assay, the activity of the compounds of the invention against (IGF-1)-induced autophosphorylation of the IGF-1R is determined The compounds of the invention may also be useful in the treatment and/or prevention of acute or chronic inflammatory diseases or disorders or autoimmune diseases e.g. rheumatoid arthritis, osteoarthritis, systemic lupus erythematosus, Hashimoto's thyroiditis, multiple sclerosis, myasthenia gravis, diabetes (type I and II) and the disorders associated therewith, respiratory diseases such as asthma or inflammatory liver injury, inflammatory glomerular injury, cutaneous manifestations of immunologically-mediated disorders or illnesses, inflammatory and hyperproliferative skin diseases (such as psoriasis, atopic dermatitis, allergic contact dermatitis, irritant contact dermatitis and further eczematous dermatitis, seborrhoeic dermatitis), s inflammatory eye diseases, e.g. Sjoegren's syndrome, keratoconjunctivitis or uveitis, inflammatory bowel disease, Crohn's disease or ulcerative colitis.

In accordance with the foregoing, the present invention provides:

(1) a compound of the invention for use as a pharmaceutical;

(2) a compound of the invention for use as an ALK inhibitor, FAK inhibitor, ZAP-70 inhibitor and/or IGF-1R inhibitor, for example for use in any of the particular indications hereinbefore set forth;

(3) a pharmaceutical composition, e.g. for use in any of the indications herein before set forth, comprising a compound of the invention as active ingredient together with one or more pharmaceutically acceptable diluents or carriers;

(4) a method for the treatment of any particular indication set forth hereinbefore in a subject in need thereof which comprises administering an effective amount of a compound of the invention or a pharmaceutical composition comprising same;

(5) the use of a compound of the invention for the manufacture of a medicament for the treatment or prevention of a disease or condition in which ALK, FAK, ZAP-70 and/or IGF-1R activation plays a role or is implicated;

(6) the method as defined above under (4) comprising co-administration, e.g. concomitantly or in sequence, of a therapeutically effective amount of a compound of the invention and one or more further drug substances, said further drug substance being useful in any of the particular indications set forth hereinbefore;

(7) a combination comprising a therapeutically effective amount of a compound of the invention and one or more further drug substances, said further drug substance being useful in any of the particular indications set forth hereinbefore;

(8) use of a compound of the invention for the manufacture of a medicament for the treatment or prevention of a disease which responds to inhibition of the anaplastic lymphoma kinase;

(9) the use according to (8), wherein the disease to be treated is selected from anaplastic large cell lymphoma, non- Hodgkin's lymphomas, inflammatory myofibroblastic tumors, neuroblastomas and neoplastic diseases;

(10) the use according to (8) or (9), wherein the compound is or a pharmaceutically acceptable; salt of any one of the examples;

(11) a method for the treatment of a disease which responds to inhibition of the anaplastic lymphoma kinase, especially a disease selected from anaplastic large-cell lymphoma, non Hodgkin's lymphomas, inflammatory myofibroblastic tumors, neuroblastomas and neoplastic diseases, comprising administering an effective amount of a compound of the invention or a pharmaceutically acceptable salt thereof.

Administration and Pharmaceutical Compositions

In general, compounds of the invention will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors known to those of ordinary skill in the art. For example, for the treatment of neoplastic diseases and immune system disorders, the required dosage will also vary depending on the mode of administration, the particular condition to be treated and the effect desired.

In general, satisfactory results are indicated to be obtained systemically at daily dosages of from about 0.01 to about 100 mg/kg per body weight, or particularly, from about 0.03 to 2.5 mg/kg per body weight. An indicated daily dosage in the larger mammal, e.g. humans, may be in the range from about 0.5 mg to about 2000 mg, or more particularly, from about 0.5 mg to about 100 mg, conveniently administered, for example, in divided doses up to four times a day or in retard form. Suitable unit dosage forms for oral administration comprise from ca. 1 to 50 mg active ingredient.

Compounds of the invention may be administered as pharmaceutical compositions by any conventional route; for example, enterally, e.g., orally, e.g., in the form of tablets or capsules; parenterally, e.g., in the form of injectable solutions or suspensions; or topically, e.g., in the form of lotions, gels, ointments or creams, or in a nasal or suppository form.

Pharmaceutical compositions comprising a compound of the present invention in free form or in a pharmaceutically acceptable salt form in association with at least one pharmaceutically acceptable carrier or diluent may be manufactured in a conventional manner by mixing, granulating, coating, dissolving or lyophilizing processes. For example, pharmaceutical compositions comprising a compound of the invention in association with at least one pharmaceutical acceptable carrier or diluent may be manufactured in conventional manner by mixing with a pharmaceutically acceptable carrier or diluent. Unit dosage forms for oral administration contain, for example, from about 0.1 mg to about 500 mg of active substance.

In one embodiment, the pharmaceutical compositions are solutions of the active ingredient, including suspensions or dispersions, such as isotonic aqueous solutions. In the case of lyophilized compositions comprising the active ingredient alone or together with a carrier such as mannitol, dispersions or suspensions can be made up before use. The pharmaceutical compositions may be sterilized and/or contain adjuvants, such as preserving, stabilizing, wetting or emulsifying agents, solution promoters, salts for regulating the osmotic pressure and/or buffers. Suitable preservatives include but are not limited to antioxidants such as ascorbic acid, or microbicides, such as sorbic acid or benzoic acid. The solutions or suspensions may further comprise viscosity-increasing agents, including but not limited to, sodium carboxymethylcellulose, carboxymethylcellulose, dextran, polyvinylpyrrolidone, gelatins, or solubilizers, e.g. Tween 80 (polyoxyethylene(20)sorbitan mono-oleate).

Suspensions in oil may comprise as the oil component the vegetable, synthetic, or semi-synthetic oils customary for injection purposes. Examples include liquid fatty acid esters that contain as the acid component a long-chained fatty acid having from 8 to 22 carbon atoms, or in some embodiments, from 12 to 22 carbon atoms. Suitable liquid fatty acid esters include but are not limited to lauric acid, tridecylic acid, myristic acid, pentadecylic acid, palmitic acid, margaric acid, stearic acid, arachidic acid, behenic acid or corresponding unsaturated acids, for example oleic acid, elaidic acid, erucic acid, brassidic acid and linoleic acid, and if desired, may contain antioxidants, for example vitamin E, 3-carotene or 3,5-di-tert-butyl-hydroxytoluene. The alcohol component of these fatty acid esters may have six carbon atoms and may be monovalent or polyvalent, for example a mono-, di- or trivalent, alcohol. Suitable alcohol components include but are not limited to methanol, ethanol, propanol, butanol or pentanol or isomers thereof; glycol and glycerol.

Other suitable fatty acid esters include but are not limited ethyl-oleate, isopropyl myristate, isopropyl palmitate, LABRAFIL® M 2375, (polyoxyethylene glycerol), LABRAFIL® M 1944 CS (unsaturated polyglycolized glycerides prepared by alcoholysis of apricot kernel oil and comprising glycerides and polyethylene glycol ester), LABRASOL™ (saturated polyglycolized glycerides prepared by alcoholysis of TCM and comprising glycerides and polyethylene glycol ester; all available from GaKefosse, France), and/or MIGLYOL® 812 (triglyceride of saturated fatty acids of chain length $C_8$ to $C_{12}$ from Hüls A G, Germany), and vegetable oils such as cottonseed oil, almond oil, olive oil, castor oil, sesame oil, soybean oil, or groundnut oil.

Pharmaceutical compositions for oral administration may be obtained, for example, by combining the active ingredient with one or more solid carriers, and if desired, granulating a resulting mixture, and processing the mixture or granules by the inclusion of additional excipients, to form tablets or tablet cores.

Suitable carriers include but are not limited to fillers, such as sugars, for example lactose, saccharose, mannitol or sorbitol, cellulose preparations, and/or calcium phosphates, for example tricalcium phosphate or calcium hydrogen phosphate, and also binders, such as starches, for example corn, wheat, rice or potato starch, methylcellulose, hydroxypropyl methylcellulose, sodium carboxymethylcellulose, and/or polyvinylpyrrolidone, and/or, if desired, disintegrators, such as the above-mentioned starches, carboxymethyl starch, crosslinked polyvinylpyrrolidone, alginic acid or a salt thereof, such as sodium alginate. Additional excipients include flow conditioners and lubricants, for example silicic acid, talc, stearic acid or salts thereof, such as magnesium or calcium stearate, and/or polyethylene glycol, or derivatives thereof.

Tablet cores may be provided with suitable, optionally enteric, coatings through the use of, inter alia, concentrated sugar solutions which may comprise gum arabic, talc, polyvinylpyrrolidone, polyethylene glycol and/or titanium dioxide, or coating solutions in suitable organic solvents or solvent mixtures, or, for the preparation of enteric coatings, solutions of suitable cellulose preparations, such as acetylcellulose phthalate or hydroxypropylmethylcellulose phthalate. Dyes or pigments may be added to the tablets or tablet coatings, for example for identification purposes or to indicate different doses of active ingredient.

Pharmaceutical compositions for oral administration may also include hard capsules comprising gelatin or soft-sealed capsules comprising gelatin and a plasticizer, such as glycerol or sorbitol. The hard capsules may contain the active ingredient in the form of granules, for example in admixture with fillers, such as corn starch, binders, and/or glidants, such as talc or magnesium stearate, and optionally stabilizers. In soft capsules, the active ingredient may be dissolved or suspended in suitable liquid excipients, such as fatty oils, paraffin oil or liquid polyethylene glycols or fatty acid esters of ethylene or propylene glycol, to which stabilizers and detergents, for example of the polyoxyethylene sorbitan fatty acid ester type, may also be added.

Pharmaceutical compositions suitable for rectal administration are, for example, suppositories comprising a combination of the active ingredient and a suppository base. Suitable suppository bases are, for example, natural or synthetic triglycerides, paraffin hydrocarbons, polyethylene glycols or higher alkanols.

Pharmaceutical compositions suitable for parenteral administration may comprise aqueous solutions of an active ingredient in water-soluble form, for example of a water-soluble salt, or aqueous injection suspensions that contain viscosity-increasing substances, for example sodium carboxymethylcellulose, sorbitol and/or dextran, and, if desired, stabilizers. The active ingredient, optionally together with excipients, can also be in the form of a lyophilizate and can be made into a solution before parenteral administration by the addition of suitable solvents. Solutions such as are used, for example, for parenteral administration can also be employed as infusion solutions. The manufacture of injectable preparations is usually carried out under sterile conditions, as is the filling, for example, into ampoules or vials, and the sealing of the containers.

The compounds of the invention may be administered as the sole active ingredient, or together with other drugs useful against neoplastic diseases or useful in immunomodulating regimens. For example, the compounds of the invention may be used in accordance with the invention in combination with pharmaceutical compositions effective in various diseases as described above, e.g. with cyclophosphamide, 5-fluorouracil, fludarabine, gemcitabine, cisplatinum, carboplatin, vincristine, vinblastine, etoposide, irinotecan, paclitaxel, docetaxel, rituxan, doxorubicine, gefitinib, or imatinib; or also with cyclosporins, rapamycins, ascomycins or their immunosuppressive analogs, e.g. cyclosporin A, cyclosporin G, FK-506, sirolimus or everolimus, corticosteroids, e.g. prednisone, cyclophosphamide, azathioprene, methotrexate, gold salts, sulfasalazine, antimalarials, brequinar, leflunomide, mizoribine, mycophenolic acid, mycophenolate, mofetil, 15-deoxyspergualine, immuno-suppressive monoclonal antibodies, e.g. monoclonal antibodies to leukocyte receptors, e.g. MHC, CD2, CD3, CD4, CD7, CD25, CD28, I CD40, CD45, CD58, CD80, CD86, CD152, CD137, CD154, ICOS, LFA-1, VLA-4 or their ligands, or other immunomodulatory compounds, e.g. CTLA41g.

The invention also provides for a pharmaceutical combinations, e.g. a kit, comprising a) a first agent which is a compound of the invention as disclosed herein, in free form or in pharmaceutically acceptable salt form, and b) at least one co-agent. The kit can comprise instructions for its administration.

Processes for Making Compounds of the Invention

General procedures for preparing compounds of the invention are described in the Examples, infra. In the reactions described, reactive functional groups, for example hydroxy, amino, imino, thio or carboxy groups, where these are desired in the final product, may be protected to avoid their unwanted participation in the reactions. Conventional protecting groups may be used in accordance with standard practice (see e.g., T. W. Greene and P. G. M. Wuts in "Protective Groups in Organic Chemistry", John Wiley and Sons, 1991).

In some examples, compounds having Formula (1) may be prepared following the synthetic procedures described in Scheme 1:

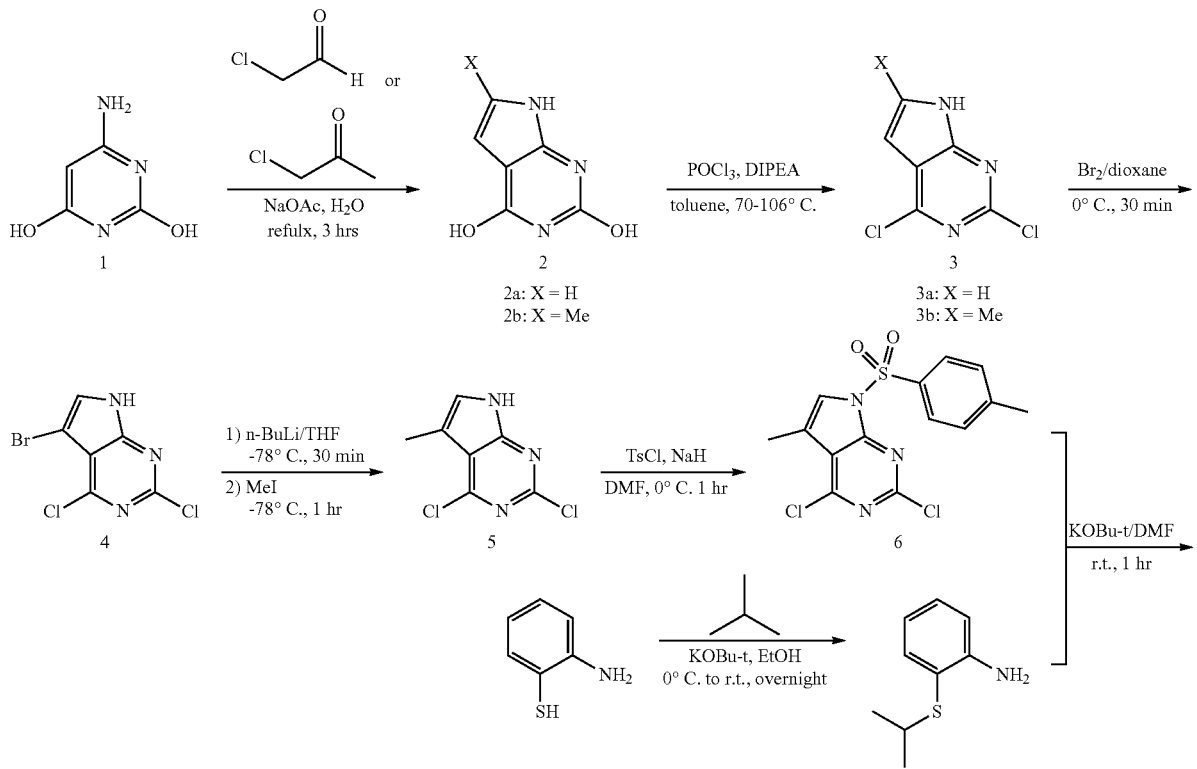

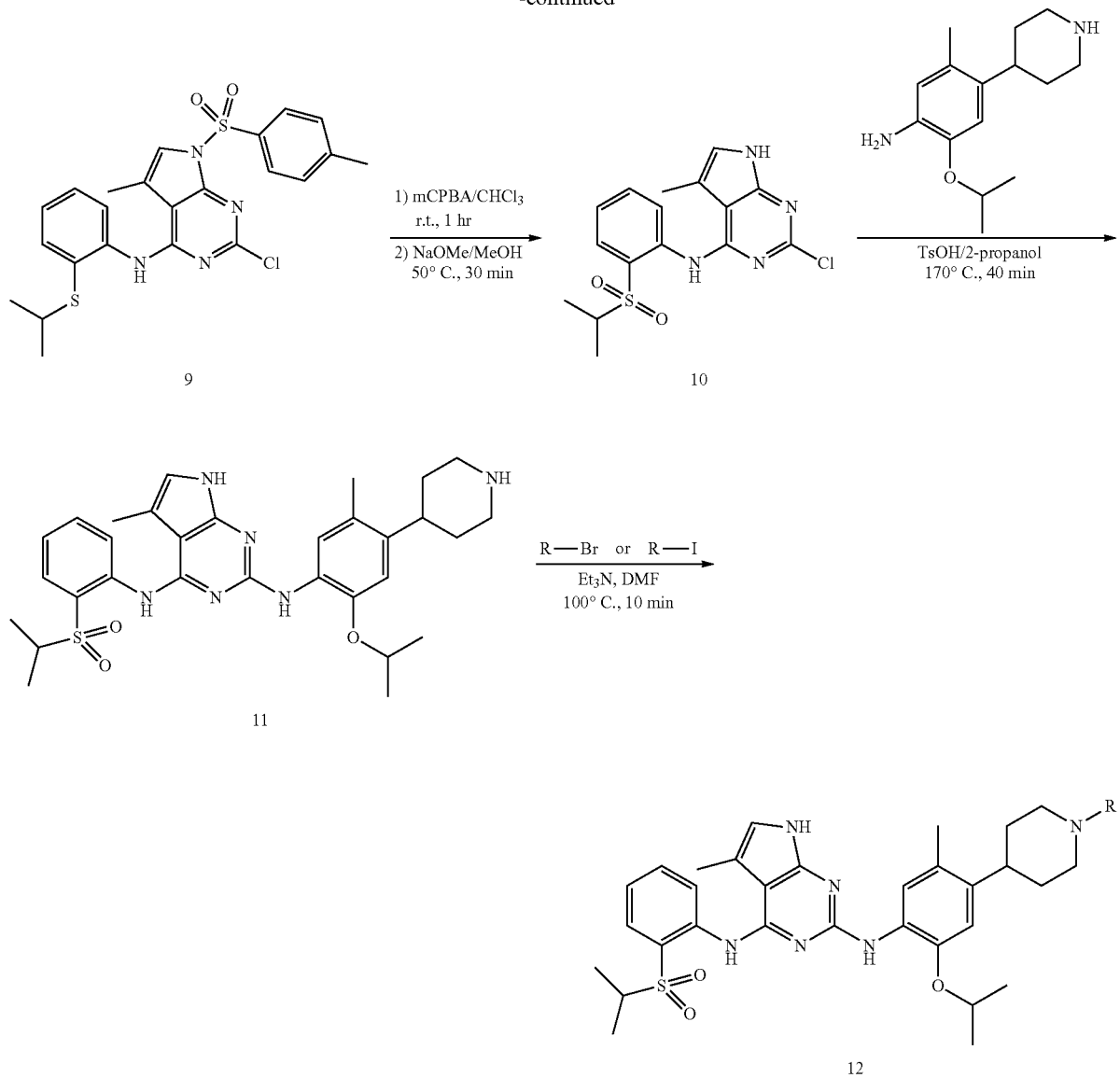
Compounds having Formula (6) may also be prepared following the synthetic procedures described in Scheme 2.
Scheme 2
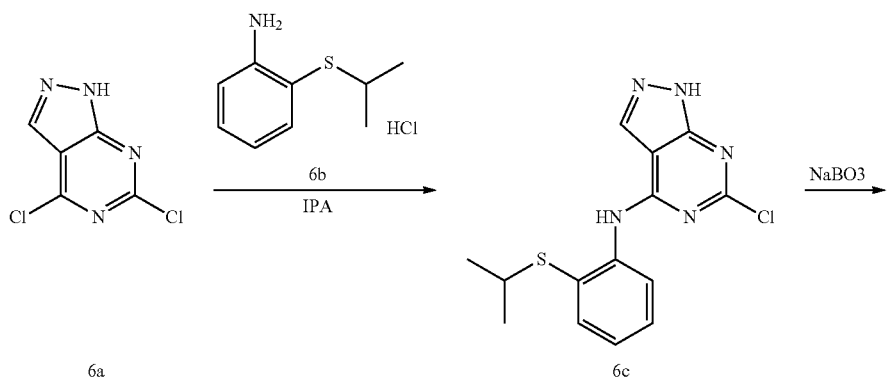

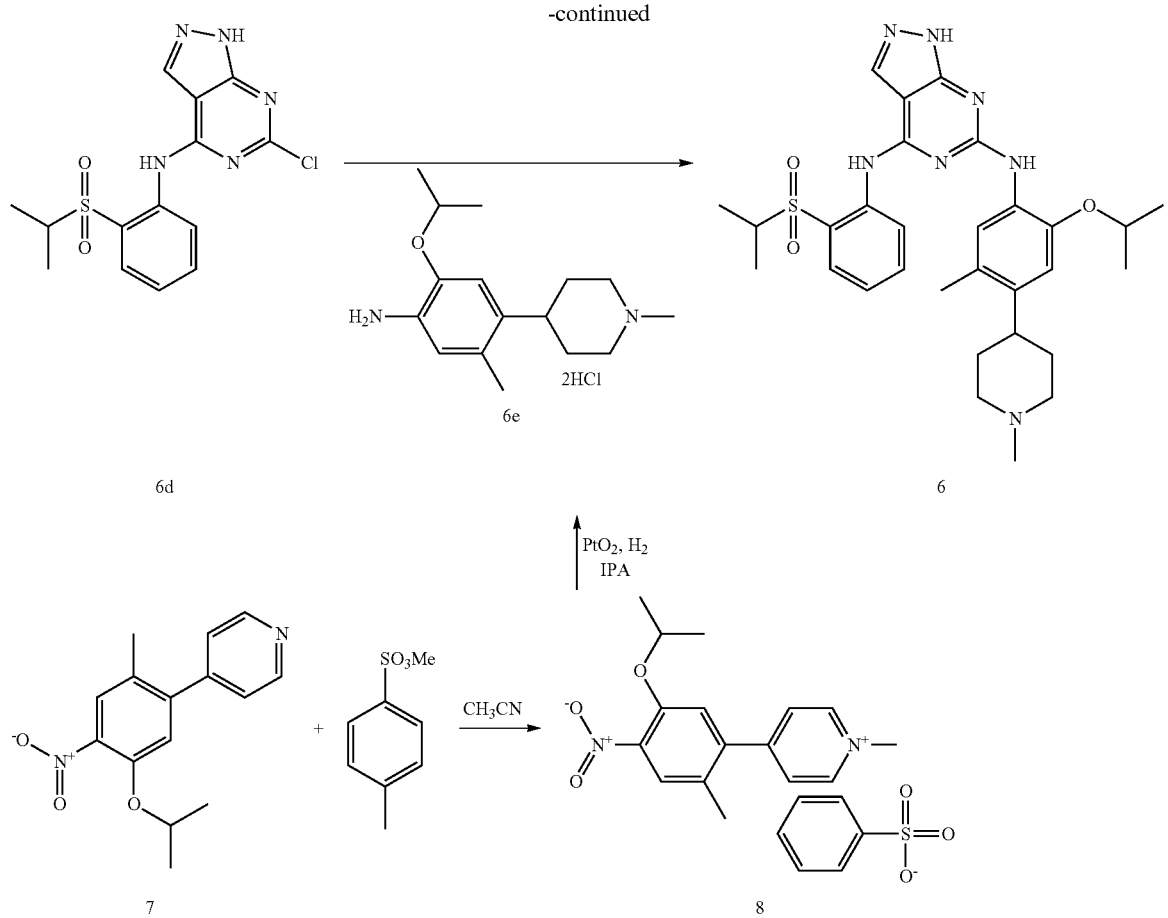

The compounds of the invention, including their salts, are also obtainable in the form of hydrates, or their crystals may include for example the solvent used for crystallization (present as solvates). Salts can usually be converted to compounds in free form, e.g., by treating with suitable basic agents, for example with alkali metal carbonates, alkali metal hydrogen carbonates, or alkali metal hydroxides, such as potassium carbonate or sodium hydroxide. A compound of the invention in a base addition salt form may be converted to the corresponding free acid by treating with a suitable acid (e.g., hydrochloric acid, etc.). In view of the close relationship between the novel compounds in free form and those in the form of their salts, including those salts that may be used as intermediates, for example in the purification or identification of the novel compounds, any reference to the free compounds is to be understood as referring also to the corresponding salts, as appropriate.

Salts of the inventive compounds with a salt-forming group may be prepared in a manner known per se. Acid addition salts of compounds of (1), (2), (2A), (3A), (3B), (3C), (3D), (4) or (5) may thus be obtained by treatment with an acid or with a suitable anion exchange reagent. Pharmaceutically acceptable salts of the compounds of the invention may be formed, for example, as acid addition salts, with organic or inorganic acids, from compounds of (1), (2), (2A), (3A), (3B), (3C), (3D), (4) or (5) with a basic nitrogen atom.

Suitable inorganic acids include, but are not limited to, halogen acids, such as hydrochloric acid, sulfuric acid, or phosphoric acid. Suitable organic acids include, but are not limited to, carboxylic, phosphoric, sulfonic or sulfamic acids, for example acetic acid, propionic acid, octanoic acid, decanoic acid, dodecanoic acid, glycolic acid, lactic acid, fumaric acid, succinic acid, adipic acid, pimelic acid, suberic acid, azelaic acid,-malic acid, tartaric acid, citric acid, amino acids, such as glutamic acid or aspartic acid, maleic acid, hydroxymaleic acid, methylmaleic acid, cyclohexanecarboxylic acid, adamantanecarboxylic acid, benzoic acid, salicylic acid, 4 aminosalicylic acid, phthalic acid, phenylacetic acid, mandelic acid, cinnamic acid, methane-or ethane-sulfonic acid, 2-hydroxyethanesulfonic acid, ethane-1,2-disulfonic acid, benzenesulfonic acid, 2-naphthalenesulfonic acid, 1,5-naphthalene-disulfonic acid, 2-, 3-or 4 methylbenzenesulfonic acid, methylsulfuric acid, ethylsulfuric acid, dodecylsulfuric acid, N cyclohexylsulfamic acid, N-methyl-, N-ethyl-or N-propyl-sulfamic acid, or other organic protonic acids, such as ascorbic acid. For isolation or purification purposes, it is also possible to use pharmaceutically unacceptable salts, for example picrates or perchlorates. For therapeutic use, only pharmaceutically acceptable salts or free compounds are employed (where applicable in the form of pharmaceutical preparations).

Compounds of the invention in unoxidized form may be prepared from N-oxides of compounds of the invention by treating with a reducing agent (e.g., sulfur, sulfur dioxide, triphenyl phosphine, lithium borohydride, sodium borohydride, phosphorus trichloride, tribromide, or the like) in a suitable inert organic solvent (e.g. acetonitrile, ethanol, aqueous dioxane, or the like) at 0 to 80° C.

Prodrug derivatives of the compounds of the invention may be prepared by methods known to those of ordinary skill in the art (e.g., for further details see Saulnier et al., (1994), Bioorganic and Medicinal Chemistry Letters, Vol. 4, p. 1985). For example, appropriate prodrugs may be prepared by reacting a non-derivatized compound of the invention with a suitable carbamylating agent (e.g., 1,1-acyloxyalkylcarbanochloridate, para-nitrophenyl carbonate, or the like).

Protected derivatives of the compounds of the invention may be made by means known to those of ordinary skill in the art. A detailed description of techniques applicable to the creation of protecting groups and their removal may be found in T. W. Greene, "Protecting Groups in Organic Chemistry", 3$^{rd}$ edition, John Wiley and Sons, Inc., 1999.

Compounds of the invention may be prepared as their individual stereoisomers by reacting a racemic mixture of the compound with an optically active resolving agent to form a pair of diastereoisomeric compounds, separating the diastereomers and recovering the optically pure enantiomers. Resolution of enantiomers may be carried out using covalent diastereomeric derivatives of the compounds of the invention, or by using dissociable complexes (e.g., crystalline diastereomeric salts). Diastereomers have distinct physical properties (e.g., melting points, boiling points, solubilities, reactivity, etc.) and may be readily separated by taking advantage of these dissimilarities. The diastereomers may be separated by fractionated crystallization, chromatography, or by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture may be found in Jean Jacques, Andre Collet, Samuel H. Wilen, "Enantiomers, Racemates and Resolutions", John Wiley And Sons, Inc., 1981.

In summary, the compounds of the invention may be made by a process as described in the Examples; and (a) optionally converting a compound of the invention into a pharmaceutically acceptable salt;

(b) optionally converting a salt form of a compound of the invention to a non-salt form;

(c) optionally converting an unoxidized form of a compound of the invention into a pharmaceutically acceptable N-oxide;

(d) optionally converting an N-oxide form of a compound of the invention to its unoxidized form;

(e) optionally resolving an individual isomer of a compound of the invention from a mixture of isomers;

(f) optionally converting a non-derivatized compound of the invention into a pharmaceutically acceptable prodrug derivative; and (g) optionally converting a prodrug derivative of a compound of the invention to its non-derivatized form.

Insofar as the production of the starting materials is not particularly described, the compounds are known or can be prepared analogously to methods known in the art or as disclosed in the Examples hereinafter. One of skill in the art will appreciate that the above transformations are only representative of methods for preparation of the compounds of the present invention, and that other well known methods can similarly be used. The present invention is further exemplified, but not limited, by the following and Examples that illustrate the preparation of the compounds of the invention.

PREPARATION OF INTERMEDIATES

Intermediate 1

2,4,6-trichloropyrimidine-5-carbaldehyde

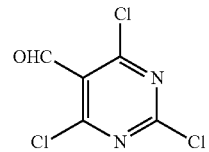 [SMILES: O=Cc1c(Cl)nc(Cl)nc1Cl]

Barbituric acid (5.0 g, 39.1 mmol) was added to a stirred solution of POCl$_3$ (23.5 mL, 252 mmol) and DMF (3 mL, 38.8 mmol) at room temperature under nitrogen atmosphere. The mixture was refluxed for 15 h, then allowed to cool down to room temperature. Excess POCl$_3$ was removed in vacuo, and the resulting viscous material was carefully poured onto crushed ice (150 g). The pale brown precipitate was filtered and dried under vacuum to afford 2,4,6-trichloropyrimidine-5-carbaldehyde.

Intermediate 2

2,4-dichloro-6-(2-(isopropylsulfonylphenylamino) pyrimidine-5-carbaldehyde

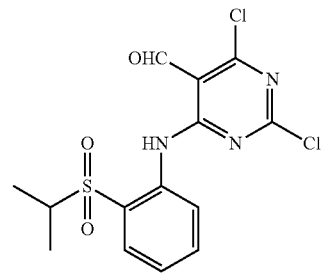 [SMILES: CC(C)S(=O)(=O)c1ccccc1Nc1nc(Cl)nc(Cl)c1C=O]

To a stirred solution of 2,4,6-trichloropyrimidine-5-carbaldehyde (5.0 g, 23.8 mmol) in DCM (50 mL) was added 2-(isopropylsulfonyl)aniline (9.5 g, 47.6 mmol) at 0° C. under nitrogen atmosphere. The reaction mixture was warmed to room temperature gradually and stirred overnight. The solid was filtered off, and the filtrate was concentrated in vacuo and purified by silica gel chromatography (DCM/EtOAC/Hexanes: 15/15/70) to afford 2,4-dichloro-6-(2-(isopropylsulfonyl)phenylamino)pyrimidine-5-carbaldehyde. MS (ES+): 374.0 (MH+).

Intermediate 3

1-(2,4-dichloro-6-(2-(isopropylsulfonyl)phenylamino)pyrimidin-5-yl)ethanol

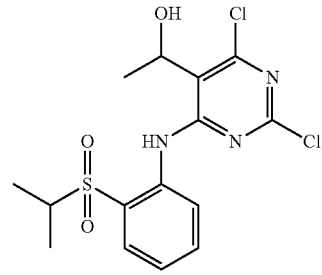 [SMILES: CC(O)c1c(Cl)nc(Cl)nc1Nc1ccccc1S(=O)(=O)C(C)C]

To the solution of 2,4-dichloro-6-(2-(isopropylsulfonyl)phenylamino)pyrimidine-5-carbaldehyde (797 mg, 2.14 mmol) in THF (10 mL) was added methyl magnesium bromide (3.0 M in diethyl ether, 6.4 mL, 19.3 mmol) at −78° C. under nitrogen atmosphere. The reaction mixture was warmed to room temperature gradually, and stirred overnight. The reaction mixture was poured into 20 mL of saturated aqueous NH₄Cl at 0° C., and partitioned between EtOAc (30 mL×2) and brine (10 mL×2). The collected organic extracts were dried over Na₂SO₄, concentrated in vacuo, and purified by silica gel chromatography (EtOAc/Hexanes: 30/70) to afford 1-(2,4-dichloro-6-(2-(isopropylsulfonyl)phenylamino)pyrimidin-5-yl)ethanol. MS (ES+): 390.0 (MH+).

Intermediate 4

1-(2,4-dichloro-6-(2-(isopropylsulfonyl)phenylamino)pyrimidin-5-yl)ethanone

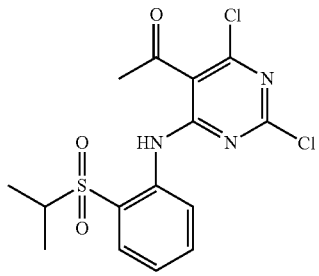 [SMILES: CC(=O)c1c(Cl)nc(Cl)nc1Nc1ccccc1S(=O)(=O)C(C)C]

To the solution of 1-(2,4-dichloro-6-(2-(isopropylsulfonyl)phenylamino)pyrimidin-5-yl)ethanol (580 mg, 1.49 mmol) in DCM (30 mL) was added PDC (561 mg, 1.49 mmol). The reaction mixture was stirred at room temperature overnight. The reaction mixture was filtered through a pad of silica gel, and the pad was washed by 1 L of DCM. The filtrate was concentrated in vacuo to afford 1-(2,4-dichloro-6-(2-(isopropylsulfonyl)phenylamino)pyrimidin-5-yl)ethanone as a pale yellow solid. MS (ES+): 388.0 (MH+).

Intermediate 5

Tert-butyl 4-(4-(5-acetyl-4-chloro-6-(2-(isopropylsulfonyl)phenylamino)pyrimidin-2-ylamino)-5-isopropoxy-2-methylphenyl)piperidine-1-carboxylate

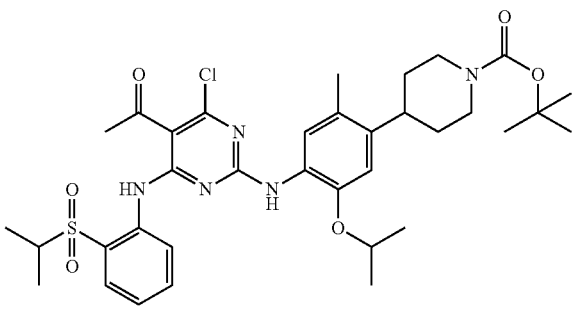 [SMILES: CC(=O)c1c(Cl)nc(Nc2cc(C)c(C3CCN(C(=O)OC(C)(C)C)CC3)cc2OC(C)C)nc1Nc1ccccc1S(=O)(=O)C(C)C]

To a solution of 1-(2,4-dichloro-6-(2-(isopropylsulfonyl)phenylamino)pyrimidin-5-yl)ethanone (113 mg, 0.29 mmol) in EtOH (2 mL) was added tert-butyl-4-(4-amino-5-isopropoxy-2-methylphenyl)piperidine-1-carboxylate (203 mg, 0.58 mmol), and the reaction mixture was heated at 130° C. for 30 min The reaction was concentrated in vacuo, followed by purification by silica gel chromatography (EtOAC/Hexanes: 3/7) to afford Tert-butyl 4-(4-(5-acetyl-4-chloro-6-(2-(isopropylsulfonyl)phenylamino)pyrimidin-2-ylamino)-5-isopropoxy-2-methylphenyl)piperidine-1-carboxylate. MS (ES+): 700.3 (MH+).

Preparation of Final Compounds

EXAMPLE 1

1-(4-(4-(5-chloro-4-(2-(isopropylsulfonyl)phenylamino)pyrimidin-2-ylamino)-5-isopropoxy-2-methylphenyl)piperidin-1-yl)-2-(dimethylamino)ethanone
(1)

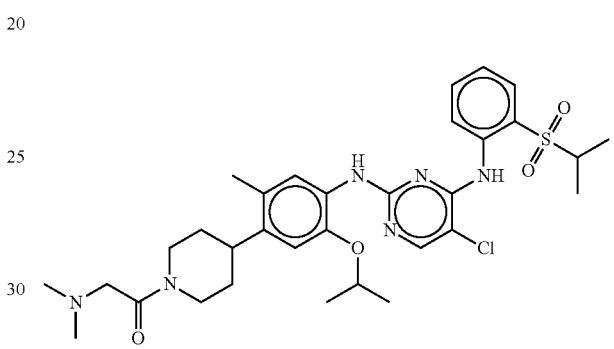

4-(5-isopropoxy-2-methyl-4-nitro-phenyl)-pyridine

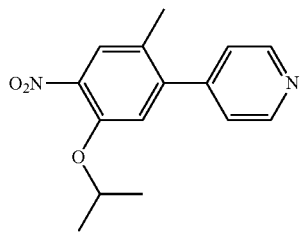 [SMILES: Cc1cc([N+](=O)[O-])c(OC(C)C)cc1-c1ccncc1]

4-Pyridineboronic acid (147 mg, 1.20 mmol, 1.1 equiv.) was dissolved in a 2:1 v/v mixture of dioxane and H₂O (15 mL) and N₂ was bubbled through for 5 minutes. Tris(dibenzylidene acetone)dipalladium (0) (100 mg, 0.109 mmol, 0.1 equiv.), 2-dicyclohexylphosphine-2'-6'-dimethoxy biphenyl (112 mg, 0.272 mmol, 0.25 equiv.), 1-chloro-5-isopropoxy-2-methyl-4-nitro-benzene (250 mg, 1.09 mmol, 1.0 equiv.) and K₃PO₄ (462 mg, 2.18 mmol, 2.0 equiv.) were added under a N₂ blanket. The reaction vessel was sealed and heated with microwave irradiation to 150° C. for 20 minutes. After cooling to room temperature, the reaction was diluted with ethyl acetate and washed with 1N aqueous NaOH (twice). The organic layer was then dried over Na₂SO₄ and filtered. After concentration, the crude product was purified by silica gel chromatography (gradient from hexanes to 30% ethyl acetate in hexanes) to give 4-(5-Isopropoxy-2-methyl-4-nitro-phenyl)-pyridine as a brown solid: ESMS m/z 273.1 (M+H⁺).

4-(4-Amino-5-isopropoxy-2-methyl-phenyl)-piperidine-1-carboxylic acid tert-butyl ester

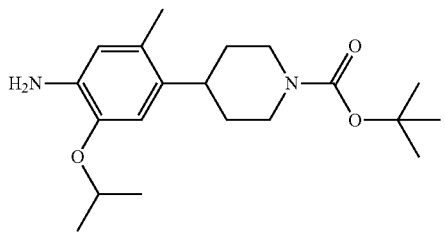 [SMILES: Cc1cc(N)c(OC(C)C)cc1C1CCN(C(=O)OC(C)(C)C)CC1]

4-(5-isopropoxy-2-methyl-4-nitro-phenyl)-pyridine from the previous step (438 mg, 1.61 mmol) dissolved in acetic acid (30 mL) was treated with TFA (0.24 mL, 3.22 mmol) and $PtO_2$ (176 mg, 40% w/w). The reaction mixture was vigorously stirred under 1 atm. $H_2$ for 36 hours. The reaction mixture was filtered and the filtrate was concentrated under vacuum. The resulting residue was diluted with ethyl acetate and washed with 1 N aqueous NaOH (twice). The organic layer was then dried over $Na_2SO_4$ and filtered. After concentration, the crude product (391 mg) was dissolved in anhydrous $CH_2Cl_2$ (30 mL). TEA is added (0.44 mL, 3.15, 2 equiv.) followed by $Boc_2O$ (344 mg, 1.57 equiv, 1 equiv.). The reaction was stirred at room temperature for 30 minutes. The reaction was concentrated under vacuum. The resulting residue was purified by silica gel chromatography (gradient from hexanes to 30% ethyl acetate in hexanes) to give 4-(4-amino-5-isopropoxy-2-methyl-phenyl)-piperidine-1-carboxylic acid tert-butyl ester as a sticky foam: ESMS m/z 293.1 (M-tBu+H)$^+$.

Steps 4 and 5: 4-(4-Amino-5-isopropoxy-2-methyl-phenyl)-piperidine-1-carboxylic acid tert-butyl ester (170 mg, 0.488 mmol) from the previous step, (2,5-dichloro-pyrimidin-4-yl)-[2-(propane-2-sulfonyl)-phenyl]-amine (169 mg, 0.488 mmol, 1 equiv.), xantphos (28 mg, 0.049 mmol, 0.1 equiv.), palladium acetate (5.5 mg, 0.024 mmol, 0.05 equiv.), and $Cs_2CO_3$ (477 mg, 1.46 mmol, 3 equiv.) were dissolved in anhydrous THF (6 mL). $N_2$ is bubbled through the reaction mixture for 5 minutes and the reaction vessel was sealed and heated with microwave irradiation to 150° C. for 20 minutes. The reaction was filtered and the filtrate concentrated under vacuum. After concentration, the crude product was purified by silica gel chromatography (gradient from hexanes to 30% ethyl acetate in hexanes) to give 4-(4-{5-chloro-4-[2-(propane-2-sulfonyl)-phenylamino]-pyrimidin-2-ylamino}-5-isopropoxy-2-methyl-phenyl)-piperidine-1-carboxylic acid tert-butyl ester as a yellow film: ESMS m/z 658.3 (M+H$^+$). This product (105 mg, 0.160 mmol) was dissolved in $CH_2Cl_2$ (3 mL) and treated with TFA (3 mL). After 45 minutes, the reaction was concentrated under vacuum. 1 N HCl in $Et_2O$ (5 mL×2) was added causing the product HCl salt to precipitate. The solvent was removed by decantation. The resulting 5-Chloro-N$^2$-(2-isopropoxy-5-methyl-4-piperidin-4-yl-phenyl)-N$^4$-[2-(propane-2-sulfonyl)-phenyl]-pyrimidine-2,4-diamine was dried under high vacuum, generating an off-white powder: $^1$H NMR (400 MHz, DMSO-d$_6$+trace D$_2$O) δ 8.32 (s, 1H), 8.27 (d, 1H), 7.88 (d, 1H), 7.67 (dd, 1H), 7.45 (dd, 1H), 7.42 (s, 1H), 6.79 (s, 1H), 4.56-4.48 (m, 1H), 3.49-3.32 (m, 3H), 3.10-2.91 (m, 3H), 2.09 (s, 3H), 1.89-1.77 (m, 4H), 1.22 (d, 6H), 1.13 (d, 6H); ESMS m/z 558.1 (M+H$^+$).

1-(4-(4-(5-chloro-4-(2-(isopropylsulfonyl)phenylamino)pyrimidin-2-ylamino)-5-isopropoxy-2-methylphenyl)piperidin-1-yl)-2-(dimethylamino)ethanone

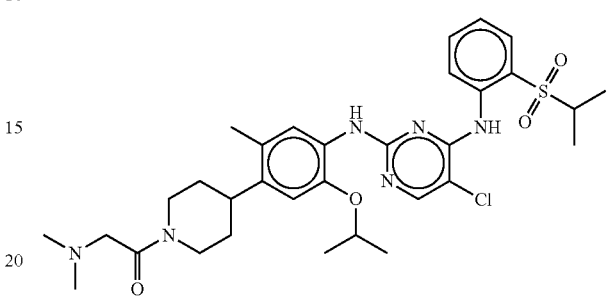

Prepared according to the method of by replacing N6-(2-isopropoxy-5-methyl-4-(piperidin-4-yl)phenyl)-N4-(2-(isopropylsulfonyl)phenyl)-1H-pyrazolo[3,4-d]pyrimidine-4,6-diamine with 5-chloro-N2-(2-isopropoxy-5-methyl-4-(piperidin-4-yl)phenyl)-N4-(2-(isopropylsulfonyl)phenyl)pyrimidine-2,4-diamine. The product was obtained. MS (ES$^+$): 643.28 (M+1)$^+$.

EXAMPLE 2

(S)-(4-(4-(5-chloro-4-(2-(isopropylsulfonyl)phenylamino)pyrimidin-2-ylamino)-5-isopropoxy-2-methylphenyl)piperidin-1-yl)(pyrrolidin-2-yl)methanone (7)

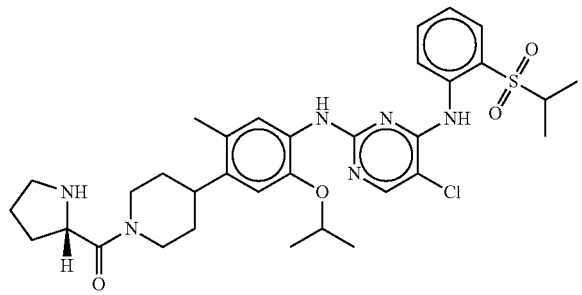

Prepared according to the method of Example 1 by replacing N6-(2-isopropoxy-5-methyl-4-(piperidin-4-yl)phenyl)-N4-(2-(isopropylsulfonyl)phenyl)-1H-pyrazolo[3,4-d]pyrimidine-4,6-diamine with 5-chloro-N2-(2-isopropoxy-5-methyl-4-(piperidin-4-yl)phenyl)-N4-(2-(isopropylsulfonyl)phenyl)pyrimidine-2,4-diamine and replacing 2-(dimethylamino)acetyl chloride hydrochloride with (S)-pyrrolidine-2-carbonyl chloride hydrochloride. Product was obtained. MS (ES$^+$): 655.28 (M+1).

EXAMPLE 3

(S)-(4-(4-(5-chloro-4-(2-(difluoromethylsulfonyl)phenylamino)pyrimidin-2-ylamino)-5-isopropoxy-2-methylphenyl)piperidin-1-yl)(pyrrolidin-2-yl)methanone (8)

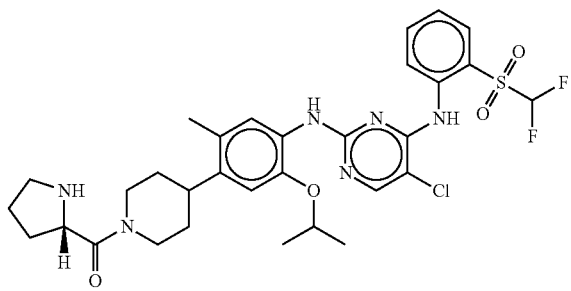

2,5-dichloro-N-(2-(difluoromethylsulfonyl)phenyl)-pyrimidin-4-amine

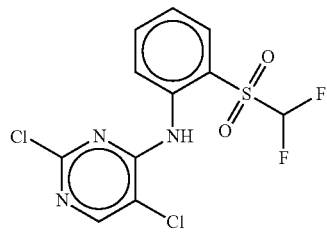

To a solution of 2,4,5-trichloropyrimidine (1 mmol) and 2-(difluoromethylsulfonyl)aniline (1 mmol) in 10 mL of DMF was added sodium hydride (2 mmol) at 0° C. After the reaction mixture was warmed to room temperature and stirred at 50° C. for 1 hour. After work-up and flash chromatography (CH$_2$Cl$_2$/MeOH 9:1), product was obtained. MS (ES$^+$): 353.96 (M+1)$^+$.

5-chloro-N4-(2-(difluoromethylsulfonyl)phenyl)-N2-(2-isopropoxy-5-methyl-4-(piperidin-4-yl)phenyl)pyrimidine-2,4-diamine

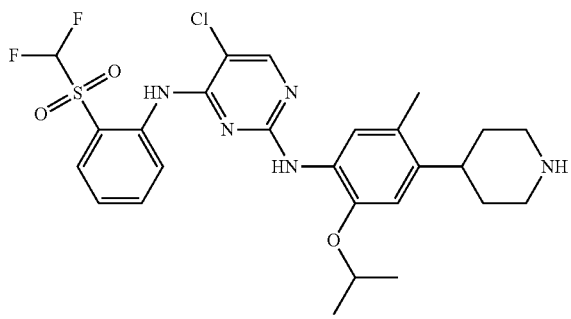 [SMILES: Cc1cc(Nc2ncc(Cl)c(Nc3ccccc3S(=O)(=O)C(F)F)n2)c(OC(C)C)cc1C1CCNCC1]

To a suspension of 2,5-dichloro-N-(2-(difluoromethylsulfonyl)phenyl)-pyrimidin-4-amine (0.5 mmol) in 1 mL of isopropanol, was added 2-isopropoxy-5-methyl-4-(piperidin-4-yl)aniline (0.5 mmol) and 4-methylbenzenesulfonic acid (0.5 mmol). The suspension was stirred at 150° C. for 3 hours. After work-up and prep-HPLC, product was obtained. MS (ES$^+$): 566.17 (M+1)$^+$.

(S)-(4-(4-(5-chloro-4-(2-(difluoromethylsulfonyl)-phenylamino)-pyrimidin-2-ylamino)-5-isopropoxy-2-methylphenyl)piperidin-1-yl)(pyrrolidin-2-yl)methanone Prepared according to the method of Example 1 by replacing N6-(2-isopropoxy-5-methyl-4-(piperidin-4-yl)phenyl)-N4-(2-(isopropylsulfonyl)phenyl)-1H-pyrazolo[3,4-d]pyrimidine-4,6-diamine with 5-chloro-N4-(2-(difluoromethylsulfonyl)phenyl)-N2-(2-isopropoxy-5-methyl-4-(piperidin-4-yl)phenyl)pyrimidine-2,4-diamine and replacing 2-(dimethylamino)acetyl chloride hydrochloride with (S)-pyrrolidine-2-carbonyl chloride hydrochloride, product was obtained. MS (ES$^+$): 663.23 (M+1)$^+$.

1-(4-(4-(5-chloro-4-(2-(difluoromethylsulfonyl)phenylamino)-pyrimidin-2-ylamino)-5-isopropoxy-2-methylphenyl)piperidin-1-yl)-2-(dimethylamino)ethanone

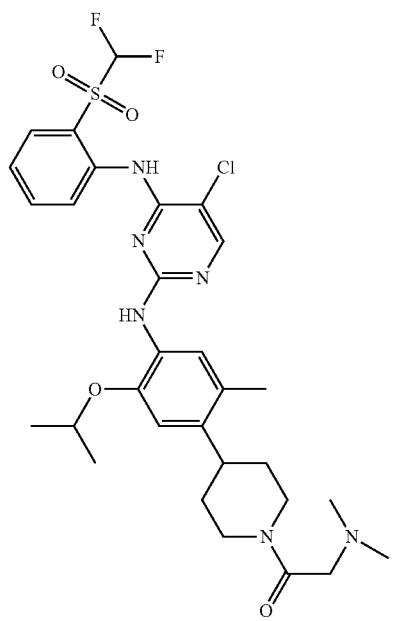 [SMILES: Cc1cc(Nc2ncc(Cl)c(Nc3ccccc3S(=O)(=O)C(F)F)n2)c(OC(C)C)cc1C1CCN(C(=O)CN(C)C)CC1]

Prepared according to the method of Example 1 by replacing N6-(2-isopropoxy-5-methyl-4-(piperidin-4-yl)phenyl)-N4-(2-(isopropylsulfonyl)phenyl)-1H-pyrazolo[3,4-d]pyrimidine-4,6-diamine with 5-chloro-N4-(2-(difluoromethylsulfonyl)phenyl)-N2-(2-isopropoxy-5-methyl-4-(piperidin-4-yl)phenyl)pyrimidine-2,4-diamine, product was obtained. MS (ES$^+$): 651.23 (M+1)$^+$.

EXAMPLE 4

6-(5-chloro-4-(2-(isopropylsulfonyl)phenylamino)pyrimidin-2-ylamino)-2-(1-(2-(dimethylamino)acetyl)piperidin-4-yl)-5-isopropoxyisoindolin-1-one (9)

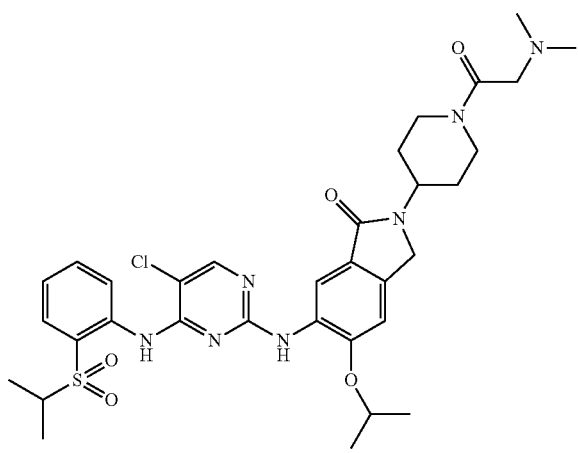 [SMILES: CC(C)Oc1cc2c(cc1Nc1ncc(Cl)c(Nc3ccccc3S(=O)(=O)C(C)C)n1)C(=O)N(C1CCN(C(=O)CN(C)C)CC1)C2]

2-Chloro-4-isopropoxy-5-nitro-benzoic acid

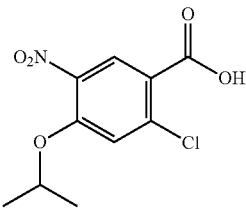 [SMILES: CC(C)Oc1cc(Cl)c(C(=O)O)cc1[N+](=O)[O-]]

A mixture of 2-chloro-4-fluoro-5-nitro-benzoic acid (5.0 g, 22.8 mmol) and cesium carbonate (29.7 g, 91.1 mmol) in 2-propanol (100 mL) was heated at 50° C. overnight. The solvent was removed in vacuo and 100 mL of water was added. Concentrated aqueous HCl was added dropwise to this solution at 0° C. until the pH is 2. The product precipitate which formed was isolated by filtration, washed by water and dried under vacuum to give 2-chloro-4-isopropoxy-5-nitro-benzoic acid.

4-(2-Chloro-4-isopropoxy-5-nitro-benzoylamino)-piperidine-1-carboxylic acid tert-butyl ester

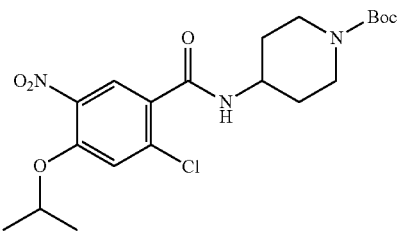 [SMILES: CC(C)Oc1cc(Cl)c(C(=O)NC2CCN(C(=O)OC(C)(C)C)CC2)cc1[N+](=O)[O-]]

To a solution of 2-chloro-4-isopropoxy-5-nitro-benzoic acid (10 g, 38.5 mmol) in DCM (200 mL) and DMF (1 mL), was added thionyl chloride (9.17 g, 77 mmol) slowly via a syringe. The mixture was stirred for 3 hours, and concentrated to dryness. The obtained white solid, 2-chloro-4-isopropoxy-5-nitro-benzoyl chloride, was dried under vacuum. To a mixture of 4-amino-piperidine-1-carboxylic acid tert-butyl ester (1.44 g, 7.2 mmol) and triethylamine (3 mL, 21.6 mmol) in DCM (100 mL), was added 2-chloro-4-isopropoxy-5-nitro-benzoyl chloride (2 g, 7.2 mmol) dissolved in DCM (10 mL) slowly via syringe. The mixture was stirred at room temperature for 3 hours, and concentrated. The obtained solid was dissolved in ethyl acetate and washed with water and brine respectively. After evaporation of the solvent, the title compound was obtained as light yellow solid, and was directly used for the next step without further purification.

4-(4-Isopropoxy-5-nitro-2-vinyl-benzoylamino)-piperidine-1-carboxylic acid tert-butyl ester

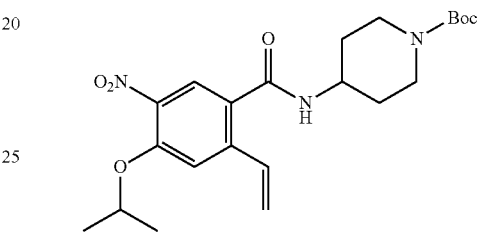

To a mixture of 4-(2-chloro-4-isopropoxy-5-nitro-benzoylamino)-piperidine-1-carboxylic acid tert-butyl ester (7.2 mmol) obtained in the previous step, vinylboronic acid dibutyl ester (1.72 g, 9.4 mmol) and sodium carbonate (5.34 g, 50.4 mmol) in THF/H$_2$O (100/25 mL) was added dichlorobis(triphenylphospine)palladium (II) (442 mg, 5% mmol). The mixture was purged with N$_2$ for 3 min and heated at 90° C. under N$_2$ overnight in a round bottom flask equipped with a condenser. The mixture was cooled to room temperature and poured into saturated aqueous ammonia chloride solution. The mixture was extracted with ethyl acetate (3×100 mL). The organic extracts were combined, washed with brine and concentrated. The crude product was purified with silica gel column chromatography (40% ethyl acetate in hexanes) to afford 4-(4-isopropoxy-5-nitro-2-vinyl-benzoylamino)-piperidine-1-carboxylic acid tert-butyl ester as white solid.

4-(5-Isopropoxy-6-nitro-1-oxo-1,3-dihydro-isoindol-2-yl)-piperidine-1-carboxylic acid tert-butyl ester

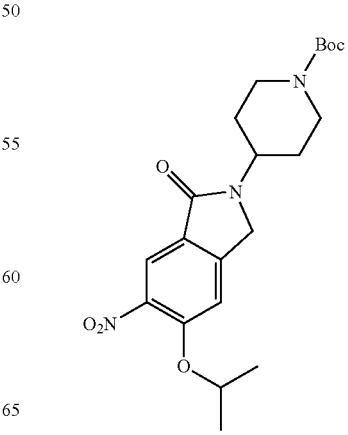

4-(4-Isopropoxy-5-nitro-2-vinyl-benzoylamino)-piperidine-1-carboxylic acid tert-butyl ester obtained from the previous step (1.9 g, 4.38 mmol) was dissolved in DCM (100 mL) and cooled to −78° C. O$_3$ (g) was bubbled into the solution until the solution's color turned blue/gray. The solution was then purged with N$_2$ (g) until the blue color disappeared. The solution was warmed to room temperature and treated with triphenyl phosphine resin (5 g) pre-swelled in DCM (100 mL). After 30 min, the mixture was filtered, the filtrate was concentrated, and the resulting residue was dissolved in DCM/TFA (100 mL/25 mL). To this mixture was added triethyl silane (4.6 mL, 17.5 mmol). The resulting mixture was stirred at room temperature overnight. The reaction mixture was concentrated and re-dissolved in DCM, and the DCM solution was washed with 1N aqueous HCl (3×20 mL). The combined aqueous layer was treated with conc. aqueous NaOH until pH=12. The aqueous layer was extracted with ethyl acetate (3×30 mL). The combined organic layers were washed with brine, and dried over sodium sulfate. A light yellow solid was obtained after evaporation of the organic solvent.

The solid was dissolved in a mixture of methanol and triethylamine (100 mL, 9:1 v/v). To this mixture was added di-tert-butyl dicarbonate (680 mg, 3.1 mmol). After stirring at 50° C. for 30 minutes, the mixture was concentrated and purified by silica gel flash column chromatography (eluent: 40~50% ethyl acetate in hexanes) to afford 4-(5-Isopropoxy-6-nitro-1-oxo-1,3-dihydro-isoindol-2-yl)-piperidine-1-carboxylic acid tert-butyl ester as a white solid. $^1$H NMR (400 MHz, CDCl$_3$) δ 8.19 (s, 1H), 7.11 (s, 1H), 4.74 (q, 1H), 4.45-4.38 (m, 1H), 4.35 (s, 2H), 2.90-2.80 (m, 2H), 1.85-1.81 (m, 2H), 1.66-1.63 (m, 2H), 1.48 (s, 9H), 1.42 (d, 6H).

6-(5-chloro-4-(2-(isopropylsulfonyl)phenylamino)-pyrimidin-2-ylamino)-5-isopropoxy-2-(piperidin-4-yl)isoindolin-1-one

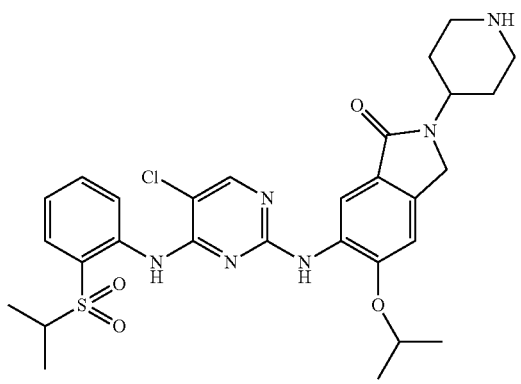 [SMILES: CC(C)Oc1cc2c(cc1Nc1ncc(Cl)c(Nc3ccccc3S(=O)(=O)C(C)C)n1)C(=O)N(C1CCNCC1)C2]

To a solution of 4-(5-isopropoxy-6-nitro-1-oxo-1,3-dihydro-isoindol-2-yl)-piperidine-1-carboxylic acid tert-butyl ester from the previous step (850 mg, 2 mmol) in methanol, was added Pd/C (10% on carbon, 100 mg). The mixture was hydrogenated under 1 atm of hydrogen gas. After 4 hours, the mixture was filtered and concentrated. The obtained aniline, as yellow solid, was used for next step without additional purification. To a mixture of the crude product (2 mmol) from previous step, (2,5-dichloro-pyrimidin-4-yl)-[2-(propane-2-sulfonyl)-phenyl]-amine (770 mg, 2.2 mmol), cesium carbonate (1.3 g, 4 mmol), and xantphos (115 mg, 0.2 mmol) in THF (20 mL), was added palladium acetate (22 mg, 5% mmol) in a microwave tube. The mixture was purged with N$_2$ for 3 min. The sealed tube was heated at 150° C. for 20 min under microwave irradiation. The mixture was cooled, filtered and concentrated. The residue was purified by silica gel flash column chromatography (eluent: 65% ethyl acetate in hexanes) to afford a yellow solid. The solid was treated with DCM/TFA (1/1, 10 mL) for 1 hour followed by concentration under vacuum. Final purification using preparative RP LC-MS afforded 6-{5-Chloro-4-[2-(propane-2-sulfonyl)-phenylamino]-pyrimidin-2-ylamino}-5-isopropoxy-2-piperidin-4-yl-2,3-dihydro-isoindol-1-one as a white solid. $^1$H NMR (400 MHz, CDCl$_3$) δ 10.38 (s, 1H), 10.13 (s, 1H), 9.60-9.50 (br, 1H), 9.34-9.21 (br, 1H), 8.46 (d, 1H), 8.26 (s, 1H), 8.08 (s, 1H), 7.91 (dd, 1H), 7.71 (m, 1H), 7.34 (t, 1H), 7.03 (s, 1H), 4.30 (m, 1H), 4.53 (m, 1H), 4.33 (s, 2H), 3.62 (m, 2H), 3.21-3.09 (m, 3H), 2.31-2.21 (m, 2H), 2.09-2.05 (m, 2H), 1.41 (d, 6H), 2.30 (d, 6H); ESMS m/z 599.2 (M+H$^+$).

6-(5-chloro-4-(2-(isopropylsulfonyl)phenylamino)pyrimidin-2-ylamino)-2-(1-(2-(dimethylamino)acetyl)piperidin-4-yl)-5-isopropoxyisoindolin-1-one To a solution of 6-(5-chloro-4-(2-(isopropylsulfonyl)phenylamino)-pyrimidin-2-ylamino)-5-isopropoxy-2-(piperidin-4-yl)isoindolin-1-one (20 mg, 0.03 mmol) in DMF (1.0 mL) was added 2-(dimethylamion)acetyl chloride hydrochloride (0.17 mmol, 26 mg) and triethyl amine (0.18 mmol, 18 mg). The reaction mixture was stirred at room temperature 1 h. and the solid byproduct was removed by filtration. The remaining filtrate was purified by preparative RP-HPLC to afford 6-(5-chloro-4-(2-(isopropylsulfonyl)-phenylamino)pyrimidin-2-ylamino)-2-(1-(2-(dimethylamino)acetyl)piperidin-4-yl)-5-isopropoxyisoindolin-1-one.

EXAMPLE 5

(S)-6-(5-chloro-4-(2-(isopropylsulfonyl)phenylamino)pyrimidin-2-ylamino)-5-isopropoxy-2-(1-(1-methylpyrrolidine-2-carbonyl)piperidin-4-yl)isoindolin-1-one (15)

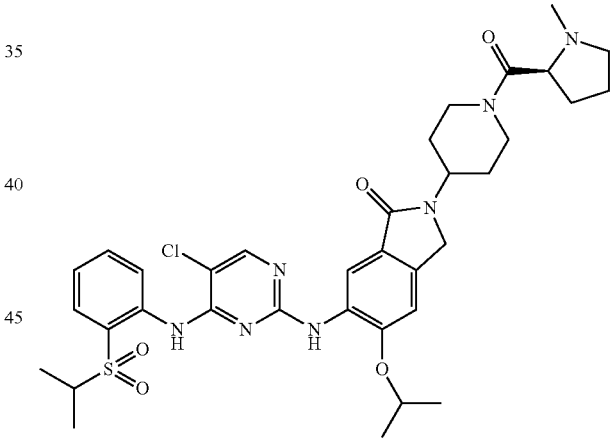

To a solution of 6-(5-chloro-4-(2-(isopropylsulfonyl)phenylamino)-pyrimidin-2-ylamino)-5-isopropoxy-2-(piperidin-4-yl)isoindolin-1-one (52 mg, 0.09 mmol) in DMF (1.0 mL) was added (S)-1-(tert-butoxycarbonyl)pyrrolidine-2-carboxylic acid (19 mg, 0.09 mmol), HATU (50 mg, 0.130 mmol), and DIEA (0.174 mmol, 30 μL) sequentially. The reaction mixture was stirred for 1 h, then partitioned between EtOAc and water. The organic extracts were dried (Na$_2$SO$_4$), and concentrated in vacuo. The crude product was stirred in a solution of DCM (1 mL) and TFA (1 mL) for 1 h, then concentrated in vacuo. To the solution of the resulting crude product in 1 mL of MeOH and 1 mL of THF was added 3 drops of AcOH, formaldehyde (37 wt. % solution in water, 0.09 mmol, 7 mg). After stirring for 1 h, sodium cyanoborohydride (0.18 mmol, 11 mg) was added, and the reaction mixture was stirred for another 30 min. The reaction mixture was filtered and the resulting filtrate was purified by preparative RP-HPLC to afford (S)-6-(5-chloro-4-(2-(isopropylsulfonyl)phenylamino)-pyrimidin-2-ylamino)-5-isopropoxy-2-(1-(1-methylpyrrolidine-2-carbonyl)piperidin-4-yl)isoindolin-1-one.

EXAMPLE 6

2-(1-(azetidine-3-carbonyl)piperidin-4-yl)-6-(5-chloro-4-(2-(isopropylsulfonyl)phenylamino)pyrimidin-2-ylamino)-5-isopropoxyisoindolin-1-one (16)

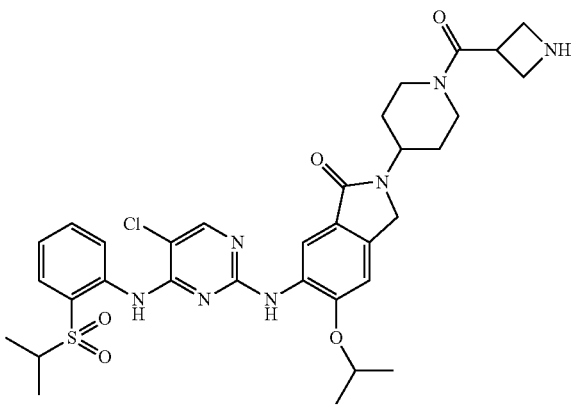 [SMILES: CC(C)Oc1cc2c(cc1Nc1ncc(Cl)c(Nc3ccccc3S(=O)(=O)C(C)C)n1)C(=O)N(C1CCN(C(=O)C3CNC3)CC1)C2]

To a solution of 6-(5-chloro-4-(2-(isopropylsulfonyl)phenylamino)-pyrimidin-2-ylamino)-5-isopropoxy-2-(piperidin-4-yl)isoindolin-1-one C (41 mg, 0.07 mmol) in DMF (1.0 mL) was added 1-(tert-butoxycarbonyl)azetidine-3-carboxylic acid (14 mg, 0.07 mmol), HATU (39 mg, 0.104 mmol), and DIEA (0.138 mmol, 24 µL) sequentially. The reaction mixture was stirred for 1 h, then partitioned between EtOAc and water. The organic extracts were dried (Na2SO4), and concentrated in vacuo. The crude product was stirred in a solution of DCM (1 mL) and TFA (1 mL) at room temperature for 1 h. The resulting solution was concentrated and then purified by preparative RP-HPLC to afford 2-(1-(azetidine-3-carbonyl)piperidin-4-yl)-6-(5-chloro-4-(2-(isopropylsulfonyl)phenylamino)pyrimidin-2-ylamino)-5-isopropoxyisoindolin-1-one.

EXAMPLE 7

2-(dimethylamino)-1-(4-(5-isopropoxy-4-(4-(2-(isopropylsulfonyl)phenylamino)-1H-pyrazolo[3,4-d]pyrimidin-6-ylamino)-2-methylphenyl)piperidin-1-yl)ethanone (21)

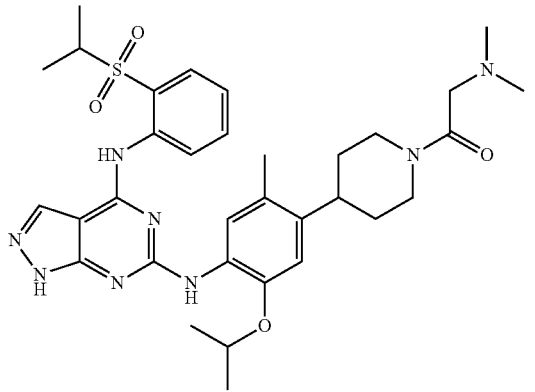 [SMILES: Cc1cc(Nc2nc(Nc3ccccc3S(=O)(=O)C(C)C)c3cn[nH]c3n2)c(OC(C)C)cc1C1CCN(C(=O)CN(C)C)CC1]

4-hydroxyl-6-methylmercaptopyrazolo[3,4-d]pyrimidine

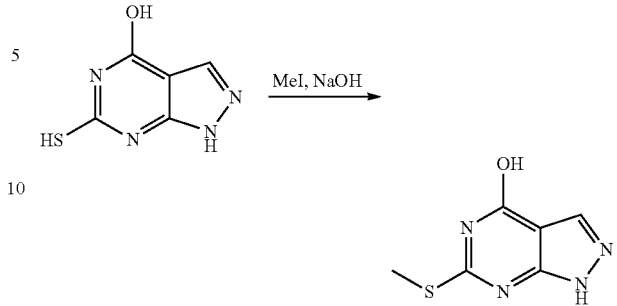

4-hydroxy-6-mercapto-pyrazolo[3,4-d]pyrimidine (14 g) was dissolved in a solution of sodium hydroxide (10 g) in water (300 mL). The solution was cooled to 5° C. and shaken with of methyl iodide (12 g). After 15-20 minutes the solution was charcoaled, filtered and acidified with acetic acid to yield crude product. Re-crystallization in acid gave the desired product MS (ES+): 183.0 (M+1)+.

4-chloro-6-methylmercaptopyrazolo[3,4-d]pyrimidine

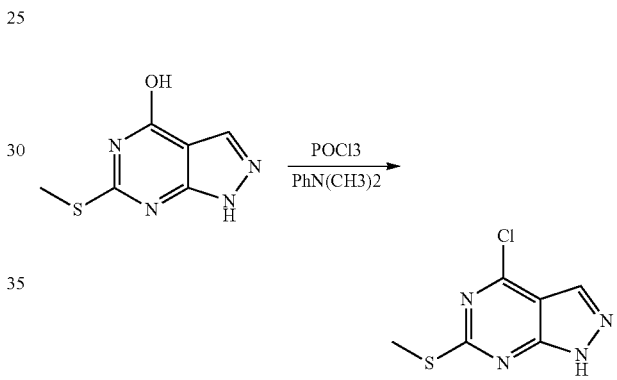

To 40 mL of phosphorus oxychloride and dimethylaniline (3 mL) was added 2.2 g of crude 4-hydroxy-methylmercaptopyrazolo[3,4-d ]pyrimidine. The solution was refluxed for 30-60 minutes until all the solid has dissolved. The excess phosphorus was removed under reduced pressure. The syrupy residue was poured with vigorous stirring onto a mixture of ice water. After ten minutes, the aqueous solution was extracted with ether. The ether solution was washed with cold water and dried with anhydrous sodium sulfate. The reaction was filtered and ether was removed under pressure to give the product. 211.0 (M+1)+.

N-(2-(isopropylsulfonyl)phenyl)-6-(methylthio)-1H-pyrazolo[3,4-d]pyrimidin-4-amine

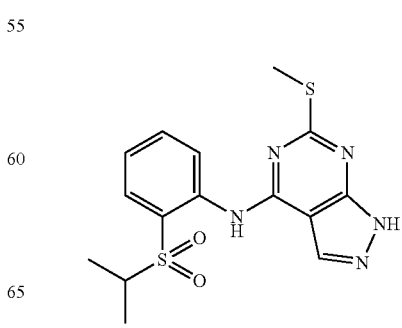

A solution of 4-chloro-6-methylmercaptopyrazolo[3,4-d]pyrimidine (10 mmol) and 2-(N,N-dimethylsulfonyl)aniline (10 mmol) in 100 mL of isopropanol was stirred at reflux for 1 hours. After cooling down to room temperature, triethylamine (12 mmol) was added to the reaction mixture, then the solution was heated under reflux for half hour. After workup and flash chromatography (hexane/EtOAc 4:1), product was obtained. 364.08 (M+1)+.

N-(2-(isopropylsulfonyl)phenyl)-6-(methylsulfonyl)-1H-pyrazolo[3,4-d]pyrimidin-4-amine

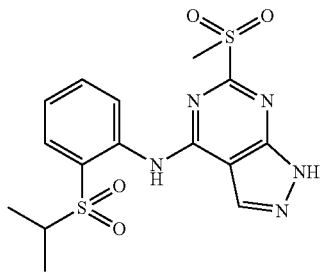 [SMILES: CC(C)S(=O)(=O)c1ccccc1Nc1nc(S(C)(=O)=O)nc2[nH]ncc12]

To a solution of N-(2-(isopropylsulfonyl)phenyl)-6-(methylthio)-1H-pyrazolo[3,4-d]pyrimidin-4-amine (1 mmol) in 10 mL of 1,2-dicholoroethane, was added MCPBA (3 mmol) at 0° C. After the reaction mixture was warmed to room temperature and stirred for 1 hour, product was obtained by flash chromatography (CH₂Cl₂/MeOH 9:1). MS (ES+): 396.07 (M+1)+.

N6-(2-isopropoxy-5-methyl-4-(piperidin-4-yl)phenyl)-N4-(2-(isopropylsulfonyl)phenyl)-1H-pyrazolo[3,4-d]pyrimidine-4,6-diamine

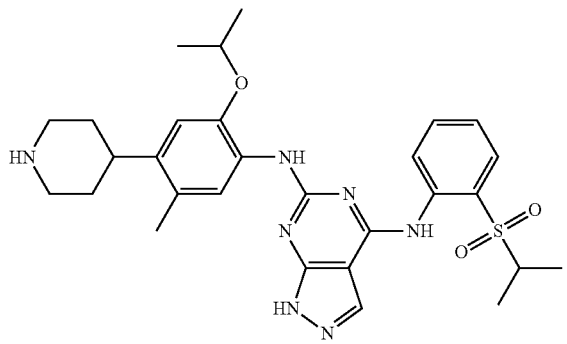 [SMILES: Cc1cc(Nc2nc(Nc3ccccc3S(=O)(=O)C(C)C)c3cn[nH]c3n2)c(OC(C)C)cc1C1CCNCC1]

To a suspension of N-(2-(isopropylsulfonyl)phenyl)-6-(methylsulfonyl)-1H-pyrazolo[3,4-d]pyrimidin-4-amine (0.5 mmol) in 1 mL of isopropanol, was added 2-isopropoxy-5-methyl-4-(piperidin-4-yl)aniline (0.5 mmol) and 4-methylbenzenesulfonic acid (0.5 mmol). The suspension was stirred at 150° C. for 3 hours. After prep-HPLC, the final product was obtained. 1H NMR (CDCl3, 400 MHz) δ 8.74-8.77 (d, 1H), 8.24 (s, 1H), 7.92-7.96 (m, 2H), 7.65-7.70 (m, 1H), 7.27-7.33 (m, 1H), 6.85(s, 1H), 4.60-4.67 (m. 1H), 3.71-3.74 (m, 2H), 3.25-3.32 (m, 1H), 2.78-2.97(m, 6H), 2.28-2.33 (m, 5H), 1.95-1.98 (m, 2H), 1.39-1.41(d, 6H), 1.33-1.35 (d, 6H); MS (ES+): 578.28 (M+1)+.

2-(dimethylamino)-1-(4-(5-isopropoxy-4-(4-(2-(isopropylsulfonyl)phenylamino)-1H-pyrazolo[3,4-d]pyrimidin-6-ylamino)-2-methylphenyl)piperidin-1-yl)ethanone

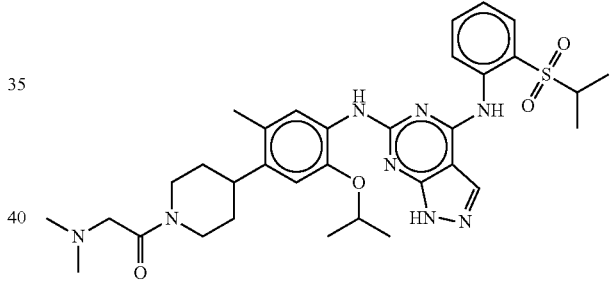

N6-(2-isopropoxy-5-methyl-4-(piperidin-4-yl)phenyl)-N4-(2-(isopropylsulfonyl)phenyl)-1H-pyrazolo[3,4-d]pyrimidine-4,6-diamine (56 mg) was dissolved in 3 mL of dichloromethane. The solution was cooled to 5° C. and 2-(dimethylamino)acetyl chloride hydrochloride (24 mg) was added to the solution followed by triethylamine (15 mg). The solution was stirred at room temperature for approximately 30 minutes. After Prep-LC-MS, the final product is obtained. MS (ES+): 649.32 (M+1)+.

By repeating the procedures described in the above examples (intermediates and final compounds), using appropriate starting materials, the following compounds of Formula I, as identified in Table 1, were obtained.

TABLE 1

| | Structure | Physical Data<br>¹H NMR 400 MHz (DMSO-d6) and/or MS (m/z) | ALK IC50 (μM) |
|---|---|---|---|
| 1 | 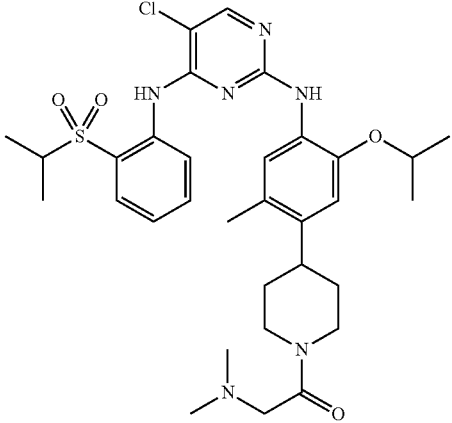 [SMILES: Cc1cc(Nc2ncc(Cl)c(Nc3ccccc3S(=O)(=O)C(C)C)n2)c(OC(C)C)cc1C1CCN(C(=O)CN(C)C)CC1]<br>1-(4-(4-(5-chloro-4-(2-(isopropylsulfonyl)phenylamino)pyrimidin-2-ylamino)-5-isopropoxy-2-methylphenyl)piperidin-1-yl)-2-(dimethylamino)ethanone | MS (ES⁺): 643.2 (M + 1)⁺. | 0.026 |
| 2 | 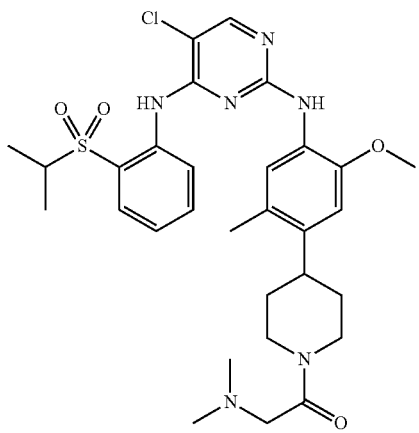 [SMILES: COc1cc(C2CCN(C(=O)CN(C)C)CC2)c(C)cc1Nc1ncc(Cl)c(Nc2ccccc2S(=O)(=O)C(C)C)n1]<br>1-(4-(4-(5-chloro-4-(2-(isopropylsulfonyl)phenylamino)pyrimidin-2-ylamino)-5-methoxy-2-methylphenyl)piperidin-1-yl)-2-(dimethylamino)ethanone | MS (ES⁺): 615.2 (M + 1)⁺. | 0.008 |
| 3 | 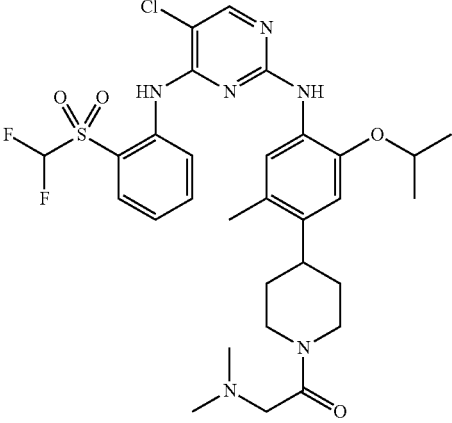 [SMILES: Cc1cc(Nc2ncc(Cl)c(Nc3ccccc3S(=O)(=O)C(F)F)n2)c(OC(C)C)cc1C1CCN(C(=O)CN(C)C)CC1]<br>1-(4-(4-(5-chloro-4-(2-(difluoromethylsulfonyl)phenylamino)pyrimidin-2-ylamino)-5-isopropoxy-2-methylphenyl)piperidin-1-yl)-2-(dimethylamino)ethanone | MS (ES⁺): 651.1 (M + 1)⁺. | 0.077 |

TABLE 1-continued

| Structure | Physical Data ¹H NMR 400 MHz (DMSO-d6) and/or MS (m/z) | ALK IC50 (μM) |
|---|---|---|
| 4 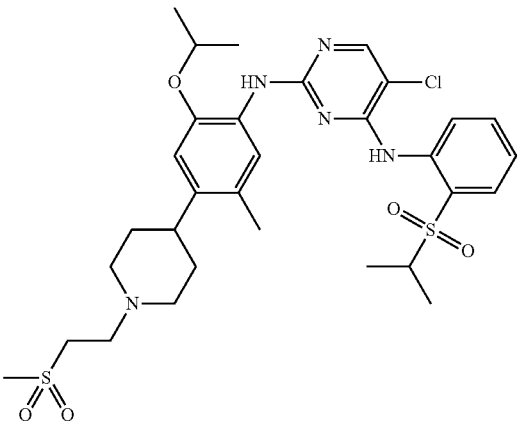 [SMILES: Cc1cc(Nc2ncc(Cl)c(Nc3ccccc3S(=O)(=O)C(C)C)n2)c(OC(C)C)cc1C1CCN(CCS(C)(=O)=O)CC1] 5-chloro-N2-(2-isopropoxy-5-methyl-4-(1-(2-(methylsulfonyl)ethyl)piperidin-4-yl)phenyl)-N4-(2-(isopropylsulfonyl)phenyl)pyrimidine-2,4-diamine | MS (ES$^+$): 664.2 (M + 1)$^+$. | |
| 5 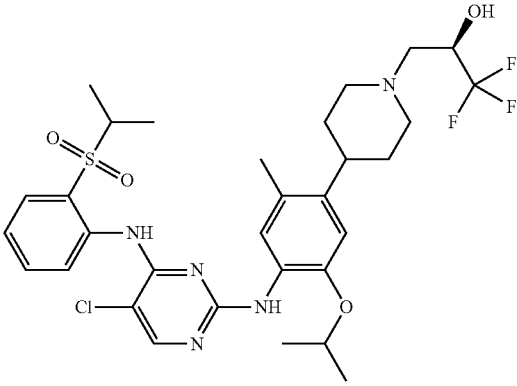 (R)-3-(4-(4-(5-chloro-4-(2-(isopropylsulfonyl)phenylamino)pyrimidin-2-ylamino)-5-isopropoxy-2-methylphenyl)piperidin-1-yl)-1,1,1-trifluoropropan-2-ol | MS (ES$^+$): 679.2 (M + 1)$^+$. | 0.088 |
| 6 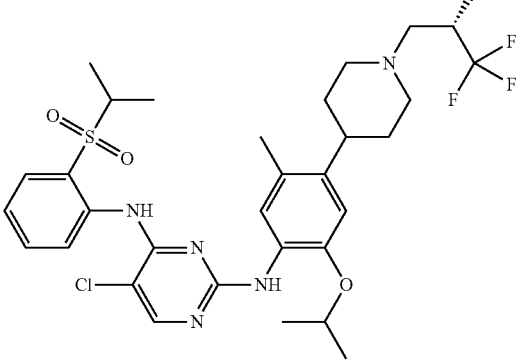 (S)-3-(4-(4-(5-chloro-4-(2-(isopropylsulfonyl)phenylamino)pyrimidin-2-ylamino)-5-isopropoxy-2-methylphenyl)piperidin-1-yl)-1,1,1-trifluoropropan-2-ol | MS (ES$^+$): 679.2 (M + 1)$^+$. | 0.043 |

TABLE 1-continued

| | Structure | Physical Data<br>$^1$H NMR 400 MHz (DMSO-d6)<br>and/or MS (m/z) | ALK IC50 (μM) |
|---|---|---|---|
| 7 | 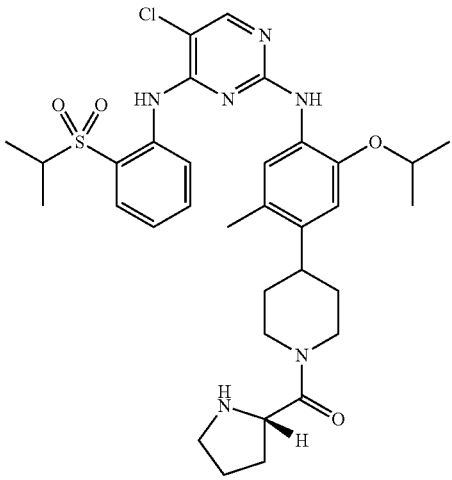 [SMILES: Cc1cc(Nc2ncc(Cl)c(Nc3ccccc3S(=O)(=O)C(C)C)n2)c(OC(C)C)cc1C1CCN(C(=O)[C@@H]2CCCN2)CC1]<br>(S)-(4-(4-(5-chloro-4-(2-(isopropylsulfonyl)phenylamino)pyrimidin-2-ylamino)-5-isopropoxy-2-methylphenyl)piperidin-1-yl)(pyrrolidin-2-yl)methanone | MS (ES+): 655.2 (M + 1)+. | 0.013 |
| 8 | 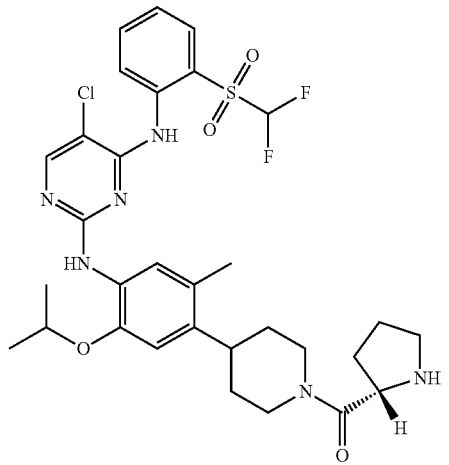 [SMILES: Cc1cc(Nc2ncc(Cl)c(Nc3ccccc3S(=O)(=O)C(F)F)n2)c(OC(C)C)cc1C1CCN(C(=O)[C@@H]2CCCN2)CC1]<br>(S)-(4-(4-(5-chloro-4-(2-(difluoromethylsulfonyl)phenylamino)pyrimidin-2-ylamino)-5-isopropoxy-2-methylphenyl)piperidin-1-yl)(pyrrolidin-2-yl)methanone | MS (ES+): 663.2 (M + 1)+. | 0.034 |

TABLE 1-continued

| Structure | Physical Data<br>¹H NMR 400<br>MHz (DMSO-d6)<br>and/or MS (m/z) | ALK<br>IC50<br>(μM) |
|---|---|---|
| 9 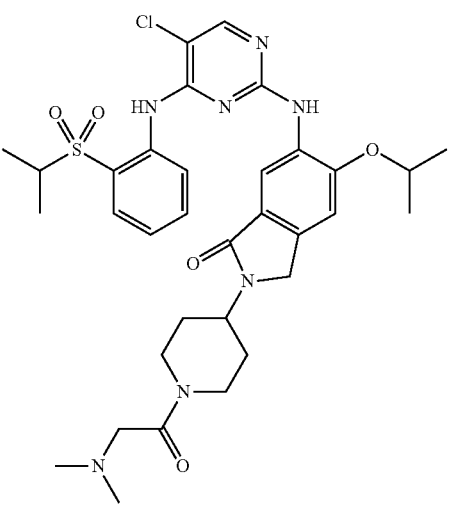 [SMILES: CC(C)Oc1cc2c(cc1Nc1ncc(Cl)c(Nc3ccccc3S(=O)(=O)C(C)C)n1)C(=O)N(C1CCN(C(=O)CN(C)C)CC1)C2]<br>6-(5-chloro-4-(2-(isopropylsulfonyl)<br>phenylamino)pyrimidin-2-ylamino)-2-(1-(2-<br>(dimethylamino)acetyl)piperidin-4-yl)-5-<br>isopropoxyisoindolin-1-one | MS (ES⁺): 684.2<br>(M + 1)⁺.<br>¹H NMR (MeOD-d₄)<br>δ 8.43 (dd, 1H), 8.26<br>(s, 1H), 8.13 (s,<br>1H), 7.80 (dd, 1H),<br>7.68 (m, 1H), 7.28 (m,<br>1H), 7.14 (s, 1H),<br>4.71 (m, 1H), 4.62<br>(m, 1H), 4.34 (s, 2H),<br>4.28 (m, 1H), 4.23<br>(m, 2H), 3.73 (m,<br>1H), 2.87 (s,<br>6H), 2.79 (m,<br>2H), 1.77 (m,<br>5H), 1.29 (d, 6H),<br>1.16 (d, 6H) | 0.006 |
| 10 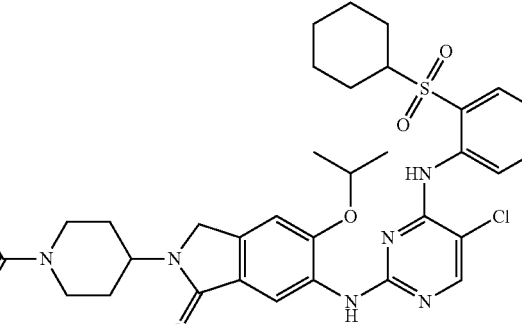<br>6-(5-chloro-4-(2-(cyclohexylsulfonyl)<br>phenylamino)pyrimidin-2-ylamino)-2-(1-(2-<br>(dimethylamino)acetyl)piperidin-4-yl)-5-<br>isopropoxyisoindolin-1-one | MS (ES⁺): 724.3<br>(M + 1)⁺. | 0.033 |
| 11 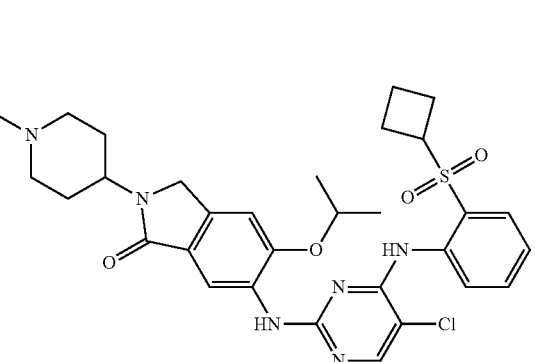<br>6-(5-chloro-4-(2-(cyclobutylsulfonyl)<br>phenylamino)pyrimidin-2-ylamino)-2-(1-(2-<br>(dimethylamino)acetyl)piperidin-4-yl)-5-<br>isopropoxyisoindolin-1-one | MS (ES⁺): 696.3<br>(M + 1)⁺. | 0.002 |

TABLE 1-continued

| | Structure | Physical Data ¹H NMR 400 MHz (DMSO-d6) and/or MS (m/z) | ALK IC50 (μM) |
|---|---|---|---|
| 12 | 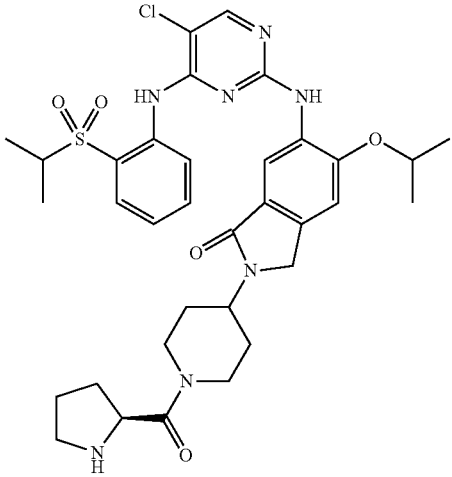 [SMILES: CC(C)Oc1cc2c(cc1Nc1ncc(Cl)c(Nc3ccccc3S(=O)(=O)C(C)C)n1)C(=O)N(C1CCN(C(=O)[C@@H]3CCCN3)CC1)C2](S)-6-(5-chloro-4-(2-(isopropylsulfonyl) phenylamino)pyrimidin-2-ylamino)-5-isopropoxy-2-(1-(pyrrolidine-2-carbonyl)piperidin-4-yl)isoindolin-1-one | MS (ES+): 696.2 (M + 1)+. | 0.029 |
| 13 | 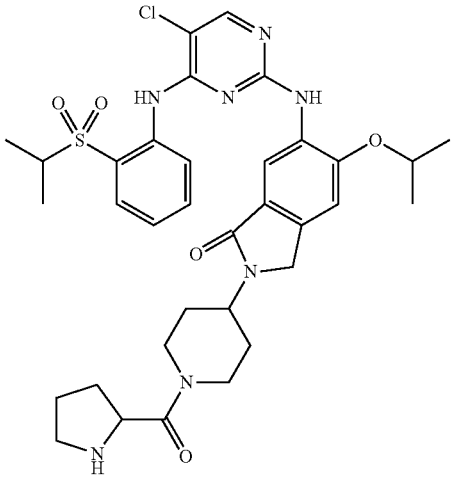 [SMILES: CC(C)Oc1cc2c(cc1Nc1ncc(Cl)c(Nc3ccccc3S(=O)(=O)C(C)C)n1)C(=O)N(C1CCN(C(=O)C3CCCN3)CC1)C2]6-(5-chloro-4-(2-(isopropylsulfonyl) phenylamino)pyrimidin-2-ylamino)-5-isopropoxy-2-(1-(pyrrolidine-2-carbonyl)piperidin-4-yl)isoindolin-1-one | MS (ES+): 696.2 (M + 1)+. ¹H NMR (MeOD-d₄) δ 8.38 (d, 1H), 8.27 (s, 1H), 8.13 (s, 1H), 7.91 (dd, 1H), 7.72 (m, 1H), 7.42 (t, 1H), 7.28 (s, 1H), 4.79 (m, 2H), 4.69 (m, 2H), 4.47 (d, 2H), 4.39 (m, 1H), 4.05 (d, 1H), 3.45 (m, 1H), 3.35 (m, 2H), 2.91 (m, 1H), 2.55 (m, 1H), 2.11 (m, 3H), 1.96 (m, 2H), 1.82 (m, 2H), 1.37 (d, 6H), 1.24 (d, 6H). | |

| | Structure | Physical Data<br>$^1$H NMR 400<br>MHz (DMSO-d6)<br>and/or MS (m/z) | ALK<br>IC50<br>(μM) |
|---|---|---|---|
| 14 | 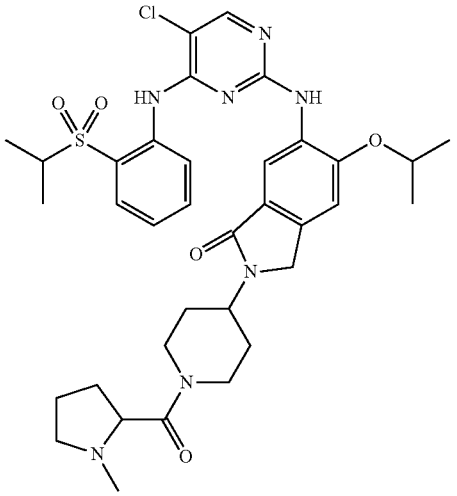 [SMILES: CC(C)Oc1cc2c(cc1Nc1ncc(Cl)c(Nc3ccccc3S(=O)(=O)C(C)C)n1)C(=O)N(C1CCN(C(=O)C3CCCN3C)CC1)C2]<br>6-(5-chloro-4-(2-(isopropylsulfonyl)<br>phenylamino)pyrimidin-2-ylamino)-5-<br>isopropoxy-2-(1-(1-methylpyrrolidine-2-<br>carbonyl)piperidin-4-yl)isoindolin-1-one | MS (ES$^+$): 710.2<br>(M + 1)$^+$.<br>$^1$H NMR (MeOD-d$_4$) δ<br>8.43 (m, 1H), 8.26 (m, 2H),<br>7.91 (m, 1H), 7.74 (m,<br>1H), 7.40 (m, 1H), 7.27<br>(d, 1H), 4.80 (m, 1H),<br>4.74 (m, 1H), 4.64<br>(m, 1H), 4.57 (m, 1H),<br>4.47 (s, 2H), 4.40<br>(m, 1H), 3.91 (m, 1H),<br>3.76 (m, 1H), 3.36 (m, 1H),<br>3.24 (m, 1H), 2.94 (d,<br>3H), 2, 67 (m, 1H), 2.25<br>(m, 1H), 2.11 (m,<br>2H), 1.97 (m, 3H), 1.85 (m,<br>2H), 1.38 (d,<br>6H), 1.25 (d, 6H). | 0.005 |
| 15 | 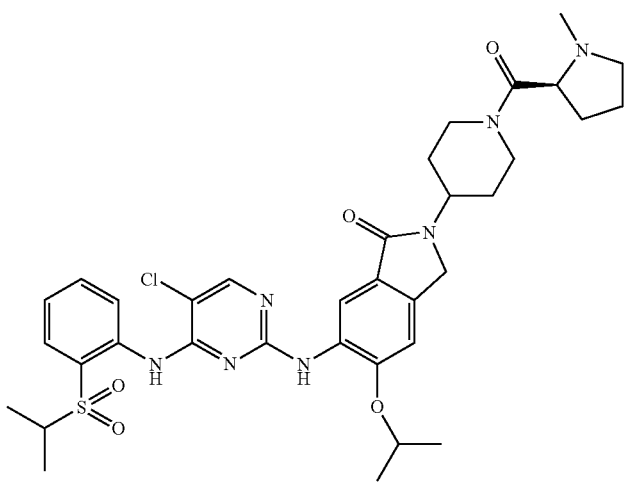 [SMILES: CC(C)Oc1cc2c(cc1Nc1ncc(Cl)c(Nc3ccccc3S(=O)(=O)C(C)C)n1)C(=O)N(C1CCN(C(=O)[C@@H]3CCCN3C)CC1)C2]<br>(S)-6-(5-chloro-4-(2-(isopropylsulfonyl)<br>phenylamino)pyrimidin-2-ylamino)-5-<br>isopropoxy-2-(1-(1-methylpyrrolidine-2-<br>carbonyl)piperidin-4-yl)isoindolin-1-one | MS (ES$^+$): 710.2<br>(M + 1)$^+$. | 0.023 |

TABLE 1-continued

| | Structure | Physical Data<br>¹H NMR 400<br>MHz (DMSO-d6)<br>and/or MS (m/z) | ALK<br>IC50<br>(μM) |
|---|---|---|---|
| 16 | 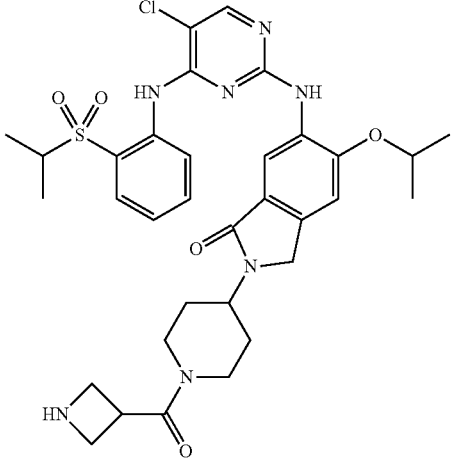 [SMILES: CC(C)Oc1cc2c(cc1Nc1ncc(Cl)c(Nc3ccccc3S(=O)(=O)C(C)C)n1)C(=O)N(C1CCN(C(=O)C3CNC3)CC1)C2]<br>2-(1-(azetidine-3-carbonyl)piperidin-4-yl)-6-(5-chloro-4-(2-(isopropylsulfonyl)phenylamino)pyrimidin-2-ylamino)-5-isopropoxyisoindolin-1-one | MS (ES+): 682.2 (M + 1)+.<br>¹H NMR (MeOD-d₄) δ 8.40 (d, 1H), 8.27 (s, 1H), 8.13 (s, 1H), 7.90 (dd, 1H), 7.72 (m, 1H), 7.41 (m, 1H), 7.28 (s, 1H), 4.80 (m, 1H), 4.74 (m, 1H), 4.46 (s, 2H), 4.39 (m, 2H), 4.28 (m, 3H), 4.12 (m, 1H), 3.77 (m, 1H), 3.36 (m, 1H), 3.26 (m, 1H0, 2.86 (m, 1H), 1.95 (m, 2H), 1.83 (m, 2H0, 1.37 (d, 6H), 1.26 (d, 6H). | 0.087 |
| 17 | 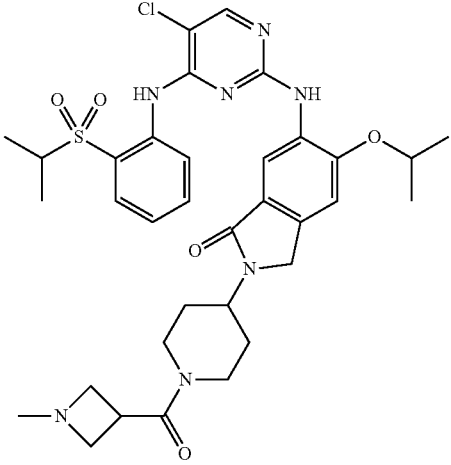 [SMILES: CC(C)Oc1cc2c(cc1Nc1ncc(Cl)c(Nc3ccccc3S(=O)(=O)C(C)C)n1)C(=O)N(C1CCN(C(=O)C3CN(C)C3)CC1)C2]<br>6-(5-chloro-4-(2-(isopropylsulfonyl)phenylamino)pyrimidin-2-ylamino)-5-isopropoxy-2-(1-(1-methylazetidine-3-carbonyl)piperidin-4-yl)isoindolin-1-one | MS (ES+): 696.2 (M + 1)+.<br>¹H NMR (MeOD-d₄) δ 8.44 (d, 1H), 8.24 (m, 2H), 7.91 (m, 1H), 7.73 (m, 1H), 7.39 (m, 1H), 7.26 (s, 1H), 4.80 (m, 1H), 4.73 (m, 1H), 4.56 (m, 2H), 4.44 (s, 2H), 4.37 (m, 1H), 4.27 (m, 1H), 4.17 (m, 3H), 3.79 (d, 1H), 3.26 (m, 1H), 2.96 (d, 3H), 2.87 (t, 1H), 1.97 (m, 2H), 1.83 (m, 2H), 1.38 (d, 6H), 1.25 (d, 6H). | 0.012 |

TABLE 1-continued
| Structure | Physical Data $^1$H NMR 400 MHz (DMSO-d6) and/or MS (m/z) | ALK IC50 (μM) |
|---|---|---|
| 18 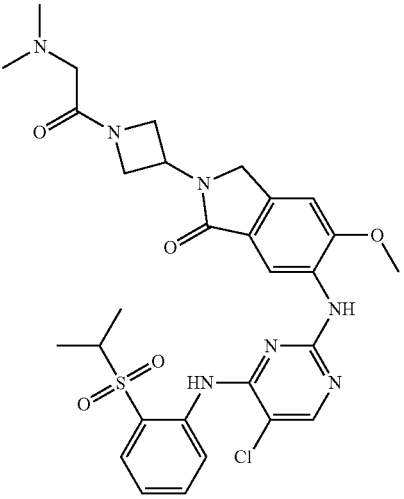 6-(5-chloro-4-(2-(isopropylsulfonyl) phenylamino)pyrimidin-2-ylamino)-2-(1-(2-(dimethylamino)acetyl)azetidin-3-yl)-5-methoxyisoindolin-1-one | MS (ES$^+$): 682.2 (M + 1)$^+$. | 0.006 |
| 19 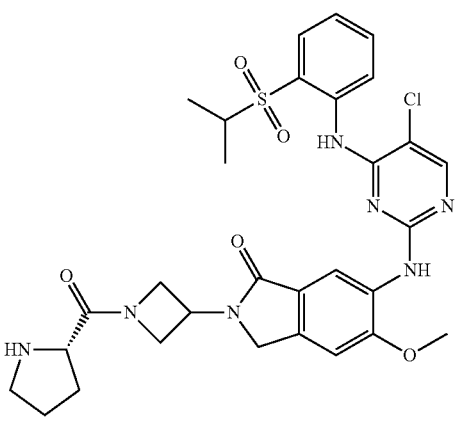 [SMILES: COc1cc2c(cc1Nc1ncc(Cl)c(Nc3ccccc3S(=O)(=O)C(C)C)n1)C(=O)N(C1CN(C(=O)[C@@H]3CCCN3)C1)C2] (S)-6-(5-chloro-4-(2-(isopropylsulfonyl) phenylamino)pyrimidin-2-ylamino)-5-methoxy-2-(1-(pyrrolidine-2-carbonyl)azetidin-3-yl)isoindolin-1-one | MS (ES$^+$): 640.2 (M + 1)$^+$. | 0.012 |

TABLE 1-continued

| Structure | Physical Data<br>¹H NMR 400<br>MHz (DMSO-d6)<br>and/or MS (m/z) | ALK<br>IC50<br>(μM) |
|---|---|---|
| 20 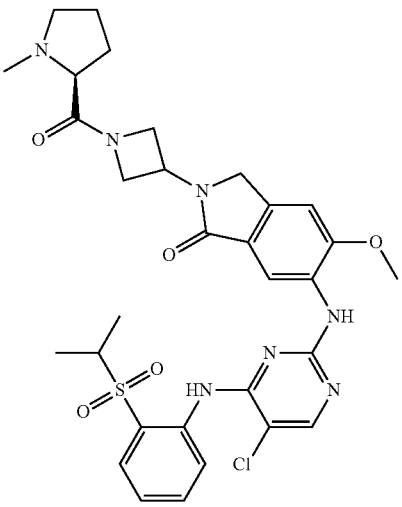<br>(S)-6-(5-chloro-4-(2-(isopropylsulfonyl)phenylamino)pyrimidin-2-ylamino)-5-methoxy-2-(1-(1-methylpyrrolidine-2-carbonyl)azetidin-3-yl)isoindolin-1-one | MS (ES⁺): 654.2<br>(M + 1)⁺. | 0.005 |
| 21 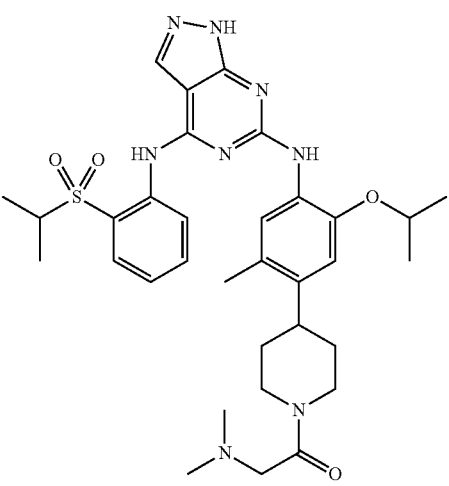 [SMILES: Cc1cc(Nc2nc(Nc3ccccc3S(=O)(=O)C(C)C)c3cn[nH]c3n2)c(OC(C)C)cc1C1CCN(C(=O)CN(C)C)CC1]<br>2-(dimethylamino)-1-(4-(5-isopropoxy-4-(4-(2-(isopropylsulfonyl)phenylamino)-1H-pyrazolo[3,4-d]pyrimidin-6-ylamino)-2-methylphenyl)piperidin-1-yl)ethanone | MS (ES⁺): 648.8<br>(M + 1)⁺. | 0.013 |

TABLE 1-continued

| Structure | Physical Data ¹H NMR 400 MHz (DMSO-d6) and/or MS (m/z) | ALK IC50 (μM) |
|---|---|---|
| 22 1,1,1-trifluoro-3-(4-(5-isopropoxy-4-(4-(2-(isopropylsulfonyl)phenylamino)-1H-pyrazolo[3,4-d]pyrimidin-6-ylamino)-2-methylphenyl)piperidin-1-yl)propan-2-ol | MS (ES⁺): 675.8 (M + 1)⁺. | 0.029 |
| 23 1,1,1-trifluoro-3-(4-(4-(4-(2-(isopropylsulfonyl)phenylamino)-1H-pyrazolo[3,4-d]pyrimidin-6-ylamino)-5-methoxy-2-methylphenyl)piperidin-1-yl)propan-2-ol | MS (ES⁺): 648.7 (M + 1)⁺. | 0.048 |

EXAMPLE 8

2-bromo-1-(4-(5-isopropoxy-4-(4-(2-(isopropylsulfonyl)phenylamino)-3-methyl-1H-pyrazolo[3,4-d]pyrimidin-6-ylamino)-2-methylphenyl)piperidin-1-yl)ethanone (24)

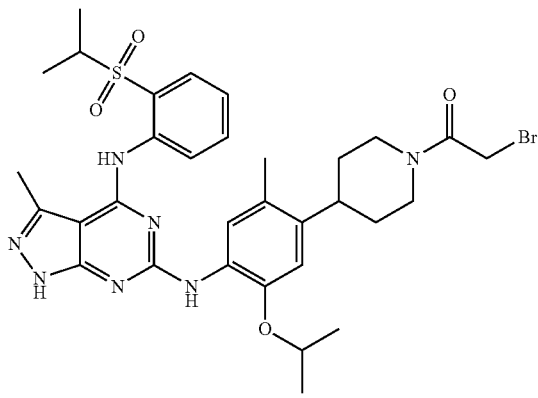 [SMILES: Cc1cc(Nc2nc(Nc3ccccc3S(=O)(=O)C(C)C)c3c(C)n[nH]c3n2)c(OC(C)C)cc1C1CCN(C(=O)CBr)CC1]

To a mixture of N6-(2-isopropoxy-5-methyl-4-(piperidin-4-yl)phenyl)-N4-(2-(isopropylsulfonyl)phenyl)-3-methyl-1H-pyrazolo[3,4-d]pyrimidine-4,6-diamine (50 mg, 0.087 mmol) in $CH_2Cl_2$ (3 mL) was added bromoacetyl chloride (10 uL, 0.095 mmol) dropwise at 0° C. The solvent was removed under reduced pressure and the residue was purified by silica gel chromatography, eluting with a gradient of EtOAc/hexane (0-100%) to give the title compound (2-bromo-1-(4-(5-isopropoxy-4-(4-(2-(isopropylsulfonyl)phenylamino)-3-methyl-1H-pyrazolo[3,4-d]pyrimidin-6-ylamino)-2-methylphenyl)piperidin-1-yl)ethanone) as a light yellow solid. MS: m/z=698.2 (M+1).

EXAMPLE 9

1-(4-(5-isopropoxy-4-(4-(2-(isopropylsulfonyl)phenylamino)-3-methyl-1H-pyrazolo[3,4-d]pyrimidin-6-ylamino)-2-methylphenyl)piperidin-1-yl)-2-(piperidin-1-yl)ethanone (29)

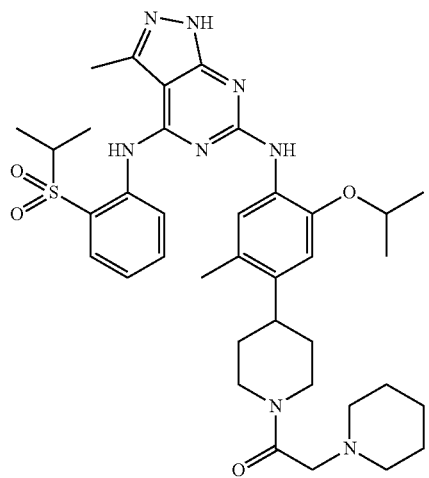 [SMILES: Cc1cc(Nc2nc(Nc3ccccc3S(=O)(=O)C(C)C)c3c(C)n[nH]c3n2)c(OC(C)C)cc1C1CCN(C(=O)CN2CCCCC2)CC1]

A mixture of 2-bromo-1-(4-(5-isopropoxy-4-(4-(2-(isopropylsulfonyl)phenylamino)-3-methyl-1H-pyrazolo[3,4-d]pyrimidin-6-ylamino)-2-methylphenyl)piperidin-1-yl)ethanone from Example 8 (10 mg, 0.014 mmol), and piperidine (3 uL, 0.031 mmol) in DMF was stirred at rt overnight. The crude mixture was directly purified by reverse phase HPLC to give 1-(4-(5-isopropoxy-4-(4-(2-(isopropylsulfonyl)phenylamino)-3-methyl-1H-pyrazolo[3,4-d]pyrimidin-6-ylamino)-2-methylphenyl)piperidin-1-yl)-2-(piperidin-1-yl)ethanone. MS: m/z=703.4 (M+1), 352.2 (M/2+1). 1H-NMR (400 MHz, CD3OD): δ=8.39 (brs, 1H), 7.98 (dd, 1H, J=1.6, 8.0 Hz), 7.70 (t, 1H, J=7.6 Hz), 7.53-7.49 (m, 2H), 6.88 (s, 1H), 4.73-4.69 (m, 1H), 4.62 (sept, 1H, J=6.0 Hz), 4.31 (d, 1H, J=16.4 Hz), 4.22 (d, 1H, J=16.4 Hz), 3.85-3.82 (m, 1H), 3.60 (t, 2H, J=12.0 Hz), 3.41-3.25 (m, 2H), 3.11-3.00 (m, 3H), 2.90-2.84 (m, 1H), 2.79 (s, 3H), 2.22 (s, 3H), 1.99-1.85 (m, 7H), 1.80-1.54 (m, 3H), 1.27 (d, 6H, J=6.0 Hz), 1.24 (d, 6H, J=6.8 Hz).

EXAMPLE 10

$N^6$-(2-isopropoxy-5-methyl-4-(piperidin-4-yl)phenyl)-$N^4$-(2-(isopropylsulfonyl)phenyl)-3-methyl-1H-pyrazolo[3,4-d]pyrimidine-4,6-diamine (33)

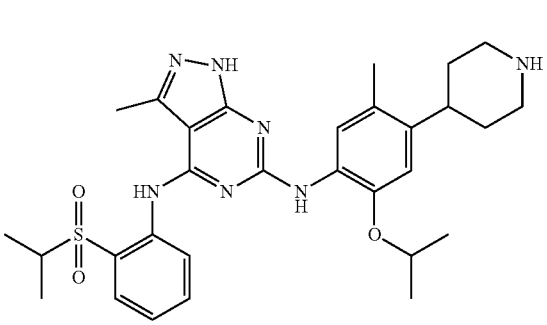 [SMILES: Cc1cc(Nc2nc(Nc3ccccc3S(=O)(=O)C(C)C)c3c(C)n[nH]c3n2)c(OC(C)C)cc1C1CCNCC1]

To a solution of tert-butyl 4-(4-(5-acetyl-4-chloro-6-(2-(isopropylsulfonyl)phenylamino)pyrimidin-2-ylamino)-5-isopropoxy-2-methylphenyl)piperidine-1-carboxylate (81 mg, 0.12 mmol) in EtOH (2 mL) was added hydrazine dichloride (36 mg, 0.34 mmoL) and sodium acetate (47 mg, 0.57 mmol) sequentially, and the reaction mixture was heated at 80° C. overnight. The reaction was cooled to room temperature and concentrated in vacuo. The crude was dissolved in the solution of TFA (2 mL) in DCM (2 mL), and the reaction was stirred for 30 min, followed by concentration and purification by RP-HPLC to afford N6-(2-isopropoxy-5-methyl-4-(piperidin-4-yl)phenyl)-N4-(2-(isopropylsulfonyl)phenyl)-3-methyl-1H-pyrazolo[3,4-d]pyrimidine-4,6-diamine. MS (ES+): 578.3 (MH+).

EXAMPLE 11

$N^6$-(2-isopropoxy-5-methyl-4-(1-methylpiperidin-4-yl)phenyl)-$N^4$-(2-(isopropylsulfonyl)phenyl)-3-methyl-1H-pyrazolo[3,4-d]pyrimidine-4,6-diamine (34)

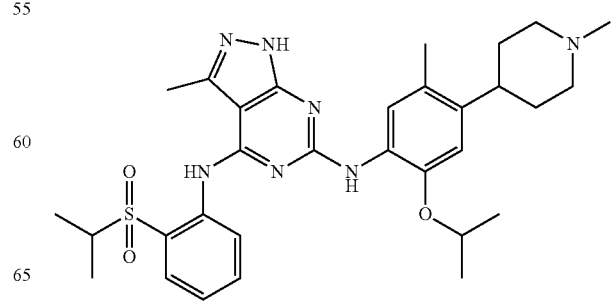

To a solution of N6-(2-isopropoxy-5-methyl-4-(piperidin-4-yl)phenyl)-N4-(2-(isopropylsulfonyl)phenyl)-3-methyl-1H-pyrazolo[3,4-d]pyrimidine-4,6-diamine (39 mg, 0.067 mmol) in 5.0 mL of MeOH and 5.0 mL of THF was added drops of AcOH and HCHO [1N in MeOH and THF (v/v: 1/1), 0.12 mmol, 120 µL] sequentially. The reaction mixture was stirred at room temperature for 30 min, then NaB(CN)H₃ (6.6 mg, 0.12 mmol) was added and the reaction mixture was stirred for another 1 h. Saturated aqueous NH₄Cl was added to the reaction and the reaction mixture was concentrated in vacuo. The crude was partitioned between EtOAc and brine. The organic extracts were concentrated and purified by RP-HPLC to afford N6-(2-isopropoxy-5-methyl-4-(1-methylpiperidin-4-yl)phenyl)-N4-(2-(isopropylsulfonyl)phenyl)-3-methyl-1H-pyrazolo[3,4-d]pyrimidine-4,6-diamine. MS (ES+): 592.3 (MH+).

EXAMPLE 12

2-(4-(5-isopropoxy-4-(4-(2-(isopropylsulfonyl)phenylamino)-3-methyl-1H-pyrazolo[3,4-d]pyrimidin-6-ylamino)-2-methylphenyl)piperidin-1-yl)acetamide (35)

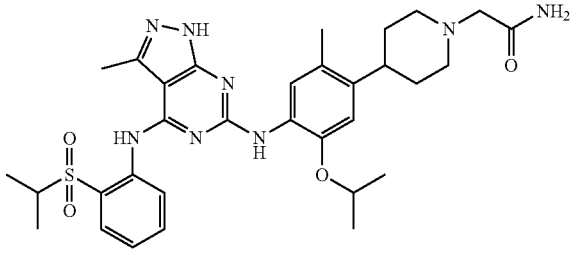 [SMILES: Cc1cc(Nc2nc(Nc3ccccc3S(=O)(=O)C(C)C)c3c(C)n[nH]c3n2)c(OC(C)C)cc1C1CCN(CC(N)=O)CC1]

The mixture of N6-(2-isopropoxy-5-methyl-4-(piperidin-4-yl)phenyl)-N4-(2-(isopropylsulfonyl)phenyl)-3-methyl-1H-pyrazolo[3,4-d]pyrimidine-4,6-diamine (20 mg, 0.035 mmol), 2-bromoacetamide (0.1 N in DMF, 0.035 mmol, 0.35 mL) and triethylamine (0.1 N in DMF, 0.105 mmol, 1.05 mL) was heated at 100° C. for 10 min. The resulting reaction mixture was purified by RP-HPLC to afford 2-(4-(5-isopropoxy-4-(4-(2-(isopropylsulfonyl)phenylamino)-3-methyl-1H-pyrazolo[3,4-d]pyrimidin-6-ylamino)-2-methylphenyl)piperidin-1-yl)acetamide. MS (ES+): 635.3 (MH+).

EXAMPLE 13

2-(4-(5-isopropoxy-4-(4-(2-(isopropylsulfonyl)phenylamino)-3-methyl-1H-pyrazolo[3,4-d]pyrimidin-6-ylamino)-2-methylphenyl)piperidin-1-yl)-N-methylacetamide (36)

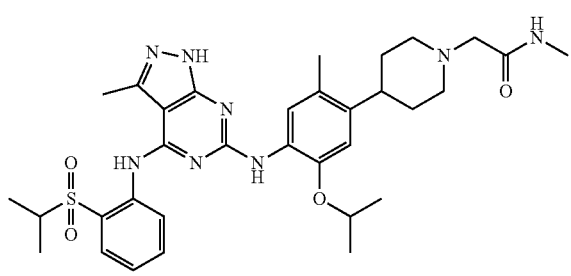 [SMILES: CNC(=O)CN1CCC(c2cc(OC(C)C)c(Nc3nc(Nc4ccccc4S(=O)(=O)C(C)C)c4c(C)n[nH]c4n3)cc2C)CC1]

The mixture of N6-(2-isopropoxy-5-methyl-4-(piperidin-4-yl)phenyl)-N4-(2-(isopropylsulfonyl)phenyl)-3-methyl-1H-pyrazolo[3,4-d]pyrimidine-4,6-diamine (20 mg, 0.035 mmol), 2-bromoacetamide (0.1 N in DMF, 0.070 mmol, 0.70 mL) and triethylamine (1.0 N in DMF, 0.105 mmol, 0.105 mL) was heated at 100° C. for 10 min. The resulting reaction mixture was purified by RP-HPLC to afford 2-(4-(5-isopropoxy-4-(4-(2-(isopropylsulfonyl)phenylamino)-3-methyl-1H-pyrazolo[3,4-d]pyrimidin-6-ylamino)-2-methylphenyl)piperidin-1-yl)-N-methylacetamide. MS (ES+): 649.3 (MH+).

EXAMPLE 14

2-(4-(5-isopropoxy-4-(4-(2-(isopropylsulfonyl)phenylamino)-3-methyl-1H-pyrazolo[3,4-d]pyrimidin-6-ylamino)-2-methylphenyl)piperidin-1-yl)ethanol (37)

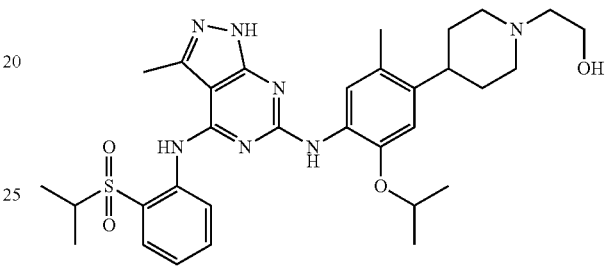

The mixture of N6-(2-isopropoxy-5-methyl-4-(piperidin-4-yl)phenyl)-N4-(2-(isopropylsulfonyl)phenyl)-3-methyl-1H-pyrazolo[3,4-d]pyrimidine-4,6-diamine (20 mg, 0.035 mmol), 2-bromoethanol (0.1 N in DMF, 0.070 mmol, 0.70 mL) and triethylamine (0.1 N in DMF, 0.18 mmol, 1.75 mL) was heated at 100° C. for 10 min. The resulting reaction mixture was purified by RP-HPLC to afford 2-(4-(5-isopropoxy-4-(4-(2-(isopropylsulfonyl)phenylamino)-3-methyl-1H-pyrazolo[3,4-d]pyrimidin-6-ylamino)-2-methylphenyl)piperidin-1-yl)ethanol. MS (ES+): 622.3 (MH+).

EXAMPLE 15

$N^6$-(2-isopropoxy-4-(1-(2-methoxyethyl)piperidin-4-yl)-5-methylphenyl)-$N^4$-(2-(isopropylsulfonyl)phenyl)-3-methyl-1H-pyrazolo[3,4-d]pyrimidine-4,6-diamine (38)

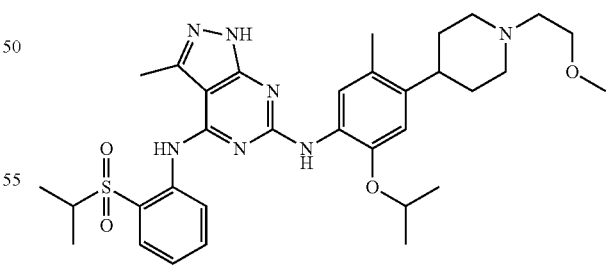

The mixture of N6-(2-isopropoxy-5-methyl-4-(piperidin-4-yl)phenyl)-N4-(2-(isopropylsulfonyl)phenyl)-3-methyl-1H-pyrazolo[3,4-d]pyrimidine-4,6-diamine (26.6 mg, 0.046 mmol), 1-bromo-2-methoxyethane (1.0 N in DMF, 0.46 mmol, 0.46 mL), and triethylamine (1.0 N in DMF, 0.46 mmol, 0.46 mL) was heated at 100° C. for 10 min The resulting reaction mixture was purified by RP-HPLC to afford N6-(2-isopropoxy-4-(1-methoxyethyl)piperidin-4-yl)-5-methylphenyl)-N4-(2-(isopropylsulfonyl)phenyl)-3-methyl-1H-pyrazolo[3,4-d]pyrimidine-4,6-diamine. MS (ES+): 636.3 (MH+).

EXAMPLE 16

2-(6-(2-isopropoxy-5-methyl-4-(1-methylpiperidin-4-yl)phenylamino)-3-methyl-1H-pyrazolo[3,4-d]pyrimidin-4-ylamino)-N,N-dimethylbenzenesulfonamide (39)

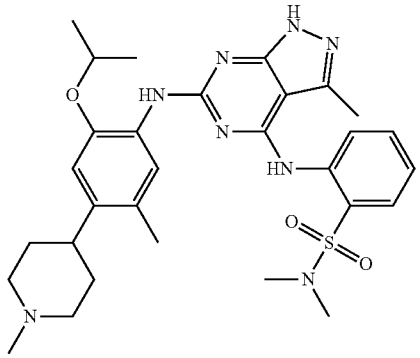 [SMILES: Cc1cc(Nc2nc(Nc3ccccc3S(=O)(=O)N(C)C)c3c(C)n[nH]c3n2)c(OC(C)C)cc1C1CCN(C)CC1]

4-hydroxy-3-methyl-6-mercaptopyrazolo[3,4-d]pyrimidine

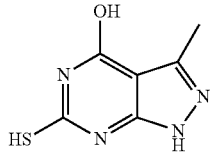

This reagent was prepared according to the method described in literature: J. med. Chem. 33:2174-8 (1990).

4-hydroxy-3-methyl-6-methylmercaptopyrazolo[3,4-d]pyrimidine

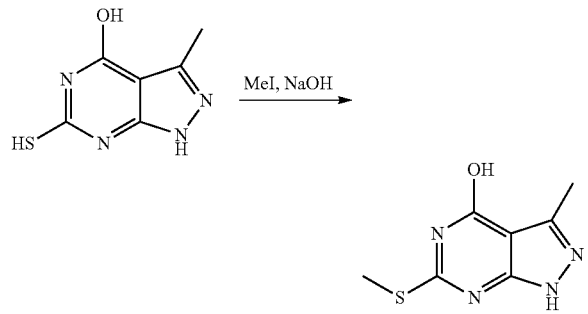

4-hydroxy-6-mercapto-3-methylpyrazolo[3,4-d]pyrimidine (14 g) was dissolved in a solution of 10 g. of sodium hydroxide in 300 ml. of water. The solution was cooled to 5° C. and shaken with 12 g. of methyl iodide. After 15-20 minutes, the solution was charcoaled, filtered and acidified with acetic acid to yield 12 g. of crude product. Recrystallization in acidic acid gave the product. MS (ES+): 197.0 (M+1)+.

4-chloro-3-methyl-6-methylmercaptopyrazolo[3,4-d]pyrimidine

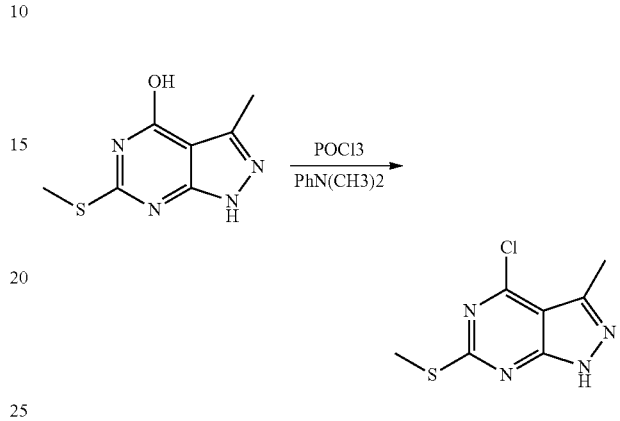

To 40 mL of phosphorus oxychloride and 3 mL. of dimethylaniline is added 2.2 g of crude 4-hydroxy-3-methyl-6-methylmercaptopyrazolo[3,4-d]pyrimidine. The solution was refluxed for 30-60 minutes when all the solid had dissolved. The excess phosphorus was removed under reduced pressure. The residue was poured with vigorous stirring onto a mixture of ice water. After ten minutes, the aqueous solution was extracted with ether. The ether solution was washed with cold water and dried with anhydrous sodium sulfate. The product was obtained after filtering and removing ether under reduced pressure. 215.0 (M+1)+.

N,N-dimethyl-2-(3-methyl-6-(methylthio)-1H-pyrazolo[3,4-d]pyrimidin-4-ylamino)benzenesulfonamide

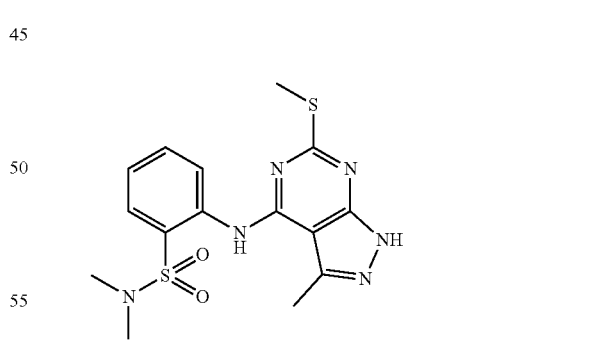

A solution of 4-chloro-3-methyl-6-methylmercaptopyrazolo[3,4-d]pyrimidine (10 mmol) and 2-(N,N-dimethylsulfonyl)aniline (10 mmol) in 100 mL of isopropanol was stirred at reflux for 1 hours. After cooling down to room temperature, triethylamine (12 mmol) was added to the reaction mixture, then the solution was heated under reflux for half hour. The product was obtained after workup and flash chromatography (hexane/EtOAc 4:1). 379.08 (M+1)+.

N,N-dimethyl-2-(3-methyl-6-(methylsulfonyl)-1H-pyrazolo[3,4-d]pyrimidin-4-ylamino)benzenesulfonamide

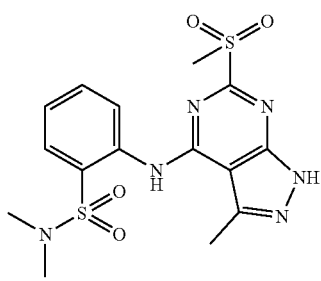 [SMILES: Cc1n[nH]c2nc(S(C)(=O)=O)nc(Nc3ccccc3S(=O)(=O)N(C)C)c12]

To a solution of N-(2-(N,N-dimethylsulfonyl)phenyl)-3-methyl-6-(methylthio)-1H-pyrazolo[3,4-d]pyrimidin-4-amine (1 mmol) in 10 mL of 1,2-dicholoroethane, was added MCPBA (3 mmol) at 0° C. The reaction mixture was warmed to room temperature and stirred for 1 hour. After work-up and flash chromatography, the product was obtained (CH$_2$Cl$_2$/MeOH 9:1). MS (ES+): 411.10 (M+1)+.

2-(6-(2-isopropoxy-5-methyl-4-(1-methylpiperidin-4-yl)phenylamino)-3-methyl-1H-pyrazolo[3,4-d]pyrimidin-4-ylamino)-N,N-dimethylbenzenesulfonamide

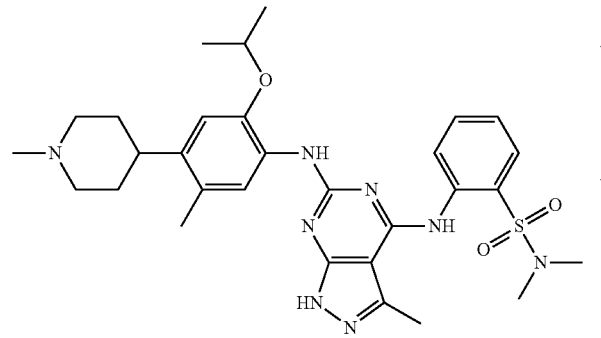

To a suspension of N-(2-(N,N-dimethylsulfonyl)phenyl)-3-methyl-6-(methylsulfonyl)-1H-pyrazolo[3,4-d]pyrimidin-4-amine (0.5 mmol) in 1 mL of isopropanol, was added 2-isopropoxy-5-methyl-4-(1-methylpiperidin-4-yl)aniline (0.5 mmol) and 4-methylbenzenesulfonic acid (0.5 mmol). The suspension was stirred at 150° C. for 3 hours. Product was obtained after work-up and prep-HPLC. 1H NMR (CDCl3, 400 MHz) δ 8.23-8.25 (d, 1H), 7.79-8.12 (m, 1H), 7.56 (s, 1H), 7.42-7.46(m, 1H), 7.28-7.32 (m, 1H), 6.77(s, 1H), 4.51-4.54 (m. 1H), 3.57-3.62 (m, 2H), 3.16-3.23 (m, 1H), 2.60-2.83(m, 11H), 2.54 (s, 3H), 2.38-2.47 (m, 3H), 2.04 (s, 3H), 1.86-1.95 (m, 2H), 1.25-1.27(d, 6H); MS (ES+): 593.18 (M+1)+.

EXAMPLE 17

N6-(2-isopropoxy-5-methyl-4-(1-methylpiperidin-4-yl)phenyl)-3-methyl-N4-(2-(methylsulfonyl)phenyl)-1H-pyrazolo[3,4-d]pyrimidine-4,6-diamine (40)

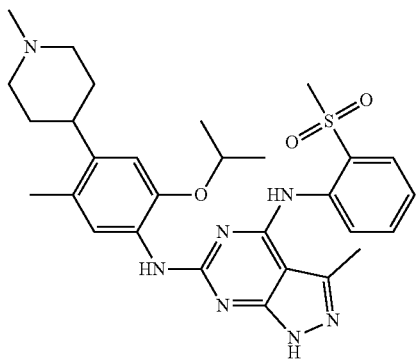 [SMILES: Cc1cc(Nc2nc(Nc3ccccc3S(C)(=O)=O)c3c(C)n[nH]c3n2)c(OC(C)C)cc1C1CCN(C)CC1]

This compound was prepared according to the method of Example 15 by replacing 2-(N,N-dimethylsulfonyl)aniline with 2-(methylsulfonyl)aniline

EXAMPLE 18

2-(dimethylamino)-1-(4-(5-isopropoxy-4-(4-(2-(isopropylsulfonyl)phenylamino)-3-methyl-1H-pyrazolo[3,4-d]pyrimidin-6-ylamino)-2-methylphenyl)piperidin-1-yl)ethanone (41)

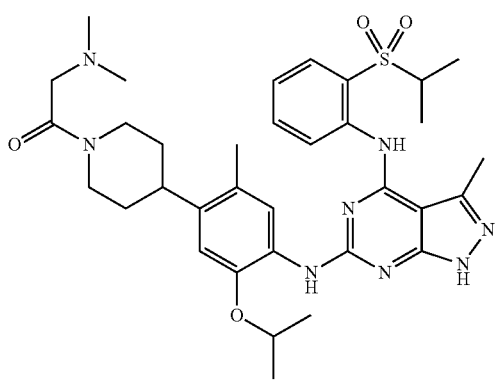 [SMILES: Cc1cc(Nc2nc(Nc3ccccc3S(=O)(=O)C(C)C)c3c(C)n[nH]c3n2)c(OC(C)C)cc1C1CCN(C(=O)CN(C)C)CC1]

This compound was prepared according to the method of Example 15 by replacing 2-(N,N-dimethylsulfonyl)aniline with 2-(isopropylsulfonyl)aniline, and replacing 2-isopropoxy-5-methyl-4-(1-methylpiperidin-4-yl)aniline with 1-(4-(4-amino-5-isopropoxy-2-methylphenyl)piperidin-1-yl)-2-(dimethylamino)ethanone.

EXAMPLE 19

N6-(2-isopropoxy-5-methyl-4-(1-methylpiperidin-4-yl)phenyl)-N4-(2-(isopropylsulfonyl)phenyl)-1H-pyrazolo[3,4-d]pyrimidine-3,4,6-triamine (42)

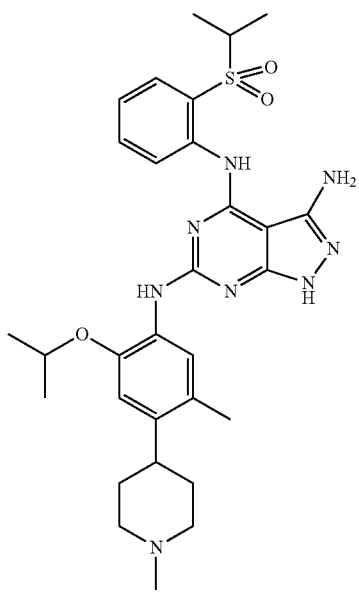 [SMILES: Cc1cc(Nc2nc(Nc3ccccc3S(=O)(=O)C(C)C)c3c(N)n[nH]c3n2)c(OC(C)C)cc1C1CCN(C)CC1]

2,4-dichloro-6-(2-(isopropylsulfonyl)phenylamino)pyrimidine-5-carbonitrile

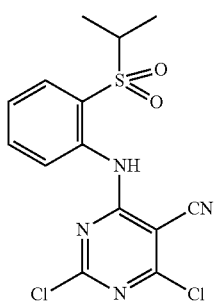 [SMILES: CC(C)S(=O)(=O)c1ccccc1Nc1nc(Cl)nc(Cl)c1C#N]

To a solution of 2,4,6-trichloropyrimidine-5-carbonitrile (1.0 mmol) and 2-(isopropylsulfonyl)aniline (1.0 mmol) in 5 mL of DMF, was added sodium hydride (24 mg). The suspension was stirred at 30° C. for 2 hours. Product was obtained after work-up and column chromatography (9:1 Hexane:EtOAc). MS (ES+): 371.01 (M+1)+.

4-chloro-2-(2-isopropoxy-5-methyl-4-(1-methylpiperidin-4-yl)phenylamino)-6-(2-(isopropylsulfonyl)phenylamino)pyrimidine-5-carbonitrile

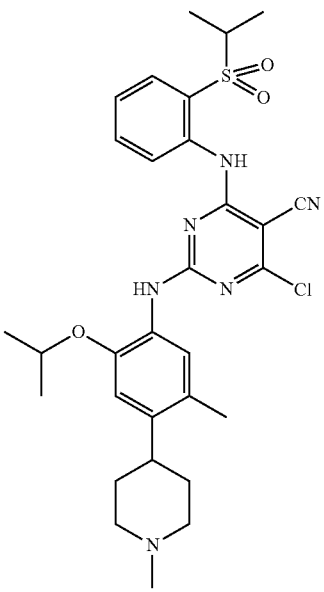 [SMILES: Cc1cc(Nc2nc(Cl)c(C#N)c(Nc3ccccc3S(=O)(=O)C(C)C)n2)c(OC(C)C)cc1C1CCN(C)CC1]

To a solution of 2,4-dichloro-6-(2-(isopropylsulfonyl)phenylamino)pyrimidine-5-carbonitrile (0.5 mmol) and 2-isopropoxy-5-methyl-4-(1-methylpiperidin-4-yl)aniline (0.5 mmol) in 3 mL of isopropanol, was added 4-methylbenzenesulfonic acid (0.5 mmol). The suspension was stirred at 120° C. for 2 hours. Product was obtained after work-up and prep-HPLC. MS (ES+): 597.23 (M+1)+.

N6-(2-isopropoxy-5-methyl-4-(1-methylpiperidin-4-yl)phenyl)-N4-(2-(isopropylsulfonyl)phenyl)-1H-pyrazolo[3,4-d]pyrimidine-3,4,6-triamine (20)

To a solution of 4-chloro-2-(2-isopropoxy-5-methyl-4-(1-methylpiperidin-4-yl)phenylamino)-6-(2-(isopropylsulfonyl)phenylamino)pyrimidine-5-carbonitrile (0.1 mmol) in 5 mL of isopropanol, was added hydrazine anhydrous (0.3 mmol). The solution was heated at 120° C. for 3 hours. Product was obtained after work-up and prep-HPLC. MS (ES+): 593.29 (M+1)+. 1H NMR (MeOD, 400 MHz) δ 8.01-8.03 (d, 1H), 7.83-7.86 (m, 1H), 7.31-7.43 (m, 3H), 6.91(s, 1H), 4.56-4.59 (m. 1H), 3.64-3.68 (m, 2H), 3.19-3.24 (m, 3H), 2.93(s, 3H), 2.25 (s, 3H), 2.02-2.07 (m, 4H), 1.17-1.32 (m, 12H); MS (ES+): 593.18 (M+1)+.

EXAMPLE 20

N6-(2-isopropoxy-4-(1-(2-methoxyethyl)piperidin-4-yl)-5-methylphenyl)-N4-(2-(isopropylsulfonyl)phenyl)-3-phenyl-1H-pyrazolo[3,4-d]pyrimidine-4,6-diamine (43)

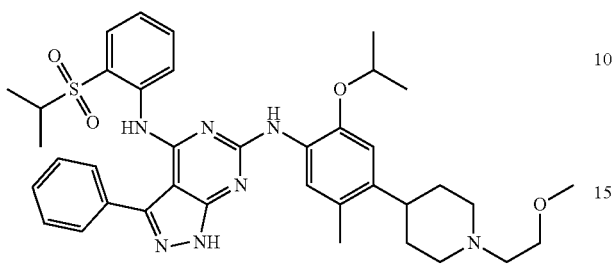

(2,4-dichloro-6-(2-(isopropylsulfonyl)phenylamino)pyrimidin-5-yl)(phenyl)methanone

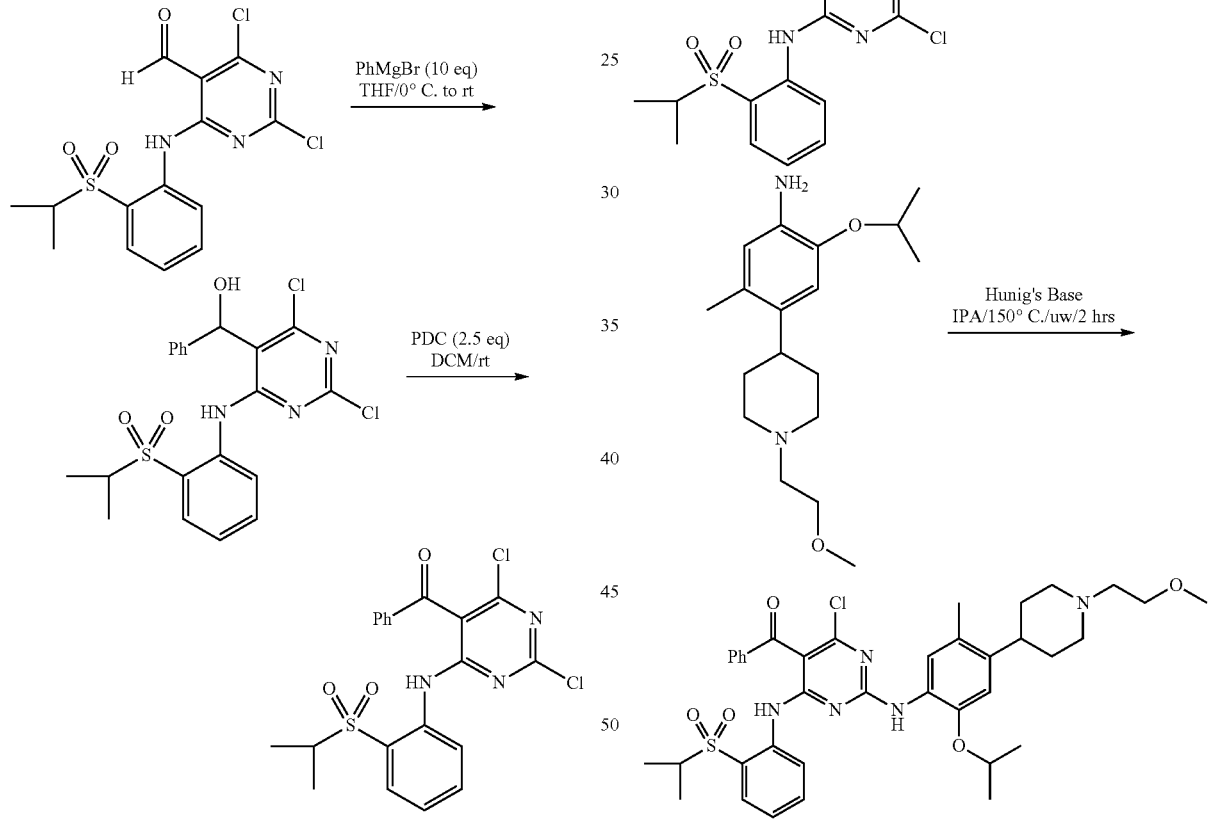

To the solution of 2,4-dichloro-6-(2-(isopropylsulfonyl)phenylamino)pyrimidine-5-carbaldehyde (112.3 mg, 0.3 mmol) in THF (1.0 mL) was added phenylmagnesiumbromide (3.0 M in diethyl ether, 1.0 mL, 3.0 mmol) at 0° C. under argon atmosphere. After addition, the reaction mixture was slowly warmed to room temperature and further stirred overnight. To the reaction mixture was then added 2.0 mL of saturated aqueous NH$_4$Cl at 0° C., dissolved in EtOAc (50 mL) and washed with H$_2$O (10 mL) and brine (10 mL). The organic phase was dried over Na$_2$SO$_4$, concentrated in vacuo, and purified by silica gel chromatography (eluent: EtOAc in Hexanes: 0 to 33%) to afford (2,4-dichloro-6-(2-(isopropylsulfonyl)phenylamino)pyrimidin-5-yl)(phenyl)methanol as a colorless oil. MS (ES+): 452.0 (MH+).

To the solution of (2,4-dichloro-6-(2-(isopropylsulfonyl)phenylamino)pyrimidin-5-yl)(phenyl)methanol (113.4 mg, 0.25 mmol) in DCM (10 mL) was added PDC (236 mg, 0.63 mmol). The reaction mixture was stirred at room temperature overnight. The resulting mixture was then filtered through a pad of silica gel, and the pad was washed by 5% EtOAc in DCM (200 mL). The filtrate was concentrated in vacuo to afford (2,4-dichloro-6-(2-(isopropylsulfonyl)phenylamino)pyrimidin-5-yl)(phenyl)methanone as a colorless oil. MS (ES+): 450.0 (MH+).

(4-chloro-2-(2-isopropoxy-4-(1-(2-methoxyethyl)piperidin-4-yl)-5-methylphenylamino)-6-(2-(isopropylsulfonyl)phenylamino)pyrimidin-5-yl)(phenyl)methanone To a 10 mL microwave reaction tube, (2,4-dichloro-6-(2-(isopropylsulfonyl)phenylamino)pyrimidin-5-yl)(phenyl)methanone (24.1 mg, 0.0548 mmol), 2-isopropoxy-4-(1-(2-methoxyethyl)piperidin-4-yl)-5-methylaniline (16.8 mg, 0.0548 mmol), 2-propanol (4 mL) and Hunig's Base (3 drops) were added successively. The resulting mixture was stirred at 150° C. for 2 hours by using a microwave machine. The reaction solution concentrated in vacuo to afford crude (4-chloro-2-(2-isopropoxy-4-(1-(2-methoxyethyl)piperidin-4-yl)-5-methylphenylamino)-6-(2-(isopropylsulfonyl)phenylamino)pyrimidin-5-yl)(phenyl)methanone as a slightly yellow sticky oil. MS (ES+): 720.30 (MH+).

N6-(2-isopropoxy-4-(1-(2-methoxyethyl)piperidin-4-yl)-5-methylphenyl)-N4-(2-(isopropylsulfonyl)phenyl)-3-phenyl-1H-pyrazolo[3,4-d]pyrimidine-4,6-diamine

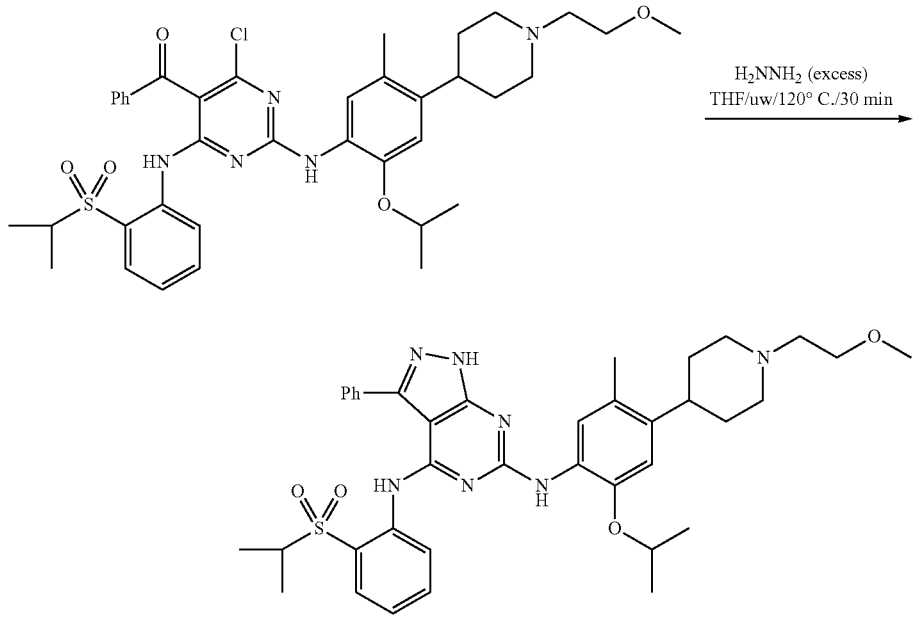

To a 10 mL microwave reaction tube was added (4-chloro-2-(2-isopropoxy-4-(1-(2-methoxyethyl)piperidin-4-yl)-5-methylphenylamino)-6-(2-(isopropylsulfonyl)phenylamino)pyrimidin-5-yl)(phenyl)methanone (0.0548 mmol), THF (4 mL) and H$_2$NNH$_2$ (0.4 mL). The resulting mixture was stirred at 120° C. for 30 minutes by using a microwave machine. The reaction solution was concentrated in vacuo and the residue was purified by reverse phase HPLC to afford N6-(2-isopropoxy-4-(1-(2-methoxyethyl)piperidin-4-yl)-5-methylphenyl)-N4-(2-(isopropylsulfonyl)phenyl)-3-phenyl-1H-pyrazolo[3,4-d]pyrimidine-4,6-diamine as a slightly yellow solid. MS (ES+): 698.30 (MH+).

Table 2 describes compounds which may be prepared following the methods described in the above examples.

TABLE 2

| | Structure | Physical Data<br>$^1$H NMR 400<br>MHz (DMSO-d6)<br>and/or MS (m/z) | ALK<br>IC50<br>(µM) |
|---|---|---|---|
| 24 | 2-bromo-1-(4-(5-isopropoxy-4-(4-(2-(isopropylsulfonyl)phenylamino)-3-methyl-1H-pyrazolo[3,4-d]pyrimidin-6-ylamino)-2-methylphenyl)piperidin-1-yl)ethanone | MS: m/z = 698.2 (M + 1). | |

TABLE 2-continued

| | Structure | Physical Data ¹H NMR 400 MHz (DMSO-d6) and/or MS (m/z) | ALK IC50 (μM) |
|---|---|---|---|
| 25 | 2-(dimethylamino)-1-(4-(4-(4-(2-(isopropylsulfonyl)phenylamino)-3-methyl-1H-pyrazolo[3,4-d]pyrimidin-6-ylamino)-5-methoxy-2-methylphenyl)piperidin-1-yl)ethanone | MS (ES+): 635.3 (M + 1)+. | 0.005 |
| 26 | 2-(dimethylamino)-1-(4-(5-isopropoxy-4-(4-(2-(isopropylsulfonyl)phenylamino)-3-methyl-1H-pyrazolo[3,4-d]pyrimidin-6-ylamino)-2-methylpheny)piperidin-1-yl)ethanone | MS (ES+): 663.3 (M + 1)+. | 0.007 |
| 27 | 1-(4-(5-isopropoxy-4-(4-(2-(isopropylsulfonyl)phenylamino)-3-methyl-1H-pyrazolo[3,4-d]pyrimidin-6-ylamino)-2-methylphenyl)piperidin-1-yl)-2-(1H-pyrazol-1-yl)ethanone | MS (ES+): 686.3 (M + 1)+. | 0.022 |

TABLE 2-continued

| | Structure | Physical Data ¹H NMR 400 MHz (DMSO-d6) and/or MS (m/z) | ALK IC50 (μM) |
|---|---|---|---|
| 28 | 2-(1H-imidazol-1-yl)-1-(4-(5-isopropoxy-4-(4-(2-(isopropylsulfonyl)phenylamino)-3-methyl-1H-pyrazolo[3,4-d]pyrimidin-6-ylamino)-2-methylphenyl)piperidin-1-yl)ethanone | MS (ES⁺): 686.3 (M + 1)⁺. | 0.029 |
| 29 | 1-(4-(5-isopropoxy-4-(4-(2-(isopropylsulfonyl)phenylamino)-3-methyl-1H-pyrazolo[3,4-d]pyrimidin-6-ylamino)-2-methylphenyl)piperidin-1-yl)-2-(piperidin-1-yl)ethanone | MS (ES⁺): 703.4 (M + 1)⁺. | |
| 30 | 1-(4-(5-isopropoxy-4-(4-(2-(isopropylsulfonyl)phenylamino)-3-methyl-1H-pyrazolo[3,4-d]pyrimidin-6-ylamino)-2-methylphenyl)piperidin-1-yl)-2-morpholinoethanone | MS (ES⁺): 705.4 (M + 1)⁺. | 0.041 |

TABLE 2-continued

| | Structure | Physical Data <sup>1</sup>H NMR 400 MHz (DMSO-d6) and/or MS (m/z) | ALK IC50 (μM) |
|---|---|---|---|
| 31 | 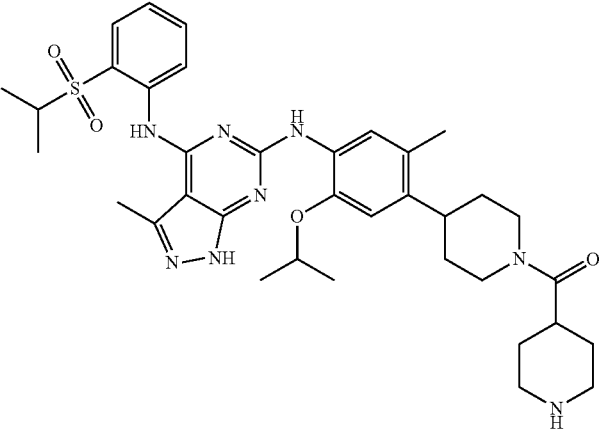 [SMILES: Cc1cc(Nc2nc(Nc3ccccc3S(=O)(=O)C(C)C)c3c(C)n[nH]c3n2)c(OC(C)C)cc1C1CCN(C(=O)C2CCNCC2)CC1]<br>(4-(5-isopropoxy-4-(4-(2-(isopropylsulfonyl)phenylamino)-3-methyl-1H-pyrazolo[3,4-d]pyrimidin-6-ylamino)-2-methylphenyl)piperidin-1-yl)(piperidin-4-yl)methanone | MS (ES$^+$): 689.4 (M + 1)$^+$. | 0.113 |
| 32 | 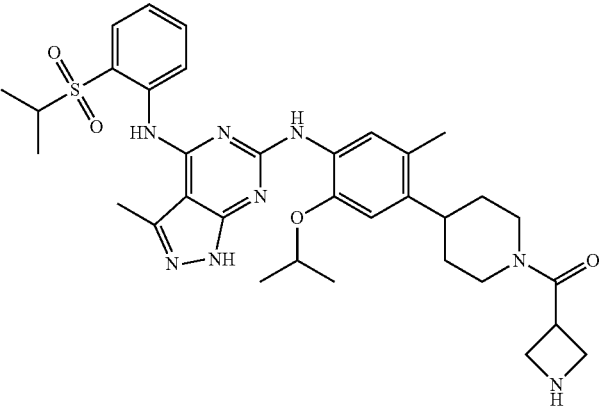 [SMILES: Cc1cc(Nc2nc(Nc3ccccc3S(=O)(=O)C(C)C)c3c(C)n[nH]c3n2)c(OC(C)C)cc1C1CCN(C(=O)C2CNC2)CC1]<br>azetidin-3-yl(4-(5-isopropoxy-4-(4-(2-(isopropylsulfonyl)phenylamino)-3-methyl-1H-pyrazolo[3,4-d]pyrimidin-6-ylamino)-2-methylphenyl)piperidin-1-yl)methanone | MS (ES$^+$): 661.3 (M + 1)$^+$. | |
| 33 | 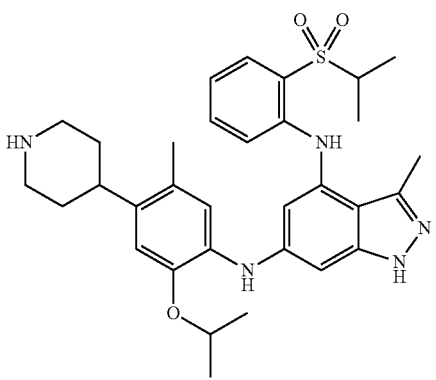 [SMILES: Cc1cc(Nc2cc(Nc3ccccc3S(=O)(=O)C(C)C)c3c(C)n[nH]c3c2)c(OC(C)C)cc1C1CCNCC1]<br>N6-(2-isopropoxy-5-methyl-4-(piperidin-4-yl)phenyl)-N4-(2-(isopropylsulfonyl)phenyl)-3-methyl-1H-pyrazolo[3,4-d]pyrimidine-4,6-diamine | MS (ES$^+$): 578.3 (M + 1)$^+$. | 0.038 |

TABLE 2-continued

| | Structure | Physical Data<br>¹H NMR 400 MHz (DMSO-d6) and/or MS (m/z) | ALK IC50 (μM) |
|---|---|---|---|
| 34 | N6-(2-isopropoxy-5-methyl-4-(1-methylpiperidin-4-yl)phenyl)-N4-(2-(isoproplsulfonyl)phenyl)-3-methyl-1H-pyrazolo[3,4-d]pyrimidine-4,6-diamine | MS (ES⁺): 592.3 (M + 1)⁺. | 0.020 |
| 35 | 2-(4-(5-isopropoxy-4-(4-(2-(isopropylsulfonyl)phenylamino)-3-methyl-1H-pyrazolo[3,4-d]pyrimidin-6-ylamino)-2-methylphenyl)piperidin-1-yl)acetamide | MS (ES⁺): 634.8 (M + 1)⁺. | 0.014 |
| 36 | 2-(4-(5-isopropoxy-4-(4-(2-(isopropylsulfonyl)phenylamino)-3-methyl-1H-pyrazolo(3,4-d]pyrimidin-6-ylamino)-2-methylphenyl)piperidin-1-yl)-N-methylacetamide | MS (ES⁺): 648.8 (M + 1)⁺. | 0.021 |

TABLE 2-continued

| | Structure | Physical Data $^1$H NMR 400 MHz (DMSO-d6) and/or MS (m/z) | ALK IC50 (μM) |
|---|---|---|---|
| 37 | 2-(4-(5-isopropoxy-4-(4-(2-(isopropylsulfonyl) phenylamino)-3-methyl-1H-pyrazolo[3,4-d]pyrimidin-6-ylamino)-2-methylphenyl)piperidin-1-yl)ethanol | HCl salt, δ 11.41 (s, 1H), 9.43 (s, 1H), 9.31 (s, 1H), 8.55 (d, J = 8.0 Hz, 1H), 7.99 (s, 1H), 7.85 (dd, J = 8.0, 1.6 Hz, 1H), 7.74-7.70 (m, 1H), 7.53 (s, 1H), 7.36-7.32 (m, 1H), 6.72 (s, 1H), 5.99 (s, 1H), 4.55-4.52 (m, 1H), 3.53-3.50 (m, 2H), 3.46-3.42 (m, 1H), 3.15-3.08 (m, 2H), 2.96-2.88 (m, 1H), 2.82 (d, J = 4.8 Hz, 3H), 2.31 (s, 3H), 2.17 (s, 3H), 1.92-1.81 (m, 4H), 1.31 (d, J = 6.0 Hz, 6H), 1.16 (d, J = 6.8 Hz, 6H). MS (ES$^+$): 621.3 (M + 1)$^+$. | 0.011 |
| 38 | N6-(2-isopropoxy-4-(1-(2-methoxyethyl)piperidin-4-yl)-5-methylphenyl)-N4-(2-(isopropylsulfonyl)phenyl)-3-methyl-1H-pyrazolo[3,4-d]pyrimidine-4,6-diamine | MS (ES$^+$): 636.3 (M + 1)$^+$. | 0.012 |
| 39 | 2-(6-(2-isopropoxy-5-methyl-4-(1-methyl-piperidin-4-yl)phenylamino)-3-methyl-1H-pyrazolo(3,4-d) pyrimidin-4-ylamino)-N,N-dimethylbenzenesulfonamide | MS (ES$^+$): 593.3 (M + 1)$^+$. | |

TABLE 2-continued

| Structure | Physical Data<br>¹H NMR 400 MHz (DMSO-d6) and/or MS (m/z) | ALK IC50 (μM) |
|---|---|---|
| 40 N6-(2-isopropoxy-5-methyl-4-(1-methyl-piperidin-4-yl)phenyl)-3-methyl-N4-(2-(methylsulfonyl)phenyl)-1H-pyrazolo[3,4-d]pyrimidine-4,6-diamine | MS (ES⁺): 564.3 (M + 1)⁺. | |
| 41 2-(dimethylamino)-1-(4-(5-isopropoxy-4-(4-(2-(isopropylsulfonyl)phenylamino)-3-methyl-1H-pyrazolo[3,4-d]pyrimidin-6-ylamino)-2-methylphenyl)piperidin-1-yl)ethanone | MS (ES⁺): 663.3 (M + 1)⁺. | |
| 42 N6-(2-isopropoxy-5-methyl-4-(1-methylpiperidin-4-yl)phenyl)-N4-(2-(isopropylsulfonyl)phenyl)-1H-pyrazolo[3,4-d]pyrimidine-3,4,6-triamine | MS (ES⁺): 593.3 (M + 1)⁺. | |

TABLE 2-continued

| | Structure | Physical Data ¹H NMR 400 MHz (DMSO-d6) and/or MS (m/z) | ALK IC50 (μM) |
|---|---|---|---|
| 43 | 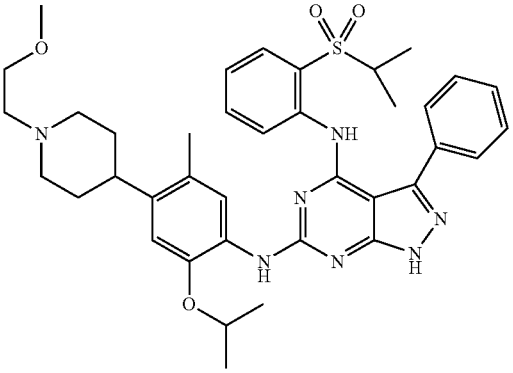 [SMILES: COCCN1CCC(c2cc(OC(C)C)c(Nc3nc(Nc4ccccc4S(=O)(=O)C(C)C)c4c(-c5ccccc5)n[nH]c4n3)cc2C)CC1] N6-(2-isopropoxy-4-(1-(2-methoxyethyl)piperidin-4-yl)-5-methylphenyl)-N4-(2-(isopropylsulfonyl)phenyl)-3-phenyl-1H-pyrazolo[3,4-d]pyrimidine-4,6-diamine | MS (ES+): 698.3 (M + 1)+. | 0.579 |
| 44 | 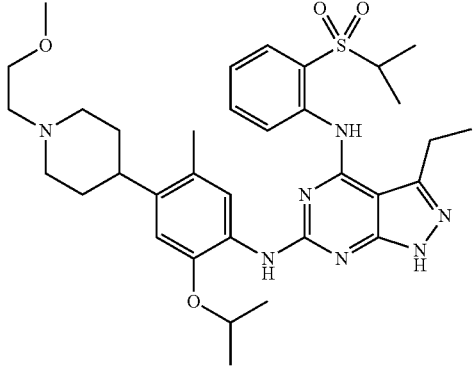 [SMILES: CCc1n[nH]c2nc(Nc3cc(C)c(C4CCN(CCOC)CC4)cc3OC(C)C)nc(Nc3ccccc3S(=O)(=O)C(C)C)c12] 3-ethyl-N6-(2-isopropoxy-4-(1-(2-methoxyethyl)piperidin-4-yl)-5-methylphenyl)-N4-(2-(isopropylsulfonyl)phenyl)-1H-pyrazolo[3,4-d]pyrimidine-4,6-diamine | MS (ES+): 650.3 (M + 1)+. | 0.181 |
| 45 | 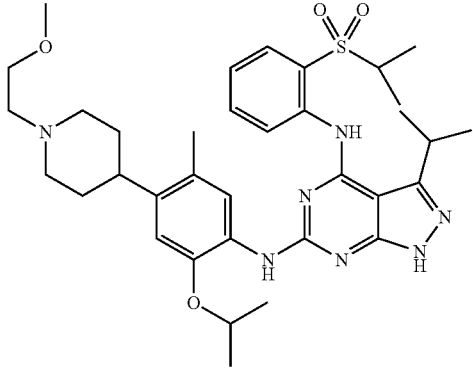 [SMILES: COCCN1CCC(c2cc(OC(C)C)c(Nc3nc(Nc4ccccc4S(=O)(=O)C(C)C)c4c(C(C)C)n[nH]c4n3)cc2C)CC1] N6-(2-isopropoxy-4-(1-(2-methoxyethyl)piperidin-4-yl)-5-methylphenyl)-3-isopropyl-N4-(2-(isopropylsulfonyl)phenyl)-1H-pyrazolo[3,4-d]pyrimidine-4,6-diamine | MS (ES+): 664.3 (M + 1)+. | |

TABLE 2-continued

| | Structure | Physical Data<br>¹H NMR 400 MHz (DMSO-d6) and/or MS (m/z) | ALK IC50 (μM) |
|---|---|---|---|
| 46 | N6-(2-isopropoxy-5-methyl-4-(1-(2-(methylsulfonyl)ethyl)piperidin-4-yl)phenyl)-N4-(2-(isopropylsulfonyl)phenyl)-3-methyl-1H-pyrazolo[3,4-d]pyrimidine-4,6-diamine | MS (ES⁺): 688.9 (M + 1)⁺. | 0.023 |
| 47 | 1-methylcyclopropyl 4-(5-isopropoxy-4-(4-(2-(isopropylsulfonyl)phenylamino)-3-methyl-1H-pyrazolo[3,4-d]pyrimidin-6-ylamino)-2-methylphenyl)piperidine-1-carboxylate | MS (ES⁺): 675.8 (M + 1)⁺. | |
| 48 | (4-(5-isopropoxy-4-(4-(2-(isopropylsulfonyl)phenylamino)-3-methyl-1H-pyrazolo[3,4-d]pyrimidin-6-ylamino)-2-methylphenyl)piperidin-1-yl)(piperidin-1-yl)methanone | MS (ES⁺): 688.8 (M + 1)⁺. | |

| | Structure | Physical Data ¹H NMR 400 MHz (DMSO-d6) and/or MS (m/z) | ALK IC50 (μM) |
|---|---|---|---|
| 49 | N4-(2-(isopropylsulfonyl)phenyl)-N6-(2-methoxy-5-methyl-4-(1-methylpiperidin-4-yl)phenyl)-3-methyl-1H-pyrazolo[3,4-d]pyrimidine-4,6-diamine | MS (ES$^+$): 563.7 (M + 1)$^+$. | 0.002 |
| 50 | N4-(2-(isopropylsulfonyl)phenyl)-N6-(2-methoxy-5-methyl-4-(piperidine-4-yl)phenyl)-3-methyl-1H-pyrazolo[3,4-d]pyrimidine-4,6-diamine | MS (ES$^+$): 549.8 (M + 1)$^+$. | 0.012 |
| 51 | benzyl 4-(5-isopropoxy-4-(4-(2-(isopropylsulfonyl)phenylamino)-3-methyl-1H-pyrazolo[3,4-d]pyrimidin-6-ylamino)-2-methylphenyl)piperidine-1-carboxylate | MS (ES$^+$): 711.3 (M + 1)$^+$. | |

TABLE 2-continued

| | Structure | Physical Data<br>¹H NMR 400 MHz (DMSO-d6) and/or MS (m/z) | ALK IC50 (μM) |
|---|---|---|---|
| 52 | 3-(4-(5-isopropoxy-4-(4-(2-(isopropylsulfonyl)phenylamino)-3-methyl-1H-pyrazolo[3,4-d]pyrimidin-6-ylamino)-2-methylphenyl)piperidin-1-yl)propanamide | MS (ES⁺): 648.8 (M + 1)⁺. | 0.018 |
| 53 | 1-(azetidin-1-yl)-3-(4-(5-isopropoxy-4-(4-(2-(isopropylsulfonyl)phenylamino)-3-methyl-1H-pyrazolo[3,4-d]pyrimidin-6-ylamino)-2-methylphenyl)piperidin-1-propan-1-one | MS (ES⁺): 688.9 (M + 1)⁺. | 0.021 |
| 54 | 3-(4-(5-isopropoxy-4-(4-(2-(isopropylsulfonyl)phenylamino)-3-methyl-1H-pyrazolo[3,4-d]pyrimidin-6-ylamino)-2-methylphenyl)piperidin-1-yl)-N,N-dimethylpropanamide | MS (ES⁺): 676.8 (M + 1)⁺. | 0.015 |

TABLE 2-continued

| | Structure | Physical Data $^1$H NMR 400 MHz (DMSO-d6) and/or MS (m/z) | ALK IC50 (μM) |
|---|---|---|---|
| 55 | 3-(4-(5-isopropoxy-4-(4-(2-(isopropylsulfonyl)phenylamino)-3-methyl-1H-pyrazolo(3,4-d]pyrimidin-6-ylamino)-2-methylphenyl)piperidin-1-yl)-N-methylpropanamide | MS (ES$^+$): 662.3 (M + 1)$^+$. | 0.025 |
| 56 | (R)-1,1,1-trifluoro-3-(4-(5-isopropoxy-4-(4-(2-(isopropylsulfonyl)phenylamino)-3-methyl-1H-pyrazolo[3,4-d]pyrimidin-6-ylamino)-2-methylphenyl)piperidin-1-yl)propan-2-ol | MS (ES$^+$): 690.8 (M + 1)$^+$. | 0.105 |
| 57 | (S)-1,1,1-trifluoro-3-(4-(5-isopropoxy-4-(4-(2-(isopropylsulfonyl)phenylamino)-3-methyl-1H-pyrazolo[3,4-d]pyrimidin-6-ylamino)-2-methylphenyl)piperidin-1-yl)propan-2-ol | MS (ES$^+$): 690.8 (M + 1)$^+$. | 0.087 |

TABLE 2-continued

| | Structure | Physical Data <br> ¹H NMR 400 MHz (DMSO-d6) and/or MS (m/z) | ALK IC50 (μM) |
|---|---|---|---|
| 58 | N5-(2-isopropoxy-5-methyl-4-(1-methylpiperidin-4-yl)phenyl)-N7-(2-(isopropylsulfonyl)phenyl)-1-methyl-1H-pyrazolo[4,3-d]pyrimidine-5,7-diamine | MS (ES⁺): 591.3 (M + 1)⁺. | |
| 59 | N4-(2-(isopropylsulfonyl)phenyl)-3-phenyl-N6-(4-(piperidin-4-yl)phenyl)-1H-pyrazolo[3,4-d]pyrmidine-4,6-diamine | MS: m/z = 505.6 (M + 1). | 0.017 |
| 60 | N4-(2-(isopropylsulfonyl)phenyl)-N6-(2-methoxy-5-methyl-4-(1-(2-(methylsulfonyl)ethyl)piperidin-4-yl)phenyl)-3-methyl-1H-pyrazolo[3,4-d]pyrimidine-4,6-diamine | MS: m/z = 655.8 (M + 1). | 0.043 |
| 61 | N6-(4-(1-ethylpyrrolidin-3-yl)phenyl)-N4-(2-(isopropylsulfonyl(phenyl)-3-methyl-1H-pyrazolo[3,4-d]pyrimidine-4,6-diamine | MS: m/z = 519.7 (M + 1). | 0.010 |

TABLE 2-continued

| | Structure | Physical Data<br>¹H NMR 400 MHz (DMSO-d6) and/or MS (m/z) | ALK IC50 (μM) |
|---|---|---|---|
| 62 | S-N4-(2-(isopropylsulfonyl)phenyl)-N6-(2-isopropoxy-5-methyl-4-(1-(3-(tetrahydrosulfonyl)piperidin-4-yl)phenyl)-3-methyl-1H-pyrazolo[3,4-d]pyrimidine-4,6-diamine | MS: m/z = 695.9 (M + 1). | 0.019 |
| 63 | R-N4-(2-(isopropylsulfonyl)phenyl)-N6-(2-isopropoxy-5-methyl-4-(1-(3-(tetrahydrosulfonyl)piperidin-4-yl)phenyl)-3-methyl-1H-pyrazolo[3,4-d]pyrimidine-4,6-diamine | MS: m/z = 695.9 (M + 1). | 0.018 |
| 64 | N4-(2-(isopropylsulfonyl)phenyl)-N6-(2-methoxy-5-methyl-4-(tetrahydro-2H-pyran-4-yl)phenyl)-3-methyl-1H-pyrazolo[3,4-d]pyrimidine-4,6-diamine | MS: m/z = 550.7 (M + 1). | 0.006 |

TABLE 2-continued

| | Structure | Physical Data <br> ¹H NMR 400 MHz (DMSO-d6) and/or MS (m/z) | ALK IC50 (μM) |
|---|---|---|---|
| 65 | 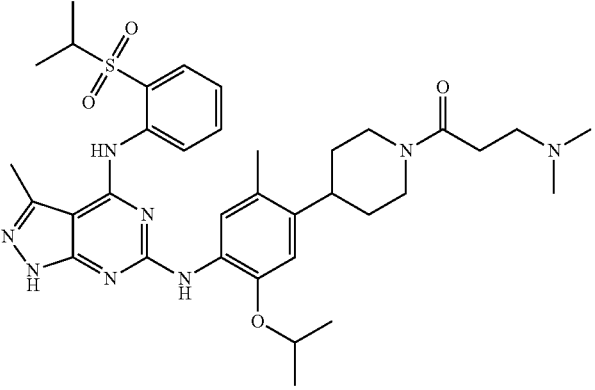 [SMILES: Cc1cc(Nc2nc(Nc3ccccc3S(=O)(=O)C(C)C)c3c(C)n[nH]c3n2)c(OC(C)C)cc1C1CCN(C(=O)CCN(C)C)CC1] <br> 3-(dimethylamino)-1-(4-(5-isopropoxy-4-(4-(2-(isopropylsulfonyl)phenylamino)-3-methyl-1H-pyrazolo[3,4-d]pyrimidin-6-ylamino)-2-methylphenyl)piperidin-1-yl)propan-1-one | MS: m/z = 676.9 (M + 1). | 0.018 |
| 66 | 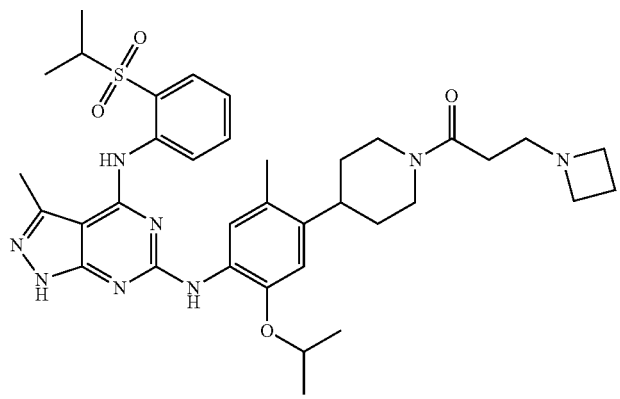 [SMILES: Cc1cc(Nc2nc(Nc3ccccc3S(=O)(=O)C(C)C)c3c(C)n[nH]c3n2)c(OC(C)C)cc1C1CCN(C(=O)CCN2CCC2)CC1] <br> 3-(azetidin-1-yl)-1-(4-(5-isopropoxy-4-(4-(2-(isopropylsulfonyl)phenylamino)-3-methyl-1H-pyrazolo[3,4-d]pyrimidin-6-ylamino)-2-methylphenyl)piperidin-1-yl)propan-1-one | MS: m/z = 688.9 (M + 1). | 0.046 |
| 67 | 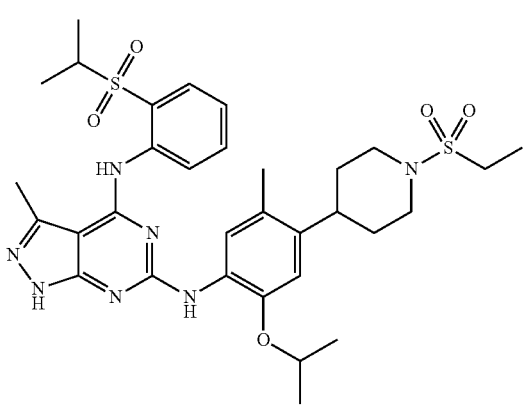 [SMILES: CCS(=O)(=O)N1CCC(c2cc(OC(C)C)c(Nc3nc(Nc4ccccc4S(=O)(=O)C(C)C)c4c(C)n[nH]c4n3)cc2C)CC1] <br> N6-(4-(1-(ethylsulfonyl)piperidin-4-yl)-2-isopropoxy-5-methylphenyl)-N4-(2-(isopropylsulfonyl)phenyl)-3-methyl-1H-pyrazolo[3,4-d]pyrimidine-4,6-diamine | MS: m/z = 669.8 (M + 1). | 0.092 |

EXAMPLE 21

N2-(2-isopropoxy-5-methyl-4-(piperidin-4-yl)phenyl)-N4-(2-(isopropylsulfonyl)phenyl)-5-methyl-7H-pyrrolo[2,3-d]pyrimidine-2,4-diamine (68)

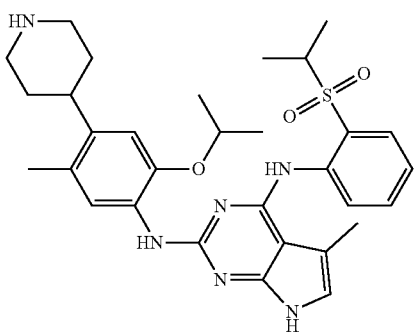 [SMILES: Cc1cc(Nc2nc(Nc3ccccc3S(=O)(=O)C(C)C)c3c(C)c[nH]c3n2)c(OC(C)C)cc1C1CCNCC1]

7H-pyrrolo[2,3-d]pyrimidine-2,4-diol

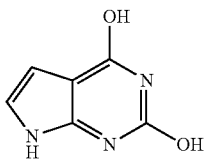 [SMILES: Oc1nc(O)c2cc[nH]c2n1]

To 40 g 6-aminopyrimidine-2,4-diol (1) (315 mmol) in 1.0 L of water was added 54.3 g NaOAc (662 mmol) and 48 mL of 2-chloroacetaldehyde (50 wt % in $H_2O$, 378 mmol). The resulting mixture was heated to reflux and stirred for three hours. The reaction mixture was cooled to room temperature followed by slow addition of 300 mL of 2N HCl in $H_2O$. The precipitate was filtered, washed with $H_2O$ and dried at 50° C. under vacuum to give the title compound.

2,4-dichloro-7H-pyrrolo[2,3-d]pyrimidine

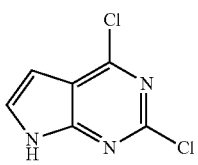 [SMILES: Clc1nc(Cl)c2cc[nH]c2n1]

11.5 g (76 mmol) 7H-pyrrolo[2,3-d]pyrimidine-2,4-diol (2a) was dissolved in 40 mL of toluene and 21.3 mL of $POCl_3$ (229 mmol) was slowly added at room temperature. The reaction mixture was heated to 70° C. and 26.5 mL of DIPEA (153 mmol) was added dropwise over a period of two hours under $N_2$. The reaction temperature was increased to 106° C. and the mixture stirred overnight. After cooling down to room temperature, the reaction mixture was poured into a mixture of 200 mL EtOAc and 300 mL water, then filtered through celite. The aqueous layer was extracted with 3×200 mL of EtOAc and the combined organic layers were washed with brine, decolored with activated carbon, filtered through celite and concentrated to give the title compound.

5-bromo-2,4-dichloro-7H-pyrrolo[2,3-d]pyrimidine

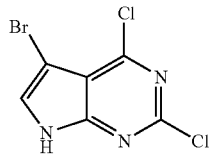 [SMILES: Clc1nc(Cl)c2c(Br)c[nH]c2n1]

To 935 mg 2,4-dichloro-7H-pyrrolo[2,3-d]pyrimidine (3a) (5.0 mmol) in 100 mL of 1,4-dioxane was slowly added 256 µL of $Br_2$ (5.0 mmol) at 0° C. over a period of 10 minutes. After stirring for 30 minutes at 0° C., the reaction mixture was poured into a mixture of 150 mL of EtOAc and 150 mL of saturated aqueous $Na_2SO_3$ then filtered through celite. The aqueous phase was extracted with EtOAc (3×100 mL) and combined organic layers were washed with brine, concentrated and purified by flash column chromatography to give the title compound.

2,4-dichloro-5-methyl-7H-pyrrolo[2,3-d]pyrimidine

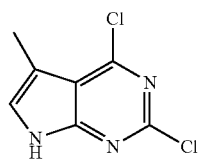

1.4 g 5-bromo-2,4-dichloro-7H-pyrrolo[2,3-d]pyrimidine (4) (5.2 mmol) was dissolved in 200 mL of THF. After cooling to −78° C., 9.75 mL of BuLi (1.6M solution in Hexanes, 15.6 mmol) was slowly added over a period of 30 minutes, then stirred for 30 minutes at −78° C. before 396 uL of MeI (6.24 mmol) was dropwise added into the reaction mixture over a period of one hour. The reaction mixture was stirred at −78° C. for one more hour and quenched by adding 20 mL of saturated aqueous $NH_4Cl$ solution at this temperature. The reaction mixture was then partitioned between 100 mL of saturated $NaHCO_3$ and 100 mL of EtOAc. The organic layer was separated and the aqueous layer is extracted with EtOAc (3×100 mL). Combined organic layers were washed with brine, dried over $Na_2SO_4$ and concentrated to give the crude title compound which was used without further purification.

2,4-dichloro-5-methyl-7-tosyl-7H-pyrrolo[2,3-d]pyrimidine

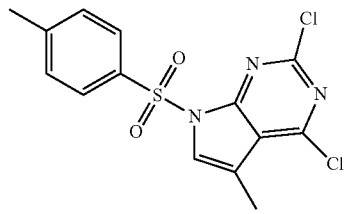 [SMILES: Cc1ccc(S(=O)(=O)n2cc(C)c3c(Cl)nc(Cl)nc32)cc1]

503 mg 2,4-dichloro-5-methyl-7H-pyrrolo[2,3-d]pyrimidine (5) (2.5 mmol) and 523 mg TsCl (2.75 mmol) were dissolved in 20 mL of DMF. After cooling to 0° C., 200 mg NaH (2.75 mmol) was slowly added under $N_2$. The reaction mixture was stirred at 0° C. for 30 minutes and quenched by adding 10 mL of 10% aqueous $NH_4Cl$ at this temperature, then extracted with EtOAc (3×50 mL). Combined organic layers were washed with brine, dried over $Na_2SO_4$ and purified by flash column chromatography to give the title compound as light yellow solid.

2-(isopropylthio)aniline

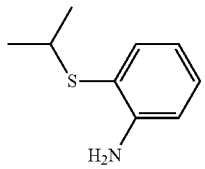

To 200 mL solution of 19.9 g 2-aminobenzenethiol (7) (159 mmol) and 17.4 mL of 2-iodopropane (175 mmol) in EtOH was slowly added 23.2 g KOBu-t (207 mmol) at 0° C. under N2. The reaction mixture was warmed up to room temperature and stirred for two hours, then filtered through celite and concentrated. The residue was redissolved in 300 mL of EtOAc, washed with water and then brine, concentrated and purified by flash column chromatography to give the title compound as light yellow oil.

2-chloro-N-(2-(isopropylthio)phenyl)-5-methyl-7-tosyl-7H-pyrrolo[2,3-d]pyrimidin-4-amine

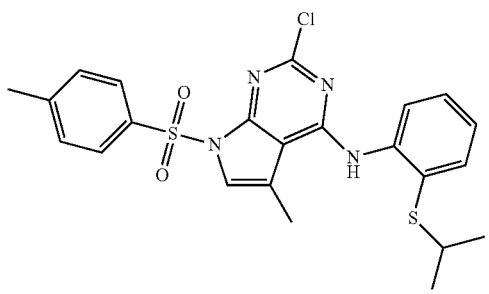 [SMILES: Cc1ccc(S(=O)(=O)n2cc(C)c3c(Nc4ccccc4SC(C)C)nc(Cl)nc32)cc1]

350 mg 2,4-dichloro-5-methyl-7-tosyl-7H-pyrrolo[2,3-d]pyrimidine (6) (1.0 mmol) and 255 mg 2-(isopropylthio)aniline (8) (1.5 mmol) were dissolved in 15 mL of DMF. 336 mg KOBu-t (3.0 mmol) was then slowly added under $N_2$. After stiffing for one hour at ambient temperature, the reaction mixture was poured into 100 mL of water and extracted with EtOAc (3×100 mL). Combined organic layers were washed with brine, dried over $Na_2SO_4$ and purified by flash column chromatography to give the title compound as white solid.

2-chloro-N-(2-(isopropylsulfonyl)phenyl)-5-methyl-7H-pyrrolo[2,3-d]pyrimidin-4-amine

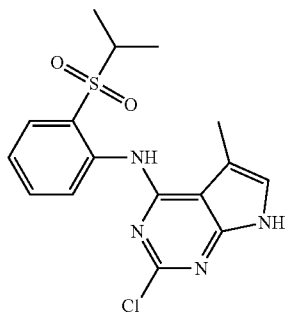 [SMILES: Cc1c[nH]c2nc(Cl)nc(Nc3ccccc3S(=O)(=O)C(C)C)c12]

86 mg mCPBA (0.38 mmol) was slowly added into a solution of 94 mg 2-chloro-N-(2-(isopropylthio)phenyl)-5-methyl-7-tosyl-7H-pyrrolo[2,3-d]pyrimidin-4-amine (9) (0.19 mmol) in 10 mL of $CHCl_3$ at room temperature. After stiffing for two hours at ambient temperature, the reaction was quenched by adding 5 mL of saturated aqueous $Na_2SO_3$ solution and the resulting two layers are separated. The aqueous layer is extracted with $CH_2Cl_2$ (3×10 mL) and the combined organic layers were washed with brine and concentrated. The residue was redissolved in 5 mL of MeOH and to this solution was added 1.1 mL of NaOMe (0.5M solution in MeOH, 0.55 mmol). The mixture was heated to 50° C. and stirred for 30 minutes. After cooling to room temperature, the solvent was removed under vacuum and the residue was redissolved in 20 mL of EtOAc, washed with saturated aqueous $NaHCO_3$ solution and brine, dried over $Na_2SO_4$ and concentrated to yield the title compound as white solid.

N2-(2-isopropoxy-5-methyl-4-(piperidin-4-yl)phenyl)-N4-(2-(isopropylsulfonyl)phenyl)-5-methyl-7H-pyrrolo[2,3-d]pyrimidine-2,4-diamine

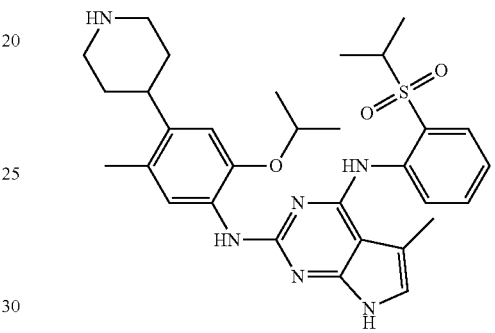

32 mg TsOH (0.165 mmol) was added into a solution of 20 mg N2-(2-isopropoxy-5-methyl 4-(piperidin-4-yl)phenyl)-N4-(2-(isopropylsulfonyl)phenyl)-5-methyl-7H-pyrrolo[2,3-d]pyrimidine-2,4-diamine (0.055 mmol) and 31.3 mg 2-isopropoxy-5-methyl-4-(piperidin-4-yl)aniline HCl salt (0.11 mmol) in 0.2 mL of 2-propanol. The reaction mixture was heated to 170° C. and stirred for 40 minutes under microwave irradiation. After cooling to room temperature, the solvent was removed under vacuum and the residue was redissolved in 1 mL of DMSO and purified by mass-triggered HPLC to give the title compound.

EXAMPLE 22

2-(4-(5-isopropoxy-4-(4-(2-(isopropylsulfonyl)phenylamino)-5-methyl-7H-pyrrolo[2,3-d]pyrimidin-2-ylamino)-2-methylphenyl)piperidin-1-yl)acetamide (69)

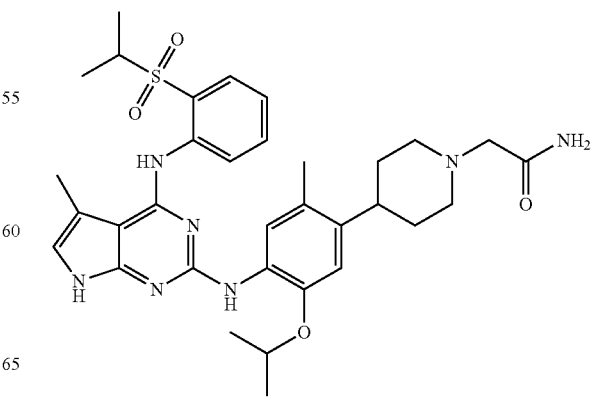

82 uL of Et3N (0.69 mmol) was added into a solution of 40 mg N$_2$-(2-isopropoxy-5-methyl-4-(piperidin-4-yl)phenyl)-N4-(2-(isopropylsulfonyl)phenyl)-5-methyl-7H-pyrrolo[2,3-d]pyrimidine-2,4-diamine (11) (0.069 mmol) and 28.5 mg 2-bromoacetamide (0.207 mmol) in 1 mL of DMF. The reaction mixture was heated to 100° C. and stirred for 10 minutes under microwave irradiation. After cooling to room temperature, the solvent was removed under vacuum and the residue was redissolved in 1 mL of DMSO and purified by mass-triggered HPLC to give the title compound.

Table 3 describes compounds which may be obtained by repeating the procedures described in examples above, using appropriate starting materials.

TABLE 3

| Structure | Physical Data $^1$H NMR 400 MHz (DMSO-d6) and/or MS (m/z) | ALK IC50 (μM) |
|---|---|---|
| 68<br><br>N2-(2-isopropoxy-5-methyl-4-(piperidin-4-yl)phenyl)-N4-(2-(isopropylsulfonyl)phenyl)-5-methyl-7H-pyrrolo[2,3-d]pyrimidine-2,4-diamine | HCl salt, (in MeOH-d4) δ 8.20 (d, J = 8.0 Hz, 1H), 7.84 (dd, J = 8.0, 1.6 Hz, 1H), 7.76 (s, 1H), 7.60-7.56 (m, 1H), 7.32-7.28 (m, 1H), 6.73 (s, 1H), 6.68 (d, J = 1.2 Hz, 1H), 4.55-4.45 (m, 1H), 3.43-3.40 (m, 2H), 3.25-3.20 (m, 1H), 3.11-3.01 (m, 2H), 2.99-2.95 (m, 1H), 2.40 (s, 3H), 2.03 (s, 3H), 1.90-1.73 (m, 4H), 1.23 (d, J = 6.0 Hz, 6H), 1.14 (d, J = 6.8 Hz, 6H). MS (ES$^+$): 577.3 (M + 1)$^+$. | 0.155 |
| 69<br><br>2-(4-(5-isopropoxy-4-(4-(2-(isopropylsulfonyl)phenylamino)-5-methyl-7H-pyrrolo[2,3-d]pyrimidin-2-ylamino)-2-methylphenyl)piperidin-1-yl)acetamide | HCl salt, δ 11.52 (s, 1H), 9.60 (s, 1H), 9.17 (s, 1H), 8.34 (d, J = 8.0 Hz, 1H), 8.06 (s, 1H), 7.88 (dd, J = 8.0, 1.6 Hz, 1H), 7.84 (s, 1H), 7.74 (s, 1H), 7.73-7.69 (m, 1H), 7.42-7.38 (m, 1H), 6.86 (s, 1H), 6.79 (s, 1H), 4.58-4.52 (m, 1H), 3.93 (s, 2H), 3.58-3.50 (m, 2H), 3.47-3.40 (m, 1H), 3.28-3.16 (m, 2H), 2.96-2.88 (m, 1H), 2.43 (s, 3H), 2.12-2.00 (m, 5H), 1.86-1.80 (m, 2H), 1.32 (d, J = 6.0 Hz, 6H), 1.15 (d, J = 6.8 Hz, 6H). MS (ES$^+$): 634.3 (M + 1)$^+$. | 0.007 |

TABLE 3-continued

| | Structure | Physical Data $^1$H NMR 400 MHz (DMSO-d6) and/or MS (m/z) | ALK IC50 (μM) |
|---|---|---|---|
| 70 | 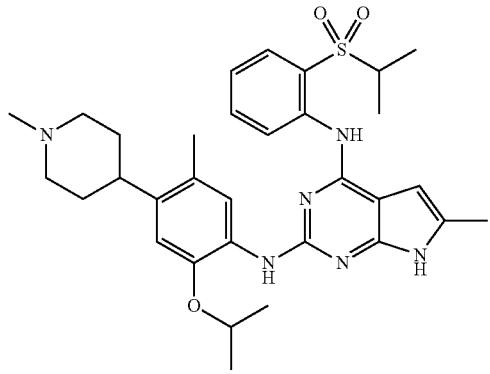

N2-(2-isopropoxy-5-methyl-4-(1-methylpiperidin-4-yl)phenyl)-N4-(2-(isopropylsulfonyl)phenyl)-6-methyl-7H-pyrrolo[2,3-d]pyrimidine-2,4-diamine | HCl salt, δ 11.41 (s, 1H), 9.43 (s, 1H), 9.31 (s, 1H), 8.55 (d, J = 8.0 Hz, 1H), 7.99 (s, 1H), 7.85 (dd, J = 8.0, 1.6 Hz, 1H), 7.74-7.70 (m, 1H), 7.53 (s, 1H), 7.36-7.32 (m, 1H), 6.72 (s, 1H), 5.99 (s, 1H), 4.55-4.52 (m, 1H), 3.53-3.50 (m, 2H), 3.46-3.42 (m, 1H), 3.15-3.08 (m, 2H), 2.96-2.88 (m, 1H), 2.82 (d, J = 4.8 Hz, 3H), 2.31 (s, 3H), 2.17 (s, 3H), 1.92-1.81 (m, 4H), 1.31 (d, J = 6.0 Hz, 6H), 1.16 (d, J = 6.8 Hz, 6H). MS (ES$^+$): 591.8 (M + 1)$^+$. | |
| 71 | 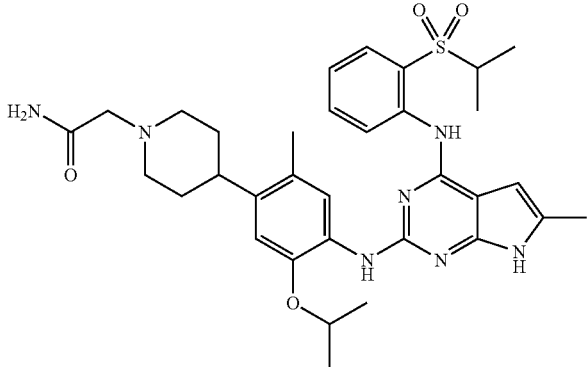 [SMILES: Cc1cc2c(Nc3ccccc3S(=O)(=O)C(C)C)nc(Nc3cc(C)c(C4CCN(CC(N)=O)CC4)cc3OC(C)C)nc2[nH]1]

2-(4-(5-isopropoxy-4-(4-(2-(isopropylsulfonyl)phenylamino)-6-methyl-7H-pyrrolo[2,3-d]pyrimidin-2-ylamino)-2-methylphenyl)piperidin-1-yl)acetamide | HCl salt, δ 11.35 (s, 1H), 9.41 (s, 1H), 9.37 (s, 1H), 8.60 (d, J = 8.0 Hz, 1H), 8.01 (s, 1H), 7.99 (s, 1H), 7.85 (dd, J = 8.0, 1.6 Hz, 1H), 7.76 (s, 1H), 7.73-7.69 (m, 1H), 7.44 (s, 1H), 7.33-7.30 (m, 1H), 6.77 (s, 1H), 5.98 (s, 1H), 4.58-4.51 (m, 1H), 3.93 (s, 2H), 3.53-3.50 (m, 2H), 3.46-3.42 (m, 1H), 3.27-3.16 (m, 2H), 2.97-2.91 (m, 1H), 2.32 (s, 3H), 2.18 (s, 3H), 2.10-1.99 (m, 2H), 1.87-1.84 (m, 2H), 1.33 (d, J = 6.0 Hz, 6H), 1.16 (d, J = 6.8 Hz, 6H). MS (ES$^+$): 634.3 (M + 1)$^+$. | |
| 72 | 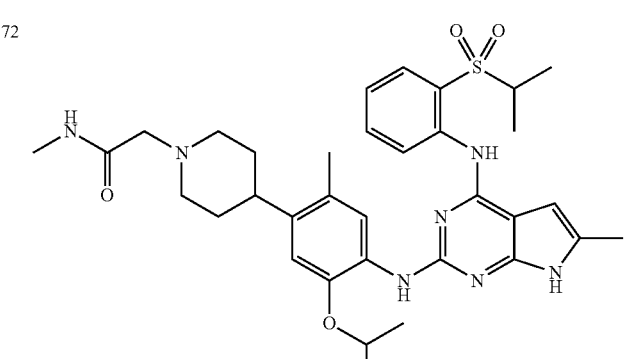

2-(4-(5-isopropoxy-4-(4-(2-(isopropylsulfonyl)phenylamino)-6-methyl-7H-pyrrolo[2,3-d]pyrimidin-2-ylamino)-2-methylphenyl)piperidin-1-yl)-N-methylacetamide | HCl salt, δ 11.36 (s, 1H), 9.54 (s, 1H), 9.37 (s, 1H), 8.59 (d, J = 8.0 Hz, 1H), 8.51-8.48 (m, 1H), 8.01 (s, 1H), 7.85 (dd, J = 8.0, 1.6 Hz, 1H), 7.73-7.69 (m, 1H), 7.44 (s, 1H), 7.34-7.29 (m, 1H), 6.77 (s, 1H), 5.98 (s, 1H), 4.58-4.51 (m, 1H), 3.93 (s, 2H), 3.53-3.50 (m, 2H), 3.46-3.42 (m, 1H), 3.27-3.16 (m, 2H), 2.97-2.91 (m, 1H), 2.70 (d, J = 4.8 Hz, 3H), 2.31 (s, 3H), 2.17 (s, 3H), 2.10-1.99 (m, 2H), 1.87-1.84 (m, 2H), 1.32 (d, J = 6.0 Hz, 6H), 1.16 (d, J = 6.8 Hz, 6H). MS (ES$^+$): 648.3 (M + 1)$^+$. | |

TABLE 3-continued

| | Structure | Physical Data ¹H NMR 400 MHz (DMSO-d6) and/or MS (m/z) | ALK IC50 (μM) |
|---|---|---|---|
| 73 | 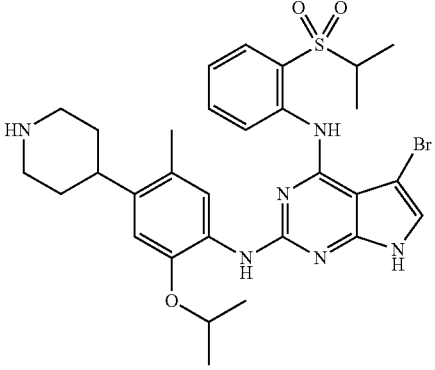 [SMILES: Cc1cc(Nc2nc(Nc3ccccc3S(=O)(=O)C(C)C)c3c(Br)c[nH]c3n2)c(OC(C)C)cc1C1CCNCC1]<br>5-bromo-N2-(2-isopropoxy-5-methyl-4-(piperidin-4-yl)phenyl)-N4-(2-(isopropylsulfonyl)phenyl)-7H-pyrrolo[2,3-d]pyrimidine-2,4-diamine | TFA salt, δ 12.11 (s, 1H), 9.31 (s, 1H), 8.49-8.46 (m, 1H), 8.33 (d, J = 8.0 Hz, 1H), 8.20-8.10 (m, 1H), 7.82-7.80 (m, 2H), 7.67-7.63 (m, 1H), 7.42 (s, 1H), 7.33-7.30 (m, 1H), 6.65 (s, 1H), 6.33 (s, 1H), 5.69 (s, 1H), 4.55-4.42 (m, 1H), 3.53-3.50 (m, 1H), 3.35-3.25 (m, 2H), 2.94-2.98 (m, 2H), 2.92-2.89 (m, 1H), 2.05 (s, 3H), 1.80-1.65 (m, 4H), 1.21 (d, J = 6.0 Hz, 6H), 1.06 (d, J = 6.8 Hz, 6H). MS (ES⁺): 641.1 (M + 1)⁺. | |
| 74 | 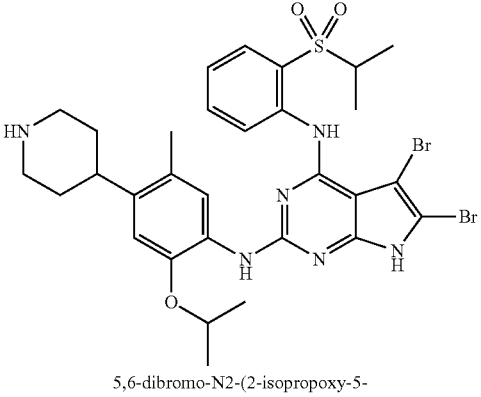<br>5,6-dibromo-N2-(2-isopropoxy-5-methyl-4-(piperidin-4-yl)phenyl)-N4-(2-(isopropylsulfonyl)phenyl)-7H-pyrrolo[2,3-d]pyrimidine-2,4-diamine | TFA salt, δ 12.55 (s, 1H), 9.10 (s, 1H), 8.49-8.46 (m, 1H), 8.18 (d, J = 8.0 Hz, 1H), 8.16-8.11 (m, 1H), 7.79 (dd, J = 8.0, 1.6 Hz, 1H), 7.75 (s, 1H), 7.63-7.59 (m, 1H), 7.48 (s, 1H), 7.33-7.29 (m, 1H), 6.64 (s, 1H), 4.45-4.42 (m, 1H), 3.70-3.65 (m, 1H), 3.35-3.25 (m, 2H), 3.00-2.90 (m, 2H), 2.90-2.84 (m, 1H), 2.01 (s, 3H), 1.76-1.67 (m, 4H), 1.20 (d, J = 6.0 Hz, 6H), 1.09 (d, J = 6.8 Hz, 6H). MS (ES⁺): 719.1 (M + 1)⁺. | |
| 75 | 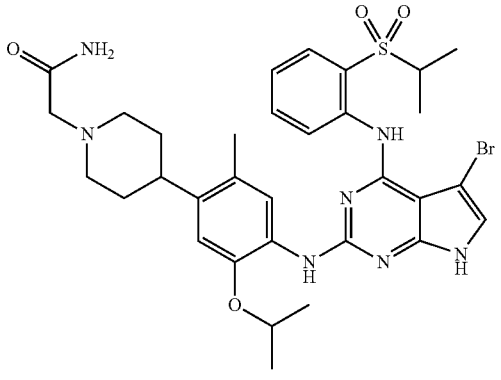 [SMILES: Cc1cc(Nc2nc(Nc3ccccc3S(=O)(=O)C(C)C)c3c(Br)c[nH]c3n2)c(OC(C)C)cc1C1CCN(CC(N)=O)CC1]<br>2-(4-(4-(5-bromo-4-(2-(isopropylsulfonyl)phenylamino)-7H-pyrrolo[2,3-d]pyrimidin-2-ylamino)-5-isopropoxy-2-methylphenyl)piperidin-1-yl)acetamide | TFA salt, δ 12.11 (s, 1H), 9.35 (s, 1H), 9.31 (s, 1H), 8.33 (d, J = 8.0 Hz, 1H), 7.92 (s, 1H), 7.82-7.80 (m, 2H), 7.68-7.63 (m, 2H), 7.43 (s, 1H), 7.33-7.30 (m, 1H), 6.69 (s, 1H), 6.33 (s, 1H), 4.47-4.44 (m, 1H), 3.85 (s, 2H), 3.53-3.50 (m, 2H), 3.39-3.34 (m, 1H), 3.16-3.09 (m, 2H), 2.88-2.82 (m, 1H), 2.05 (s, 3H), 1.99-1.92 (m, 2H), 1.78-1.75 (m, 2H), 1.23 (d, J = 6.0 Hz, 6H), 1.06 (d, J = 6.8 Hz, 6H). MS (ES⁺): 698.2 (M + 1)⁺. | |

TABLE 3-continued

| | Structure | Physical Data $^1$H NMR 400 MHz (DMSO-d6) and/or MS (m/z) | ALK IC50 (μM) |
|---|---|---|---|
| 76 | 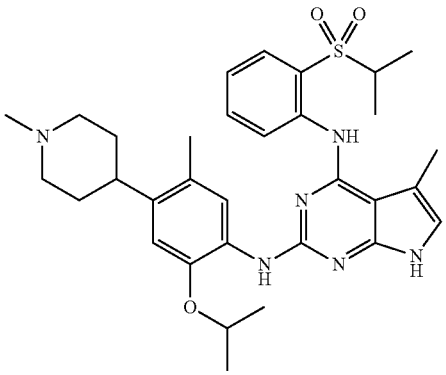 [SMILES: Cc1cc(Nc2nc(Nc3ccccc3S(=O)(=O)C(C)C)c3c(C)c[nH]c3n2)c(OC(C)C)cc1C1CCN(C)CC1]<br>N2-(2-isopropoxy-5-methyl-4-(1-methylpiperidin-4-yl)phenyl)-N4-(2-(isopropylsulfonyl)phenyl)-5-methyl-7H-pyrrolo[2,3-d]pyrimidine-2,4-diamine | HCl salt, δ 11.31 (s, 1H), 9.88 (s, 1H), 9.13 (s, 1H), 8.39 (d, J = 8.0 Hz, 1H), 7.92 (s, 1H), 7.85 (dd, J = 8.0, 1.2 Hz, 1H), 7.72-7.68 (m, 1H), 7.39-7.35 (m, 1H), 6.84 (s, 1H), 6.74 (s, 1H), 4.55-4.45 (m, 1H), 3.49-3.42 (m, 3H), 3.15-3.07 (m, 2H), 2.95-2.85 (m, 1H), 2.78 (d, J = 4.8 Hz, 3H), 2.42 (s, 3H), 2.07 (s, 3H), 1.95-1.85 (m, 4H), 1.29 (d, J = 6.0 Hz, 6H), 1.15 (d, J = 6.8 Hz, 6H) MS (ES$^+$): 591.3 (M + 1)$^+$. | 0.009 |
| 77 | 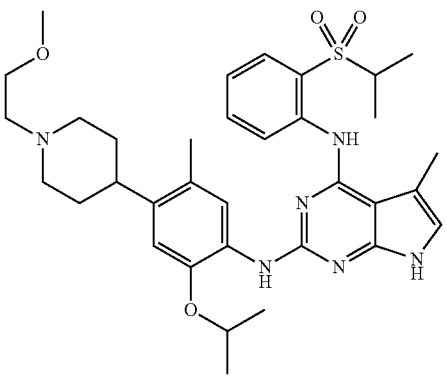 [SMILES: COCCN1CCC(c2cc(OC(C)C)c(Nc3nc(Nc4ccccc4S(=O)(=O)C(C)C)c4c(C)c[nH]c4n3)cc2C)CC1]<br>N2-(2-isopropoxy-4-(1-(2-methoxyethyl)piperidin-4-yl)-5-methylphenyl)-N4-(2-(isopropylsulfonyl)phenyl)-5-methyl-7H-pyrrolo[2,3-d]pyrimidine-2,4-diamine | HCl salt, δ 11.38 (s, 1H), 9.80 (s, 1H), 9.14 (s, 1H), 8.37 (d, J = 8.0 Hz, 1H), 7.89 (s, 1H), 7.86 (dd, J = 8.0, 1.2 Hz, 1H), 7.72-7.68 (m, 1H), 7.39-7.35 (m, 1H), 6.84 (s, 1H), 6.76 (s, 1H), 4.55-4.45 (m, 1H), 3.73-3.71 (m, 2H), 3.58-3.55 (m, 2H), 3.47-3.40 (m, 1H), 3.34 (s, 3H), 3.32-3.27 (m, 2H), 3.16-3.06 (m, 2H), 2.96-2.87 (m, 1H), 2.42 (s, 3H), 2.06 (s, 3H), 2.04-1.97 (m, 2H), 1.86-1.82 (m, 2H), 1.30 (d, J = 6.0 Hz, 6H), 1.15 (d, J = 6.8 Hz, 6H). MS (ES$^+$): 635.3 (M + 1)$^+$. | |
| 78 | 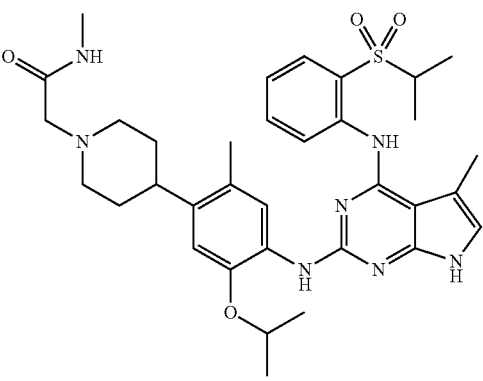 [SMILES: CNC(=O)CN1CCC(c2cc(OC(C)C)c(Nc3nc(Nc4ccccc4S(=O)(=O)C(C)C)c4c(C)c[nH]c4n3)cc2C)CC1]<br>2-(4-(5-isopropoxy-4-(4-(2-(isopropylsulfonyl)phenylamino)-5-methyl-7H-pyrrolo[2,3-d]pyrimidin-2-ylamino)-2-methylphenyl)piperidin-1-yl)-N-methylacetamide | HCl salt, δ 11.71 (s, 1H), 9.83 (s, 1H), 9.21 (s, 1H), 8.70-8.64 (m, 1H), 8.27 (d, J = 8.0 Hz, 1H), 7.88 (dd, J = 8.0, 1.6 Hz, 1H), 7.77 (s, 1H), 7.73-7.69 (m, 1H), 7.42-7.38 (m, 1H), 6.86 (s, 1H), 6.79 (s, 1H), 4.58-4.52 (m, 1H), 3.93 (s, 2H), 3.56-3.48 (m, 2H), 3.47-3.40 (m, 1H), 3.28-3.16 (m, 2H), 2.96-2.88 (m, 1H), 2.68 (d, J = 4.8 Hz, 3H), 2.42 (s, 3H), 2.12-2.00 (m, 5H), 1.86-1.80 (m, 2H), 1.30 (d, J = 6.0 Hz, 6H), 1.14 (d, J = 6.8 Hz, 6H). MS (ES$^+$): 648.3 (M + 1)$^+$. | |

TABLE 3-continued

| | Structure | Physical Data ¹H NMR 400 MHz (DMSO-d6) and/or MS (m/z) | ALK IC50 (μM) |
|---|---|---|---|
| 79 | 2-(4-(5-isopropoxy-4-(4-(2-(isopropylsulfonyl)phenylamino)-5-methyl-7H-pyrrolo[2,3-d]pyrimidin-2-ylamino)-2-methylphenyl)piperidin-1-yl)ethanol | HCl salt, δ 11.34 (s, 1H), 9.68 (s, 1H), 9.13 (s, 1H), 8.39 (d, J = 8.0 Hz, 1H), 7.91 (s, 1H), 7.86 (dd, J = 8.0, 1.6 Hz, 1H), 7.73-7.68 (m, 1H), 7.39-7.35 (m, 1H), 6.84 (s, 1H), 6.77 (s, 1H), 4.55-4.45 (m, 1H), 3.82-3.78 (m, 2H), 3.62-3.56 (m, 2H), 3.47-3.40 (m, 1H), 3.20-3.15 (m, 2H), 3.15-3.05 (m, 2H), 2.98-2.88 (m, 1H), 2.42 (s, 3H), 2.07 (s, 3H), 2.06-2.00 (m, 2H), 1.86-1.82 (m, 2H), 1.30 (d, J = 6.0 Hz, 6H), 1.15 (d, J = 6.8 Hz, 6H). MS (ES⁺): 621.3 (M + l)⁺. | 0.006 |
| 80 | (R)-1,1,1-trifluoro-3-(4-(5-isopropoxy-4-(4-(2-(isopropylsulfonyl)phenylamino)-5-methyl-7H-pyrrolo[2,3-d]pyrimidin-2-ylamino)-2-methylphenyl)piperidin-1-yl)propan-2-ol | MS (ES⁺): 675.8 (M + l)⁺. | 0.163 |
| 81 | (S)-1,1,1-trifluoro-3-(4-(5-isopropoxy-4-(4-(2-(isopropylsulfonyl)phenylamino)-5-methyl-7H-pyrrolo[2,3-d]pyrimidin-2-ylamino)-2-methylphenyl)piperidin-1-yl)propan-2-ol | MS (ES⁺): 675.8 (M + l)⁺. | 0.102 |

EXAMPLE 23

N5-(2-isopropoxy-5-methyl-4-(piperidin-4-yl)phenyl)-N7-(2-(isopropylsulfonyl)phenyl)-3H-[1,2,3]triazolo[4,5-d]pyrimidine-5,7-diamine (example 82)

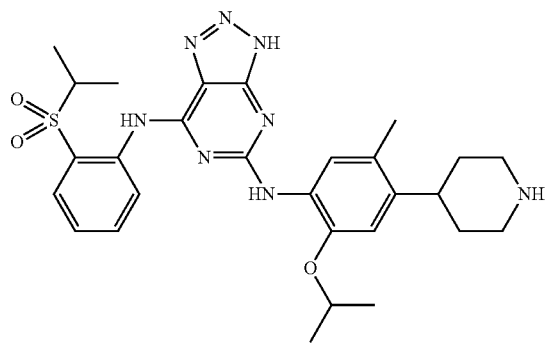 [SMILES: Cc1cc(Nc2nc(Nc3ccccc3S(=O)(=O)C(C)C)c3nn[nH]c3n2)c(OC(C)C)cc1C1CCNCC1]

5-amino-1-(4-methoxybenzyl)-1H-1,2,3-triazole-4-carboxamide

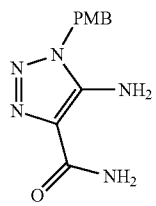

A mixture of 1-(azidomethyl)-4-methoxybenzene (5 g) and 2-cyanoacetamide (5 g) was added to a solution of sodium ethoxide (made from 1.6 g of sodium in 100 mL of ethanol). The resulting mixture was refluxed for 20 h. It was cooled down to room temperature and solvent was removed under reduced pressure. The remaining solid was dissolved in water (20 mL) and extracted with ethyl acetate (3×50 mL). The extracts were combined, washed with brine and dried over sodium sulfate. Solvent was removed and the residue was crystallized from hot water to give the desired product 5-amino-1-(4-methoxybenzyl)-1H-1,2,3-triazole-4-carboxamide. ESMS calculated for $C_{11}H_{13}N_5O_2$ (m/z): 247.1; found (M+H$^+$): 248.1

3-(4-methoxybenzyl)-3H-[1,2,3]triazolo[4,5-d]pyrimidine-5,7-diol

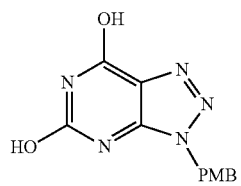

To a solution of 5-amino-1-(4-methoxybenzyl)-1H-1,2,3-triazole-4-carboxamide (0.9 g) and diethyl carbonate (1.2 mL) in THF (30 mL) was added potassium tert-butoxide (1.2 g). The mixture was refluxed under nitrogen for 6 h. It was then cooled down to room temperature. Water (20 mL) was added and the reaction mixture was concentrated to about 20 mL. It was neutralized with 1N HCl to pH 6 and filtered. Solid was collected and washed with water, and air dried to give desired product. $^1$H NMR (400 MHz, MeOD-d$_4$) δ 7.24 (d, 2H), 7.21 (m, 1H), 6.92 (d, 2H), 6.88 (m, 1H), 5.52 (s, 2H), 3.78 (s, 3H) ppm; ESMS calculated for $C_{12}H_{11}N_5O_3$ (m/z): 273.0, found (M+H$^+$): 274.0.

5,7-dichloro-3-(4-methoxybenzyl)-3H-[1,2,3]triazolo[4,5-d]pyrimidine

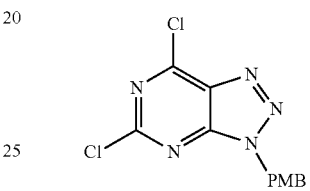

A mixture of 3-(4-methoxybenzyl)-3H-[1,2,3]triazolo[4,5-d]pyrimidine-5,7-diol (0.8 g), phosphorous oxychloride (3 mL) and collidine (2.1 mL) was heated at 120° C. for 3 h and cooled to room temperature. Ice-water was added and the mixture was extracted with ethyl acetate (3×15 mL). The organics were combined, washed with water and dried over magnesium sulfate. Solvent was removed under reduced pressure and crude 5,7-dichloro-3-(4-methoxybenzyl)-3H-[1,2,3]triazolo[4,5-d]pyrimidine was used directly in the next step without further purification.

5-chloro-N-(2-(isopropylthio)phenyl)-3-(4-methoxybenzyl)-3H-[1,2,3]triazolo[4,5-d]pyrimidin-7-amine

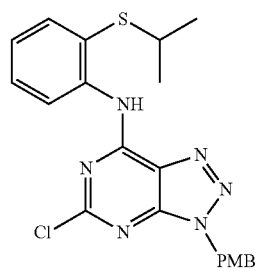

A solution of 5,7-dichloro-3-(4-methoxybenzyl)-3H-[1,2,3]triazolo[4,5-d]pyrimidine (0.03 g) and 2-(isopropylthio)aniline (0.1 g) in dioxane (10 mL) was heated at 100° C. for 10 h. It was then cooled down to room temperature and ethyl acetate (20 mL) was added. The mixture was washed with saturated sodium bicarbonate (10 mL), and dried over sodium sulfate. Solvent was removed under reduced pressure and the remaining residue was purified on a silica gel column (ethyl acetate:hexane=1:10) to give desired product. ESMS calculated for $C_{21}H_{21}ClN_6OS$ (m/z): 440.1; found (M+H$^+$): 441.1.

5-chloro-N-(2-(isopropylsulfonyl)phenyl)-3-(4-methoxybenzyl)-3H-[1,2,3]triazolo[4,5-d]pyrimidin-7-amine

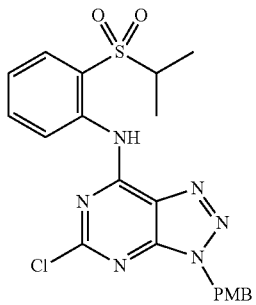

To a solution of 5-chloro-N-(2-(isopropylthio)phenyl)-3-(4-methoxybenzyl)-3H-[1,2,3]triazolo[4,5-d]pyrimidin-7-amine (0.1 g) in dichloromethane (25 mL) was added 3-chloroperoxybenzoic acid (77%, 230 mg). The mixture was stirred at room temperature for 4 h. Dichloromethane (20 mL) was added and the mixture was washed with saturated sodium bicarbonate (10 mL) and dried over sodium sulfate. Solvent was removed under reduced pressure and the remaining residue was purified on silica gel column (ethyl acetate:hexane=1:3) to afford the pure desired product. $^1$H NMR (400 MHz, acetone-d$_6$) δ 10.81 (s, 1H), 8.82 (d, 1H), 7.96 (d, 1H), 7.82 (dd, 1H), 7.48 (dd, 1H), 7.42 (d, 2H), 6.92 (d, 2H), 5.82 (s, 2H), 3.91 (s, 3H), 3.68 (m, 1H), 1.36 (d, 6H) ppm; ESMS calculated for $C_{21}H_{21}ClN_6O_3S$ (m/z): 472.1, found (M+H$^+$): 472.2.

N5-(2-isopropoxy-5-methyl-4-(piperidin-4-yl)phenyl)-N7-(2-(isopropylsulfonyl)phenyl)-3H-[1,2,3]triazolo[4,5-d]pyrimidine-5,7-diamine (Example 87)

A solution of 5-chloro-N-(2-(isopropylsulfonyl)phenyl)-3-(4-methoxybenzyl)-3H-[1,2,3]triazolo[4,5-d]pyrimidin-7-amine (10 mg) and 2-isopropoxy-5-methyl-4-(piperidin-4-yl)aniline (7 mg) in 2 M HCl/dioxane (2 mL) was sealed in a pressure tube and heated at 110° C. for 2 days. It was cooled to room temperature and solvent was removed under reduced pressure. The remaining residue was dissolved in trifluoroacetic acid (2 mL) and heated to 80° C. for 2 h. Trifluoroacetic acid was removed and the remaining product was purified by preparative LC-MS to afford desired product. $^1$H NMR (400 MHz, MeOD-d$_4$) δ 8.67 (d, 1H), 7.98 (m, 2H), 7.74 (t, 1H), 7.43 (t, 1H), 6.82 (s, 1H), 4.61 (m, 1H), 3.57 (m, 2H), 3.38 (m, 1H), 3.18-3.24 (m, 2), 2.26 (s, 3H), 2.03 (m, 2H), 1.82-1.93 (m, 2H), 1.41 (d, 6H), 1.31 (d, 6H) ppm; ESMS calculated for $C_{28}H_{36}N_8O_3S$ (m/z): 564.2 (M+H$^+$), found: 565.2.

EXAMPLE 24

N2-(2-isopropoxy-5-methyl-4-(1-methylpiperidin-4-yl)phenyl)-N6-(2-(isopropylsulfonyl)phenyl)-7-methyl-7H-purine-2,6-diamine (example 89)

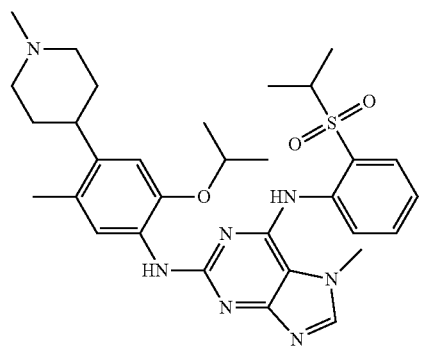 [SMILES: Cc1cc(Nc2nc(Nc3ccccc3S(=O)(=O)C(C)C)c3c(ncn3C)n2)c(OC(C)C)cc1C1CCN(C)CC1]

2-chloro-N-(2-(isopropylsulfonyl)phenyl)-7-methyl-7H-purin-6-amine

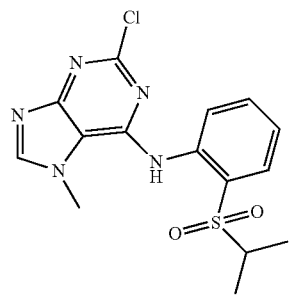 [SMILES: CC(C)S(=O)(=O)c1ccccc1Nc1nc(Cl)nc2ncn(C)c12]

A slurry of MCPBA (2.2 equivalents) is added into a solution of 2-chloro-N-(2-(isopropylthio)phenyl)-7-methyl-7H-purin-6-amine (1 equivalent) in CHCl$_3$ (2 mL/mmol) at room temperature. After stirring for two hours at ambient temperature, the reaction is quenched by adding 5 mL of saturated aqueous Na$_2$SO$_3$ solution and the resulting two layers were separated. The aqueous layer was extracted with CH$_2$Cl$_2$ and the combined organic layers were washed with brine and concentrated. The resulting residue was purified using flash column chromatography to afford the desired product as a white solid.

N2-(2-isopropoxy-5-methyl-4-(1-methylpiperidin-4-yl)phenyl)-N6-(2-(isopropylsulfonyl)phenyl)-7-methyl-7H-purine-2,6-diamine To a suspension of 2-chloro-N-(2-(isopropylsulfonyl)phenyl)-7-methyl-7H-purin-6-amine (1 equivalent) in isopropanol, was added 2-isopropoxy-5-methyl-4-(1-methylpiperidin-4-yl)aniline (1 equivalent) and 4-methylbenzenesulfonic acid (1 equivalent). The suspension was stirred at 150° C. for 3 hours, cooled to room temperature and the solvent evaporated. The residue was purified using a preparative HPLC to afford the desired product as a gummy solid.

Table 4 describes compounds which may be obtained by repeating the procedures described in examples above, using appropriate starting materials.

TABLE 4

| | Structure | Physical Data ¹H NMR 400 MHz (DMSO-d6) and/or MS (m/z) | ALK IC50 (µM) |
|---|---|---|---|
| 82 | N5-(2-isopropoxy-5-methyl-4-(piperidin-4-yl)phenyl)-N7-(2-(isopropylsulfonyl)phenyl)-3H-[1,2,3]triazolo[4,5-d]pyrimidine-5,7-diamine | MS (ES+): 564.7 (M + 1)+. | |
| 83 | N5-(2-isopropoxy-5-methyl-4-(1-methylpiperidin-4-yl)phenyl)-N7-(2-(isopropylsulfonyl)phenyl)-3H-[1,2,3]triazolo[4,5-d]pyrimidine-5,7-diamine | MS (ES+): 578.7 (M + 1)+. | 0.048 |
| 84 | N5-(4-(1-ethylpiperidin-4-yl)-2-isopropoxy-5-methylphenyl)-N7-(2-(isopropylsulfonyl)phenyl)-3H-[1,2,3]triazolo[4,5-d]pyrimidine-5,7-diamine | MS (ES+): 592.7 (M + 1)+. | 0.039 |
| 85 | N7-(2-(isopropylsulfonyl)phenyl)-N5-(2-methoxy-5-methyl-4-(piperidin-4-yl)phenyl)-3H-[1,2,3]triazolo[4,5-d]pyrimidine-5,7-diamine | MS (ES+): 536.6 (M + 1)+. | |

TABLE 4-continued

| | Structure | Physical Data ¹H NMR 400 MHz (DMSO-d6) and/or MS (m/z) | ALK IC50 (μM) |
|---|---|---|---|
| 86 | N5-(2-isopropoxy-5-methyl-4-(piperidin-4-yl)phenyl)-N7-(2-(isopropylsulfonyl)phenyl)-2H-[1,2,3]triazolo[4,5-d]pyrimidine-5,7-diamine | MS (ES$^+$): 564.7 (M + 1)$^+$. | |
| 87 | N5-(4-(1-ethylpiperidin-4-yl)-2-isopropoxy-5-methylphenyl)-N7-(2-(isopropylsulfonyl)phenyl)-2H-[1,2,3]triazolo[4,5-d]pyrimidine-5,7-diamine | MS (ES$^+$): 592.7 (M + 1)$^+$. | |
| 88 | N7-(2-(isopropylsulfonyl)phenyl)-N5-(2-methoxy-5-methyl-4-(piperidin-4-yl)phenyl)-2H-[1,2,3]triazolo[4,5-d]pyrimidine-5,7-diamine | MS (ES$^+$): 536.6 (M + 1)$^+$. | |
| 89 | N2-(2-isopropoxy-5-methyl-4-(1-methylpiperidin-4-yl)phenyl)-N6-(2-(isopropylsulfonyl))phenyl)-7-methyl-7H-purine-2,6-diamine | MS (ES+): 591.7 (M + 1)+. | |

Assays

Compounds of the present invention may be assessed for their ability to inhibit ALK using assays described below, as well as other assays known in the art.

Ba/F3 Cell Line Panel and Reagents

Ba/F3 is a murine IL-3-dependent pro-B lymphoma cell line. Parental Ba/F3 cells are used to generate a panel of sublines whose proliferation and survival is rendered IL-3-independent by stable transduction with individual tyrosine kinases activated by fusion with the amino-terminal portion of TEL (amino acid 1-375) or BCR. In order to generate Ba/F3 cell lines transformed by Tel-Tyrosine Kinase (TK) fusions, parental Ba/F3 cells are infected with a retrovirus harboring each kinase domain and subjected to puromycin selection and IL-3 withdrawal to obtain IL-3-independent, transformed Ba/F3 cells.

Each transformed Ba/F3 cells are cultured in RPMI-1640 media (Gibco Cat #11875093, Carlsbad, Calif.) supplemented with 10% FBS (Hyclone Cat #SV30014.03, Logan, Utah), 4.5 g/L glucose (Sigma #G5400, St. Louis, Mo.), 1.5 g/L sodium bicarbonate (Biowhittaker #17-613E, Walkersville, Md.) and Pen/Strep (Gibco #10378-016, Carlsbad, Calif.). Cells are splitted twice weekly.

Ba/F3 Cell Viability Inhibition Assay

The potency of test compounds against various Tel-TK transformed Ba/F3 lines is determined as follows. Exponentially growing BaF3 Tel-TK cells are diluted in fresh medium to 75,000 cells/mL and seeded into 384-well plates (3750 cells/well) at 50 μL/well using a μFill liquid dispenser (BioTek, Winooski, Vt., USA). Duplicate plates are run for each cell line. Test and control compounds are serially diluted with DMSO and arrayed in a polypropylene 384-well plate. 50 nL of compound is transferred into the assay plates using a pin-transfer device, and the plates are incubated at 37° C. (5% CO2) for 48 hours. 25 μL Bright-Glo (Promega, Madison, Wis., USA) is added and luminescence is quantified using Analyst GT (Perkin Elmer, Wellesley, Mass.). Custom curve-fitting software is used to produce a logistic fit of percent cell viability as a function of the logarithm of inhibitor concentration. The $IC_{50}$ is interpolated as the concentration of compound needed to reduce cell viability to 50% of a DMSO control. Parental Ba/F3 cells that are maintained and cultured in presence of IL-3 (1 ng/ml in final) are diluted in fresh medium containing IL-3 (1 ng/ml in final) to 75,000 cells/mL following the same procedure as described above.

Kapas 299 Cellular Assay

Luciferized Karpas 299 (Karpas299-Luc) is generated by infecting retrovirus encoding luciferase gene, and cultured in RPMI-1649 medium supplemented with 10% FBS, 1% P/S/L-Glu. At day 1, cells are harvested and resuspended at density of 150,000 cells/ml (cell number is measured using ViCell (BD). Cells are dispensed from a diluted suspension into a 384-well assay plate in 50 μl volume using μFill (Bio-TEK). Serially diluted compounds (in DMSO) are transferred into plate using 50 nL pinhead. Assay plates are incubated at 37° C. for 48 hours. At day 4, 25 μl/well of Bright-Glo reagent (Promega) is added using μFill (Bio-TEK). Within 30 minutes, a luciferase signal is measured using Analyst GT in default setting for luminescence detection.

Enzymatic HTRF Assay

IGF-1R and INSR (insulin receptor) are purchased from Upstate. Following reagents are prepared in-house; 10× kinas buffer (KB) (200 mM Tris (pH 7.0), 100 mM $MgCl_2$, 30 mM $MnCl_2$, 50 nM $NaVO_4$), 10 mM ATP, 100 mg/ml BSA, 0.5 M EDTA, 4 M KF. Proxiplate-384 from Perkin-Elmer is used for set up assay. All the HTRF reagents including substrate (Biotin-poly-GT (61GT0BLB), Mab PT66-K, (61T66KLB), Streptavidin-XL$^{ent}$ (611SAXLB)) are purchased from CIS-US, Inc.

The substrate/ATP mix is prepared by adding ATP (final concentration, 3 μM) and biotinylated poly-GT (final concentration, 10 ng/μl) into 1× KB, and dispensed into Proxiplate-384 at 5 μl/well using μFill (Bio-TEK). Serially diluted compounds (in DMSO) are transferred into plate using 50 nL pinhead. 5 μL of prepared Enzyme mix (enzyme (final concentration, 5 ng/μl), mixed with BSA and DTT in 1× KB) is added to initiate kinase reaction using μFill (Bio-TEK). Assay plate is incubated at room temperature for 2 hours. Detection mix is prepared by adding both Mab PT66-K and Streptavidin-XL$^{ent}$ into 0.5× KB solution containing KF (final concentration, 125 mM), EDTA (final concentration, 50 mM) and BSA (final concentration, 100 μg/ml) in. At the end of reaction, 10 μL of detection mix is added and incubated for 30 minutes at room temperature before measurement. HTRF signal is detected using Analyst-GT (molecular dynamic).

Reporter Assay in U2OS Cells Using RE1-pGL3 for IGF1-S3-5 or INSR-S3-5

Seed 10M cells/T175 Flask in Mc Coy 10% FBS and 4 days later, suck off media and add fresh media. Next day (5 days after seeding), trypsinize cells, wash once with PBS, then resuspend cells in Mc-Coy media 4% delipidated serum with P/S/G. Count cells and dilute to 400,000 cells/ml.

For 95 ml of cells (400000 cells/ml (40M)), prepare the following DNA/Fugene6 mix: 5 ml Mc-Coy media without serum; 120 μg DNA mix (20 μg IGF1R-S3-5 or INSR-S3-5+ 100 μg RE1-pGL3); and 240 μL Fugene6 reagent. Incubate DNA/Fugene6 mix for 15 min before adding it to cells in 4% delipidated serum. Dispense 50 μL/well in 384 well plate. 22-24 h later, add 50 nL of serially diluted compounds using pinhead. 30 min later, add 2 μL of 26× IGF1 (or 100× Insulin) dose diluted in Mc-Coy 4% delipidated serum using μ-Fill. 30 hours later, add 25 μL 100% bright-glo and read on Analyst-GT for measuring luminescence.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

The invention claimed is:

1. A compound of Formula (1):

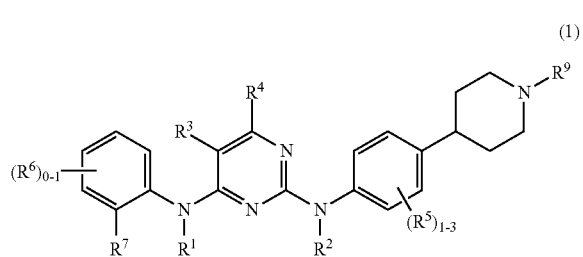

or a physiologically acceptable salt thereof;

$R^1$ and $R^2$ are independently H, $C_{1-6}$ alkyl or halo-substituted $C_{1-6}$ alkyl;

$R^3$ is halo, $C_{1-6}$ alkyl, or a halo-substituted $C_{1-6}$ alkyl;

$R^4$ is H;

alternatively, $R^3$ and $R^4$ together with the carbon atoms to which they are attached may form a 5-6 membered ring containing 1-3 heteroatoms selected from N, O and S, and optionally substituted with 1-2 $R^{10}$ groups wherein $R^{10}$ is halo, $C_{1-6}$ alkyl, $C_{2-6}$ alkenyl, $C_{2-6}$ alkynyl, optionally substituted phenyl or $NR_2$;

$R^5$ and $R^6$ are independently $C_{1-6}$ alkyl, $C_{1-6}$ alkoxy, $C_{2-6}$ alkenyl or $C_{2-6}$ alkynyl, each of which may be optionally substituted with halo, amino or hydroxyl groups; halo, nitro, cyano, $CR(OR^{17})R^{17}$, $OR^{17}$, $NR(R^{17})$, $CR(R^{17})NRR^{17}$, $(CR_2)_qY$, $C(O)O_{0-1}R^{17}$, $C(O)NR(R^{17})$, $C(O)CRR^{17}—NR(R^{17})$, $C(O)NR(CR_2)_pNR(R^{17})$, $C(O)NR(CR_2)_pOR^{17}$, $C(O)NR(CR_2)_pSR^{17}$, $C(O)NR(CR_2)_pS(O)_{1-2}R^{18}$, $S(O)_{0-2}R^{18}$, $(CR_2)_{1-6}NR(CR_2)_pOR^{17}$, $(CR_2)_{1-6}NR(CR_2)_qC(O)R^{18}$, $S(O)_2NRR^{17}$, $S(O)_2NR(CR_2)_pNR(R^{17})$, or $S(O)_2NR(CR_2)_pOR^{17}$;

$R^7$ is $S(O)_{0-2}R^{19}$, $S(O)_2NRR^{20}$ or $C(O)NR(R^{20})$; wherein $R^{19}$ and $R^{20}$ are independently $C_{1-6}$ alkyl, halo-substituted $C_{1-6}$ alkyl or $C_{3-7}$ cycloalkyl; or $R^{20}$ is H;

each $R^9$ is independently $-L-CR(OR^{17})—C_tF_{(2t+1)}$ wherein t is 1-3; $-L-C(O)—CR(R^{17})—NRR^{17}$, $-L-C(O)—NR—(CR_2)_p—NRR^{17}$, $-L-C(O)NR(CR_2)_pOR^{17}$, $-L-C(O)—(CR_2)_q—NR—C(O)—R^{18}$, $-L-C(O)NR(CR_2)_pSR^{17}$, $-L-C(O)NR(CR_2)_pS(O)_{1-2}R^{18}$, $(CR_2)_pNR(CR_2)_pOR^{17}$ or $(CR_2)_pNR-L-C(O)R^{18}$, $-L-S(O)_2R^{18}$, $-L-S(O)_2NRR^{17}$, $-L-S(O)_2NR(CR_2)_pNR(R^{17})$, or $-L-S(O)_2NR(CR_2)_pOR^{17}$; or $R^9$ is selected from formula (a), (b), (c) or (d):

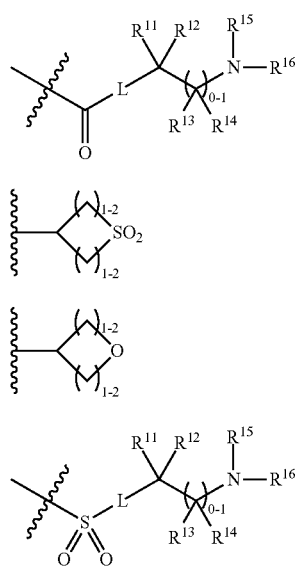

(a)

(b)

(c)

(d)

wherein $R^{11}, R^{12}, R^{13}, R^{14}, R^{15}$ and $R^{16}$ are independently selected from H, or $C_{1-6}$ alkyl, $C_{1-6}$ alkoxy, $C_{2-6}$ alkenyl or $C_{2-6}$ alkynyl, each of which may be optionally substituted with halo, amino or hydroxyl groups; or $R^{11}$ and $R^{12}$, $R^{12}$ and $R^{15}$, $R^{15}$ and $R^{16}$, $R^{13}$ and $R^{14}$, or $R^{13}$ and $R^{15}$ together with the carbon and/or nitrogen atoms to which they are attached may form a 3-7 membered saturated, unsaturated or partially unsaturated ring optionally containing up to 3 atoms or groups selected from $C(O)$, N, O and $S(O)_{0-2}$;

L is $(CR_2)_{1-4}$ or a bond;

$R^{17}$ and $R^{18}$ are independently $C_{1-6}$ alkyl, halo-substituted $C_{1-6}$ alkyl, $C_{2-6}$ alkenyl or $C_{2-6}$ alkynyl; or $R^{17}$ is H;

Y is a $C_{3-12}$ carbocyclic ring, $C_{6-10}$ aryl; or a 5-10 membered heteroaryl or 4-10 membered heterocyclic ring; each of which is optionally substituted with 1-3 $R^6$ groups;

each R is H or $C_{1-6}$ alkyl;

p is 2-4; and q is 0-4.

2. The compound of claim 1, wherein said compound is of Formula (3):

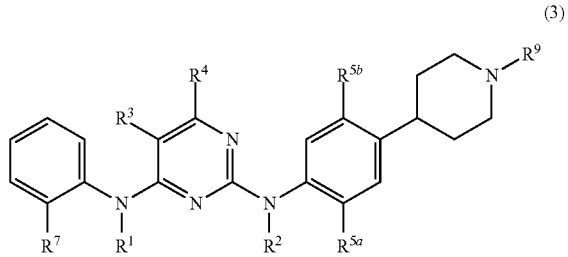

(3)

wherein $R^3$ is halo;

alternatively, $R^3$ and $R^4$ together with the carbon atoms to which they are attached may form a 5-6 membered ring containing 1-3 N heteroatoms, and optionally substituted with 1-2 $R^{10}$ groups;

$R^{5a}$ and $R^{5b}$ are independently halo, hydroxyl, $C_{1-6}$ alkyl, $C_{1-6}$ alkoxy, halo-substituted $C_{1-6}$ alkyl or halo-substituted $C_{1-6}$ alkoxy;

$R^7$ is $S(O)_{0-2}R^{19}$;

$R^1, R^2, R^9, R^{10}$ and $R^{19}$ are as defined in claim 1.

3. The compound of claim 2, wherein $R^{5a}$ is methoxy or isopropoxy;

$R^{5b}$ is or methyl;

$R^9$ is $-L-CR(OR^{17})—C_tF_{(2t+1)}$ wherein t is 1-3; $-L-S(O)_2R^{18}$, $-L-S(O)_2NRR^{17}$, $-L-S(O)_2NR(CR_2)_pNR(R^{17})$, or $-L-S(O)_2NR(CR_2)_pOR^{17}$; or $R^9$ is selected from formula (a), (b), (c) or (d):

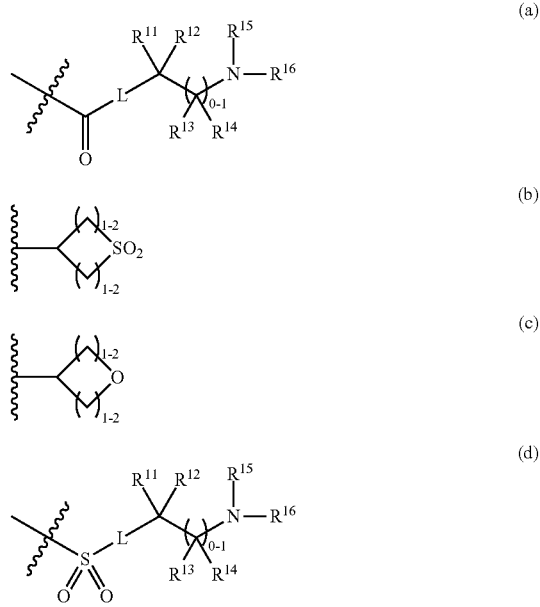

(a)

(b)

(c)

(d)

wherein $R^{11}, R^{12}, R^{13}, R^{14}, R^{15}, R^{16}, R^{17}, R^{18}$, L and p are as defined in claim 1.

4. The compound of claim 1, wherein said compound is of Formula (3A), (3B), (3C) or (3D):

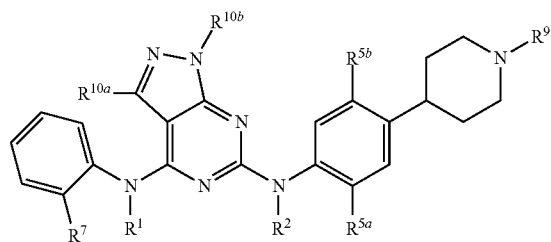
(3A)

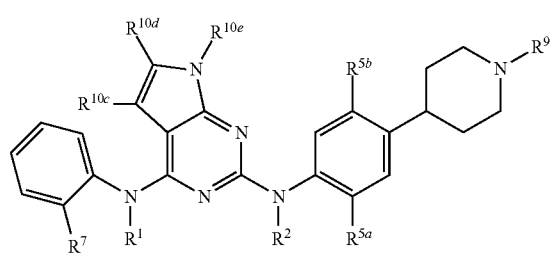
(3B)

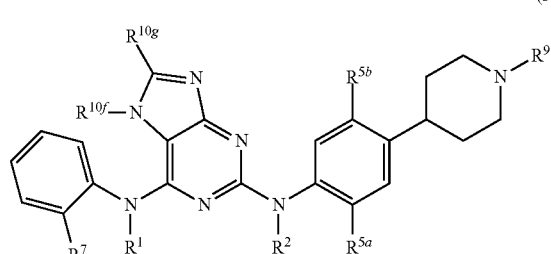
(3C)

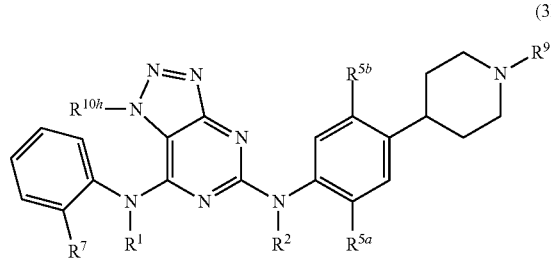
(3D)

wherein $R^{5a}$ is methoxy or isopropoxy;
$R^{5b}$ is methyl;
$R^{10b}$, $R^{10e}$, $R^{10f}$ and $R^{10h}$ are independently H or $C_{1-6}$ alkyl;
$R^{10a}$, $R^{10c}$, $R^{10d}$ and $R^{10g}$ are independently H, halo, $C_{1-6}$ alkyl, $NR_2$, or an optionally substituted phenyl; wherein one of $R^{10d}$, $R^{10c}$ or $R^{10e}$ in formula (3B) is a H; and
$R^1$, $R^2$, $R^7$, $R^9$ and R are as defined in claim 1.

5. The compound of claim 4, wherein $R^9$ is -L-CR(OR$^{17}$)-$C_tF_{(2t+1)}$ wherein t is 1-3; -L-S(O)$_2$R$^{18}$,-L-S(O)$_2$NRR$^{17}$,-L-S(O)$_2$NR(CR$_2$)$_p$NR(R$^{17}$), or -L -S(O)$_2$NR(CR$_2$)$_p$OR$^{17}$; or $R^9$ is selected from formula (a),(b),(c)or (d):

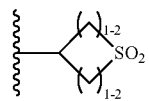
(a)

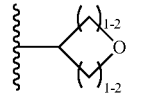
(b)

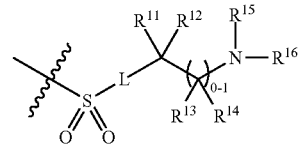
(c)

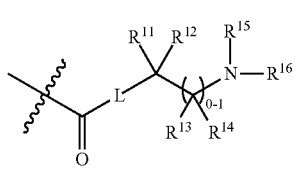
(d)

wherein $R^{11}$, $R^{12}$, $R^{13}$, $R^{14}$, $R^{15}$, $R^{16}$, L and p are as defined in claim 1; and
$R^{17}$ and $R^{18}$ are independently $C_{1-6}$ alkyl or halo-substituted $C_{1-6}$ alkyl; or $R^{17}$ is H.

6. The compound of claim 1, wherein $R^1$ and $R^2$ are H.

7. The compound of claim 1, wherein said compound is selected from the group consisting of:

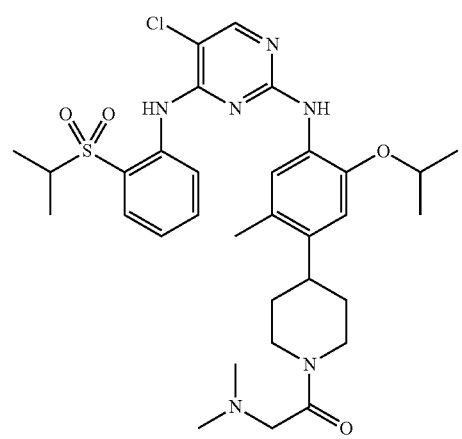

1-(4-(4-(5-chloro-4-(2-(isopropylsulfonyl)phenylamino)pyrimidin-2-ylamino)-5-isopropoxy-2-methylphenyl)piperidin-1-yl)-2-(dimethylamino)ethanone

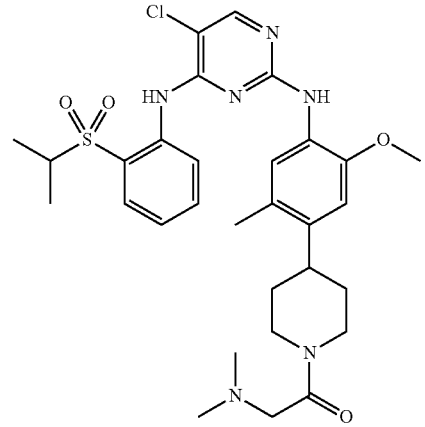

1-(4-(4-(5-chloro-4-(2-(isopropylsulfonyl)phenylamino)pyrimidin-2-ylamino)-5-methoxy-2-methylphenyl)piperidin-1-yl)-2-(dimethylamino)ethanone

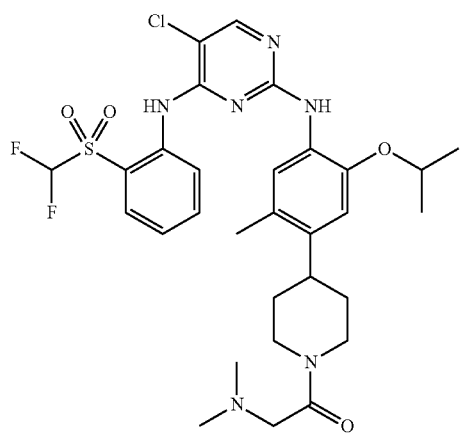

1-(4-(4-(5-chloro-4-(2-(difluoromethylsulfonyl)
phenylamino)pyrimidin-2-ylamino)-5-isopropoxy-2-
methylphenyl)piperidin-1-yl)-2-(dimethylamino)ethanone

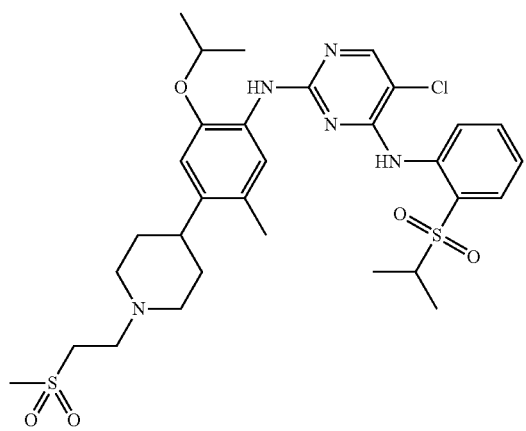

5-chloro-N2-(2-isopropoxy-5-methyl-4-(1-2-
(methylsulfonyl)ethyl)piperidin-4-yl)phenyl)-
N4-(2-(isoproplysulonyl)phenyl)pyrimidine-2,4-diamine

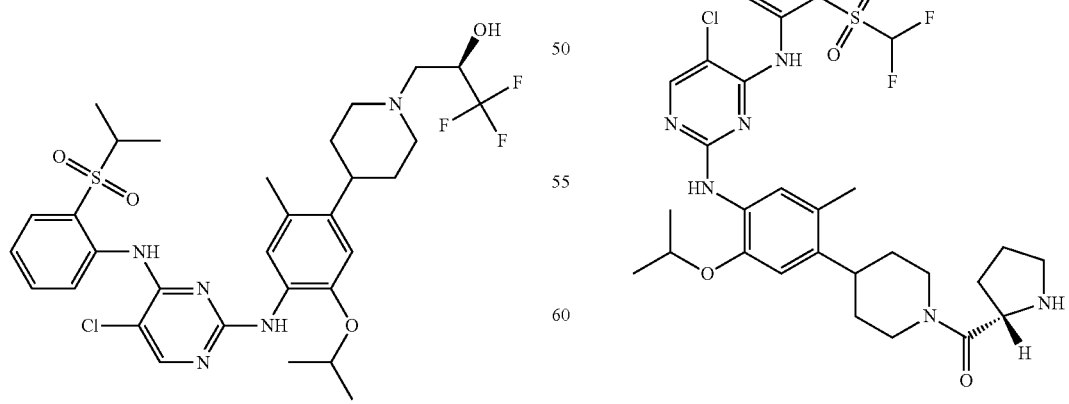

(R)-3-(4-(4-(5-chloro-4-(2-(isopropylsulfonyl)phenylamino)
pyrimidin-2-ylamino)-5-isopropoxy-2-methylphenyl)
piperidin-1-yl)-1,1,1-trifluoropropan-2-ol

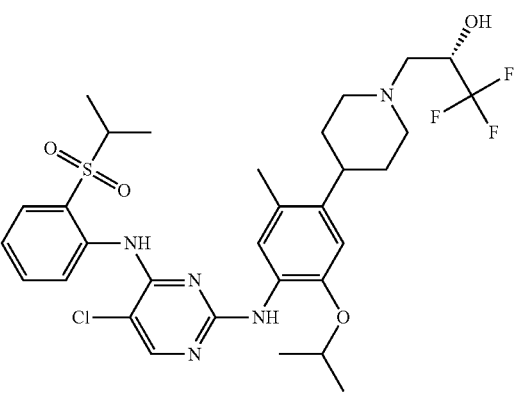

(S)-3-(4-(4-(5-chloro-4-(2-(isopropylsulfonyl)
phenylamino)pyrimidin-2-ylamino)-5-isopropoxy-
2-methylphenyl)piperidin-1-yl)-1,1,1-trifluoropropan-2-ol

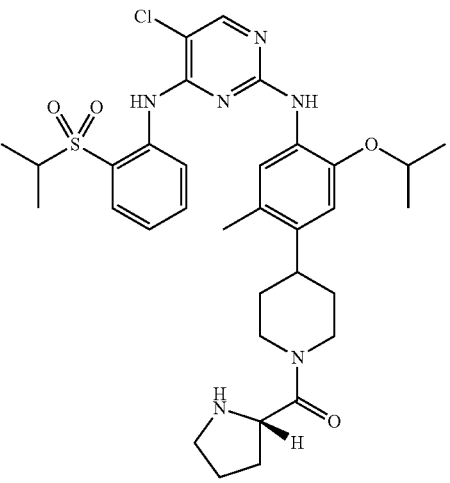

(S)-(4-(4-(5-chloro-4-(2-(isopropylsulfonyl)
phenylamino)pyrimidin-2-ylamino)-5-
isopropoxy-2-methylphenyl)piperidin-1-yl)
(pyrrolidin-2-yl)methanone (S)-(4-(4-(5-chloro-4-(2-(difluoromethylsulfonyl)
phenylamino)pyrimidin-2-ylamino)-5-isopropoxy-2-
methylphenyl)piperidin-1-yl)(pyrrolidin-2-yl)methanone

21

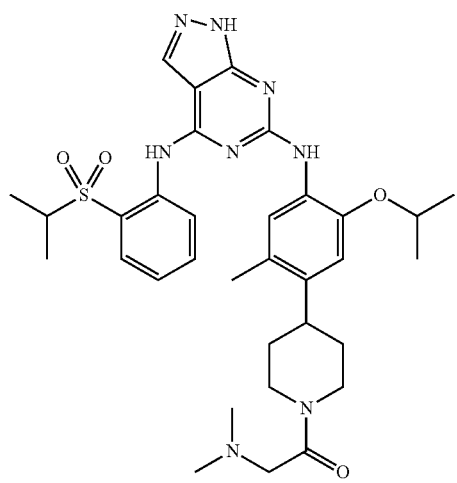

2-(dimethylamino)-1-(4-(5-isopropoxy-4-(4-(2-(isopropylsulfonyl)phenylamino)-1H-pyrazolo[3,4-d]pyrimidin-6-ylamino)-2-methylphenyl)piperidin-1-yl)ethanone

22

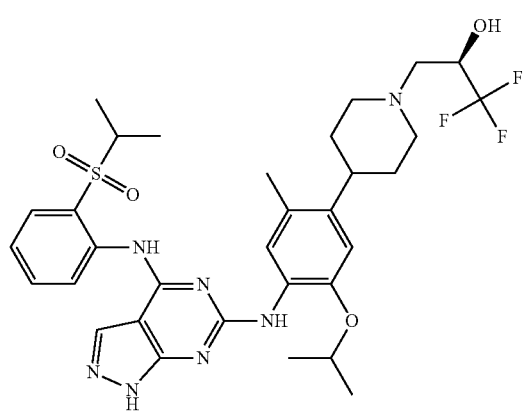

1,1,1-trifluoro-3-(4-(5-isopropoxy-4-(4-(2-(isopropylsulfonyl)phenylamino)-1H-pyrazolo[3,4-d]pyrimidin-6-ylamino)-2-methylphenyl)piperidin-1-yl)propan-2-ol

23

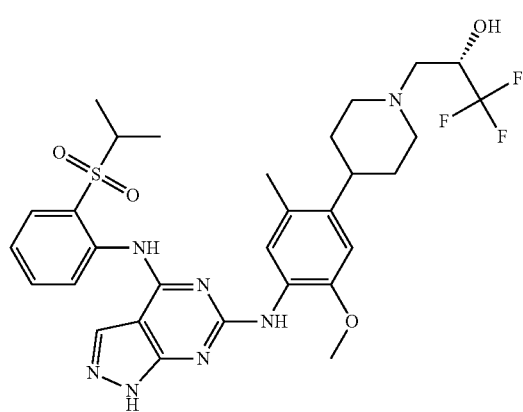

1,1,1-trifluoro-3-(4-(4-(4-(2-(isopropylsulfonyl)phenylamino)-1H-pyrazolo[3,4-d]pyrimidin-6-ylamino)-5-methoxy-2-methylphenyl)piperidin-1-yl)propan-2-ol

25

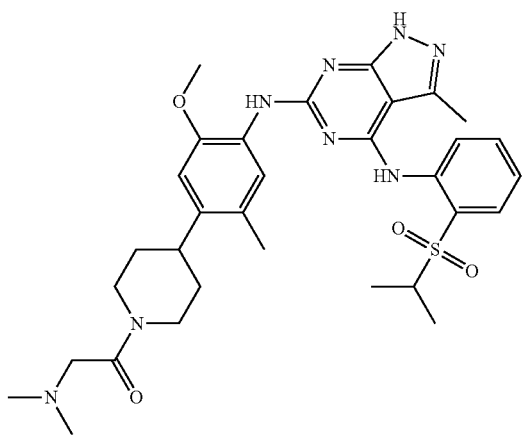

2-(dimethylamino)-1-(4-(4-(4-(2-(isopropylsulfonyl)phenylamino)-3-methyl-1H-pyrazolo[3,4-d]pyrimidin-6-ylamino)-5-methoxy-2-methylphenyl)piperidin-1-yl)ethanone

26

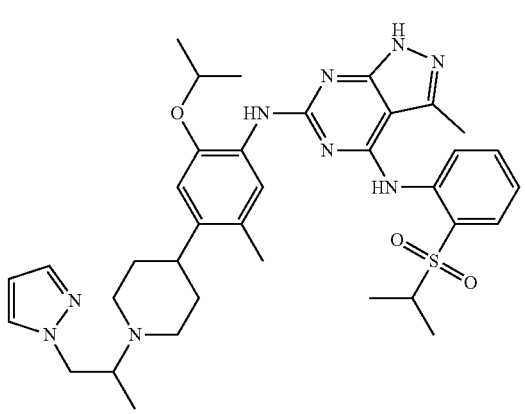

2-(dimethylamino)-1-(4-(5-isopropoxy-4-(4-(2-(isoproplsulfonyl)phenylamino)-3-methyl-1H-pyrazolo[3,4-d]pyrimidin-6-ylamino)-2-methylphenyl)piperidin-1-yl)ethanone

27

1-(4-(5-isopropoxy-4-(4-(2-(isopropylsulfonyl)phenylamio)-3-methyl-1H-pyrazolo[3,4-d]pyrimidin-6-ylamino)-2-methylphenyl)piperidin-1-yl)-2-(1H-pyrazol-1-yl)ethanone

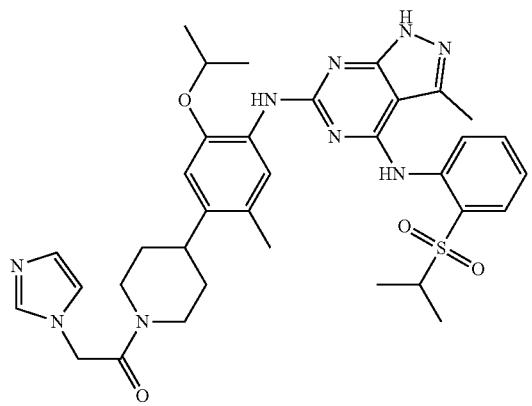

2-(1H-imidazol-1-yl)-1-(4-(5-isopropoxy-4-(4-(2-(isopropylsulfonyl)phenylamino)-3-methyl-1H-pyrazolo[3,4-d]pyrimidin-6-ylamino)-2-methylphenyl)piperidin-1-yl)ethanone

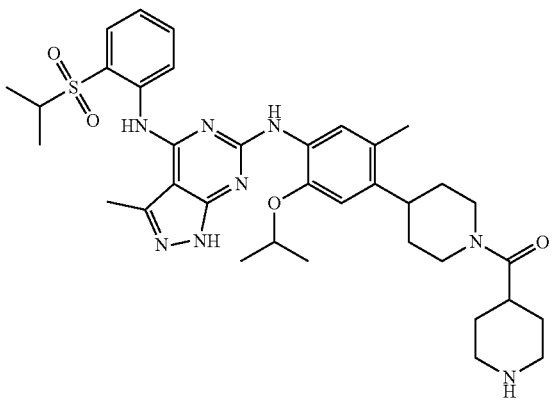

(4-(5-isopropoxy-4-(4-(2-(isopropylsulfonyl) phenylamino)-3-methyl-1H-pyrazolo[3,4-d]pyrimidin-6-ylamino)-2-methylphenyl) piperidin-1-yl)(piperidin-4-yl)methanone

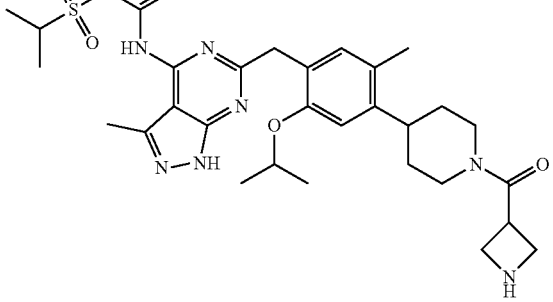

1-(4-(5-isopropoxy-4-(4-(2-(isopropylsulfony) phenylamino)-3-methyl-1H-pyrazolo[3,4-d]pyrimidin-6-ylamino)-2-methylphenyl) piperidin-1-yl)-2-(piperidin-1-yl)ethanone azetidin-3-yl(4-(5-isopropoxy-4-(4-(2-(isopropylsulfonyl) phenylamino)-3-methyl-1H-pyrazolo[3,4-d]pyrimidin-6-ylamino)-2-methylphenyl)piperidin-1-yl)methanone

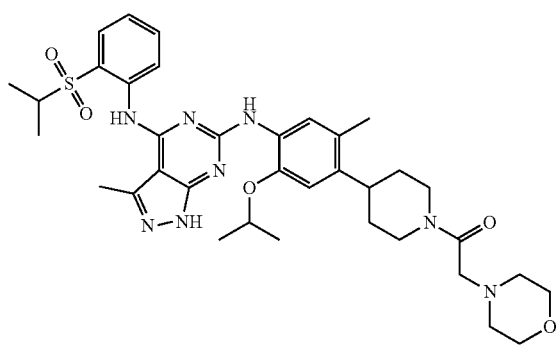

1-(4-(5-isopropoxy-4-(4-(2-(isopropylsulfonyl) phenylamino)-3-methyl-1H-pyrazolo[3,4-d]pyraimidin-6-ylamino)-2-methylphenyl) piperidin-1-yl)-2-morpholinoethanone

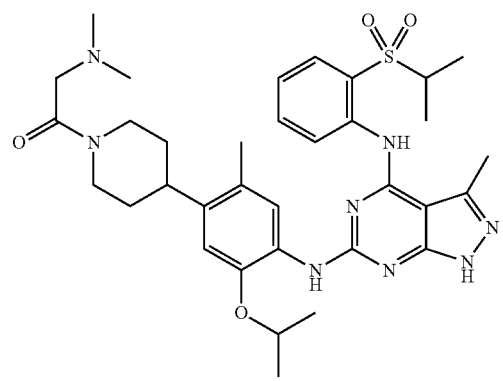

2-(dimethylamino)-1-(4-(5-isopropoxy-4-(4-(2-(isopropylsulfonyl) phenylamino)-3-methyl-1H-pyrazolo[3,4-d]pyrimidin-6-ylamino)-2-methylphenyl)piperidin-1-yl)ethanone

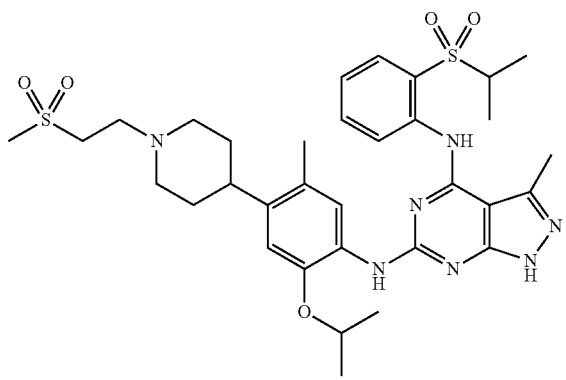

N6-(2-isopropoxy-5-methyl-4-(1-(2-(methylsulfonyl)ethyl)
piperidin-4-yl)phenyl)-N4-(2-(isopropylsulfonyl)phenyl)-3-
methyl-1H-pyrazolo[3,4-d]pyrimidine-4,6-diamine

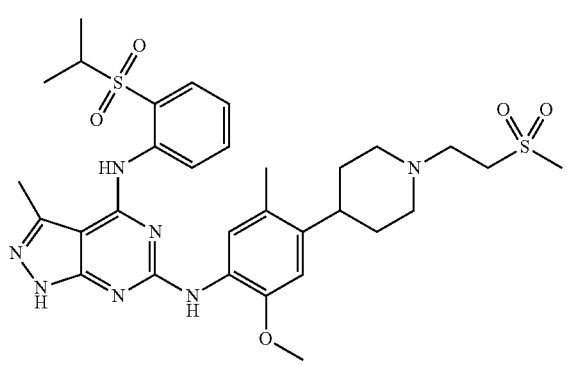

N4-(2-(isopropylsulfonyl)phenyl)-N6-(2-methoxy-5-methyl-4-(1-
(2-(methylsulfonyl)ethyl)piperidin-4-yl)phenyl)-3-methyl-1H-
pyrazolo[3,4-d]pyraimidine-4,6-diamine

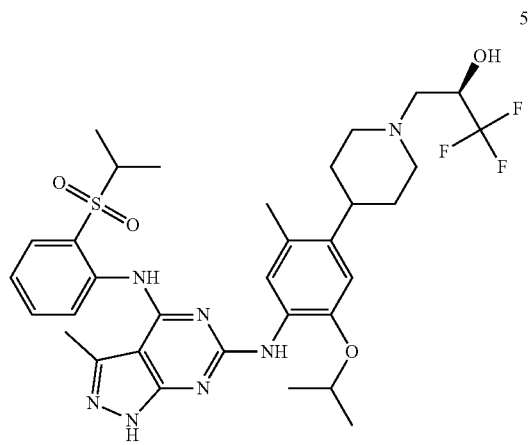

(R)-1,1,1-trifluoro-3-(4-(5-isopropoxy-4-(4-(2-
(isopropysulfonyl)phenylamino)-3-methyl-1H-pyrazolo
[3,4-d]pyrimidin-6-ylamino)-2-methylphenyl)piperidin-1-yl)
propan-2-ol

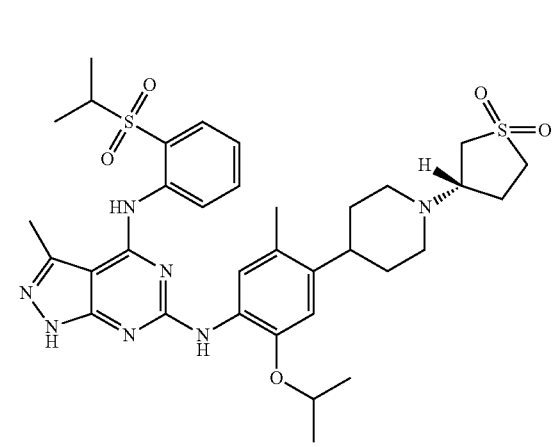

S-N4-(2-(isopropylsulfonyl)phenyl)-N6-(2-isopropoxy-5-methyl-4-
(1-(3-(tetraydrosulfonyl)piperidin-4-yl)phenyl)-3-methyl-1H-
pyrazolo[3,4-d]pyrimidine-4,6-diamine

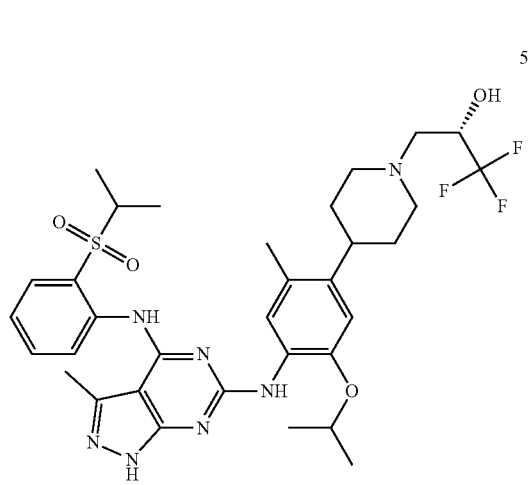

(S)-1,1,1-trifluoro-3-(4-(5-isopropoxy-4-(4-(2-
(isopropylsulfonyl)phenylamino)-3-methyl-1H-pyrazolo[3,4-
d]pyrimidin-6-ylamino)-2-methylphenyl)piperidin-
1-yl)propan-2-ol

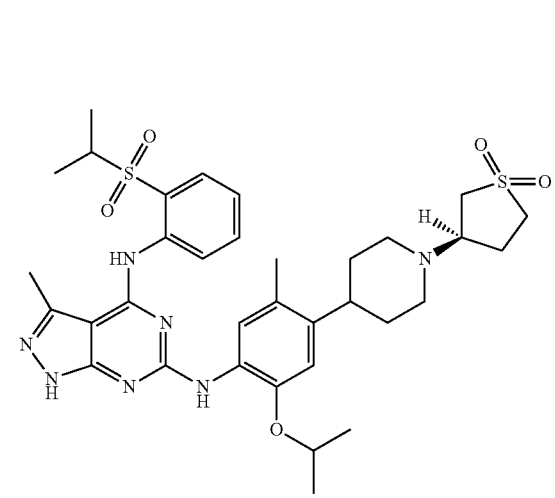

R-N4-(2-(isopropylsulfonyl)phenyl)-N6-(2-isopropoxy-5-
methyl-4-(1-(3-(tetrahydrosulfonyl)piperidin-4-yl)phenyl)-
3-methyl-1H-pyrazolo[3,4-d]pyrimidine-4,6-diamine

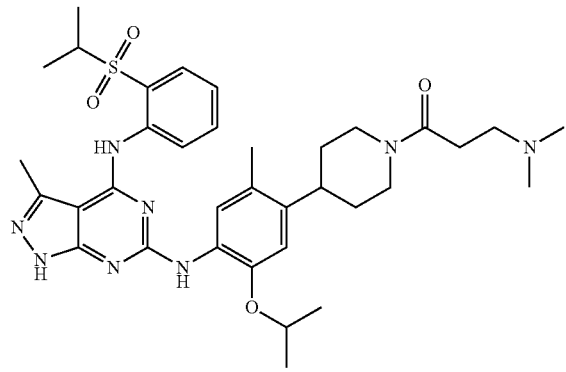

3-(dimethylamino)-1-(4-(5-isopropoxy-4-(4-(2-(isopropylsulfonyl)phenylamino)-3-methyl-1H-pyrazolo[3,4-d]pyrimidin-6-ylamino)-2-methlphenyl)piperidin-1-yl)propan-1-one

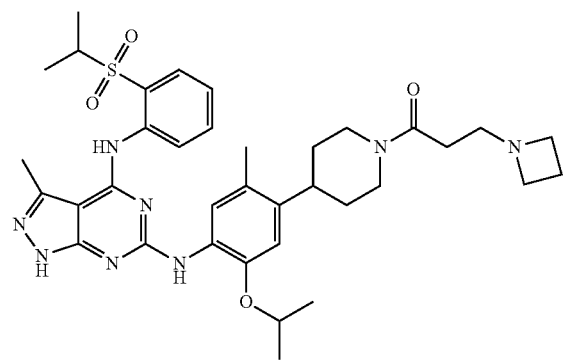

3-(azetidin-1-yl)-1-(4-(5-isopropoxy-4-(4-(2-(isopropylsulfonyl)phenylamino)-3-methyl-1H-pyrazolo[3,4-d]pyrimidin-6-ylamino)-2-methylphenyl)piperidin-1-yl)propan-1-one

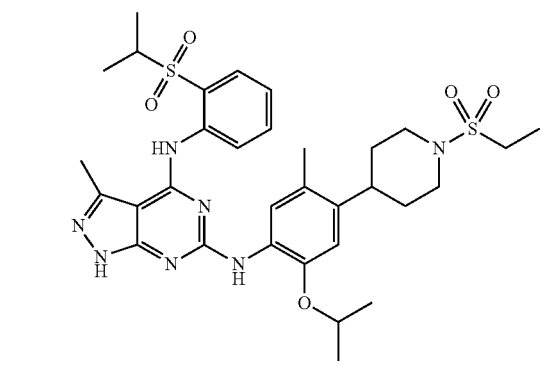

N6-(4-(1-(ethylsulfonyl)piperidin-4-yl)-2-isopropoxy-5-methylphenyl)-N4-(2-(isopropopylsulfonyl)phenyl)-3-methyl-1H-pyazolo[3,4-d]pyrimidine-4,6-diamine

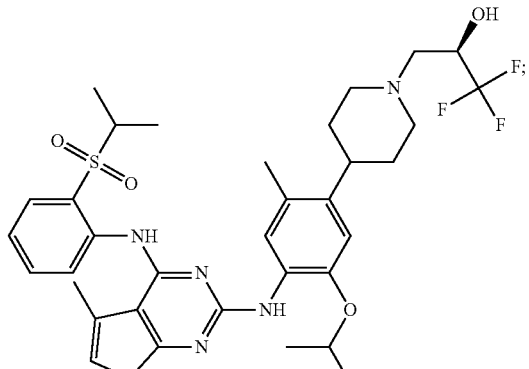

(R)-1,1,1-trifluoro-3-(4-(5-isopropoxy-4-(4-(2-(isopropylsulfonyl)phenylamino)-5-methyl-7H-pyrrolo[2,3-d]pyrimidin-2-ylamino)-2-methylphenyl)piperidin-1-yl)propan-2-ol and

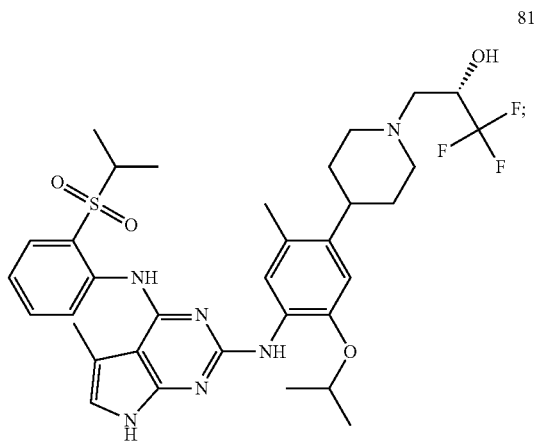

(S)-1,1,1-trifluoro-3-(4-(5-isopropoxy-4-(4-(2-(isopropylsulfonyl)phenylamino)-5-methyl-7H-pyrrolo[2,3-d]pyrimidin-2-ylamino)-2-methylphenyl)piperidin-1-yl)propan-2-ol or pharmaceutically acceptable salts thereof.

8. A pharmaceutical composition comprising a therapeutically effective amount of a compound of claim 1 and a physiologically acceptable carrier.

9. A pharmaceutical composition comprising a therapeutically effective amount of a compound of claim 7 and a physiologically acceptable carrier.

* * * * *